US007060281B1

(12) United States Patent  
Dattwyler et al.

(10) Patent No.: US 7,060,281 B1  
(45) Date of Patent: Jun. 13, 2006

(54) **GROUPS OF *BARRELIA BURGDORFERI* AND *BORRELIA AFZELII* THAT CAUSE LYME DISEASE IN HUMANS**

(75) Inventors: Raymond J. Dattwyler, Setauket, NY (US); Gerald Seinost, Graz (AT); Daniel Dykhuizen, St. James, NY (US); Benjamin J. Luft, Setauket, NY (US); Maria J. C. Gomes-Solecki, New York, NY (US)

(73) Assignees: Research Foundation of the State University of New York, Stony Brook, NY (US); Brook Biotechnology, Inc., Stony, Brook, NY (US)

( * ) Notice: Subject to any disclaimer, the term of this patent is extended or adjusted under 35 U.S.C. 154(b) by 884 days.

(21) Appl. No.: 09/596,746

(22) Filed: Jun. 19, 2000

Related U.S. Application Data

(60) Provisional application No. 60/140,042, filed on Jun. 18, 1999.

(51) Int. Cl.  
*A61K 39/116* (2006.01)  
*A61K 39/00* (2006.01)  
*A61K 39/02* (2006.01)

(52) U.S. Cl. .............................. 424/203.1; 424/184.1; 424/185.1; 424/190.1; 424/192.1; 424/200.1; 424/234.1; 435/320.1; 530/300; 530/350; 536/23.1; 536/23.7

(58) Field of Classification Search ............ 424/184.1, 424/185.1, 190.1, 192.1, 200.1, 203.1, 234.1; 435/320.1; 530/300, 350; 536/23.1, 23.7  
See application file for complete search history.

(56) References Cited

U.S. PATENT DOCUMENTS

| | | | | |
|---|---|---|---|---|
| 5,646,016 A | * | 7/1997 | McCoy et al. ............. | 435/69.7 |
| 5,683,903 A | * | 11/1997 | Lysko et al. ............... | 435/369 |
| 5,756,294 A | * | 5/1998 | White et al. ............... | 435/6 |
| 5,804,427 A | * | 9/1998 | Davis et al. ............... | 435/194 |
| 5,824,318 A | * | 10/1998 | Mohr et al. ............... | 424/229.1 |
| 5,849,891 A | * | 12/1998 | Lin et al. .................. | 536/23.1 |
| 5,863,798 A | * | 1/1999 | Lysko et al. ............... | 435/375 |
| 5,925,548 A | * | 7/1999 | Beutler et al. ............. | 435/69.7 |
| 6,110,703 A | * | 8/2000 | Egel-Mitani et al. ....... | 435/69.1 |
| 6,114,151 A | * | 9/2000 | Cookson et al. ........... | 435/91.2 |
| 6,131,578 A | * | 10/2000 | King et al. ................. | 128/898 |
| 6,150,081 A | * | 11/2000 | Van Heerde et al. ....... | 430/569 |
| 6,194,556 B1 | * | 2/2001 | Acton et al. ............... | 536/23.2 |
| 6,207,883 B1 | * | 3/2001 | Baudot et al. ............. | 800/303 |
| 6,221,363 B1 | | 4/2001 | Livey et al. ............... | 424/234.1 |
| 6,245,525 B1 | * | 6/2001 | Martelange et al. ........ | 435/69.1 |
| 6,248,937 B1 | * | 6/2001 | Finkelstein et al. ......... | 800/290 |
| 6,255,464 B1 | * | 7/2001 | Vogelstein et al. ......... | 536/23.1 |
| 6,268,484 B1 | * | 7/2001 | Katinger et al. .......... | 530/388.35 |
| 6,303,756 B1 | * | 10/2001 | Martelange et al. ...... | 530/387.7 |
| 6,337,208 B1 | * | 1/2002 | Graupner ................... | 435/320.1 |
| 6,420,108 B1 | * | 7/2002 | Mack et al. ................ | 435/6 |
| 6,468,773 B1 | * | 10/2002 | Donald et al. ............. | 435/190 |
| 6,470,277 B1 | * | 10/2002 | Chin et al. ................. | 702/19 |
| 6,472,154 B1 | * | 10/2002 | Garner et al. ............. | 435/6 |
| 6,528,283 B1 | * | 3/2003 | Byrne et al. .............. | 435/69.1 |
| 6,566,094 B1 | * | 5/2003 | Kimura et al. ............ | 435/69.1 |
| 6,627,193 B1 | * | 9/2003 | Travis et al. ............. | 424/94.65 |
| 6,667,065 B1 | * | 12/2003 | Kragh et al. .............. | 426/28 |

FOREIGN PATENT DOCUMENTS

| WO | WO 94/19697 | 9/1994 |
|---|---|---|
| WO | WO 94/25596 | 11/1994 |
| WO | WO 95/12676 | 5/1995 |
| WO | WO 96/40290 | 12/1996 |
| WO | WO 97/42221 | 11/1997 |
| WO | WO 99/14345 | 3/1999 |
| WO | WO 00/06745 | 2/2000 |

OTHER PUBLICATIONS

Wang, Ing-Nang et al., "Genetic Diversity of ospC in a Local Population of *Borrelia burgdorferi* sensu stricto," *Genetics*, 151:15-30 (1999).

de Silva, Aravinda M. et al., "Perspectives Series: Host/Pathogen Interactions, Arthropod- and Host-specific Gene Expression by *Borrelia burgdorferi*," *J. Clin. Invest.*, 99(3):377-379 (1997).

Fingerle, Volker et al., "Expression of outer surface proteins A and C of *Borrelia burgdorferi* in *Ixodes ricinus* ticks removed from humans," *Med. Microbiol. Immunol.*, 187:121-126 (1998).

Gilmore, Robert D. et al., "Outer Surface Protein C (OspC), but Not P39, Is a Protective Immunogen against a Tick-Transmitted *Borrelia burgdorferi* Challenge: Evidence for a Conformational Protective Epitope in OspC," *Infection and Immunity*, 64(6):2234-2239 (1996).

Montgomery, Ruth R. et al., "Direct Demonstration of Antigenic Substitution of *Borrelia burgdorferi* Ex Vivo: Exploration of the Paradox of the Early Immune Response to Outer Surface Proteins A and C in Lyme Disease," *J. Exp. Med.*, 183:261-269 (1996).

Probert, William Scott et al., "Immunization with Outer Surface Protein (Osp) A, But Not OspC, Provides Cross-Protection of Mice Challenged with North American Isolates of *Borrelia burgdorferi*," *The J. of Infectious Disease*, 175:400-405 (1997).

(Continued)

*Primary Examiner*—Rodney P. Swartz  
(74) *Attorney, Agent, or Firm*—Hamilton, Brook, Smith & Reynolds, P.C.

(57) ABSTRACT

The present invention is drawn to an immunogenic composition comprising OspC polypeptides from Lyme Disease causing *Borrelia*. In one embodiment, the immunogenic composition of the present invention comprises at least one OspC polypeptide or immunogenic fragment thereof from each of *Borrelia burgdorferi* OspC families A, B, I and K. In another embodiment, the immunogenic composition of the present invention comprises at least one OspC polypeptide or immunogenic fragment thereof from each of *Borrelia afzelii* OspC families A and B.

19 Claims, 8 Drawing Sheets

OTHER PUBLICATIONS

Probert, William Scott et al., "Protection of C3H/HeN Mice from Challenge with *Borrelia burgdorferi* through Active Immunization with OspA, OspB, or OspC, but Not with OspD or the 83-Kilodalton Antigen," *Infection and Immunity*, 62(5):1920-1926 (1994).

Schwan, Tom G. et al., "Induction of an outer surface protein on *Borrelia burgdorferi* during tick feeding," *Proc. Natl. Acad. Sci., USA*, 92:2909-2913 (1995).

Simon, Markus M. et al., "Lyme Disease: Pathogenesis and Vaccine Development," *Zent.bl. Bakteriol*, 289:690-695 (1999).

Steigbigel, Roy T. et al., "Immunization against Lyme Disease—An Important First Step," *NEJM*, 339(4):263-264 (1998).

Stover, C. K. et al., "Protective Immunity Elicited by rBCG Vaccines," *Dev. Biol. Stand. Basel, Karger*, 82:163-170 (1994).

Wahlberg, Peter, "Vaccination against Lyme borreliosis," *Ann. Med.*, 31:233-235 (1999).

Wilske, Bettina et al., "Immunological and Molecular Polymorphisms of OspC, an Immunodominant Major Outer Surface Protein of *Borrelia burgdorferi*," *Infection and Immunity*, 61(5):2182-2191 (1993).

Wilske, B. et al., "Immunological and Molecular Variability of OspA and OspC. Implications for *Borrelia* Vaccine Development," *Infection*, 24(2):208-212 (1996).

Wilske, Bettina et al., "Diversity of OspA and OspC among cerebrospinal fluid isolates of *Borrelia burgdorferi* sensu lato from patients with neuroborreliosis in Germany," *Med. Microbiol. Immunol.*, 184:195-201 (1996).

Zhong, Weimin et al., "Resolution of experimental and tick-borne *Borrelia burgdorferi* infection in mice by passive, but not active immunization using recombinant OspC," *Eur. J. Immunol.*, 29:946-957 (1999).

Zhong, Weimin et al., "Therapeutic passive vaccination against chronic Lyme disease in mice," *Proc. Natl. Acad. Sci., USA*, 94:12533-12538 (1997).

\* cited by examiner

|  | Early Lyme: #P(total) | | | | Sensitivity | | Potential cross-reactivity: #P(Total Tested) | | | | Specificity | |
|---|---|---|---|---|---|---|---|---|---|---|---|---|
|  | EMA | EA | Ac. Dissem. | Ac. Conval. | #P(Total) | (%) | Syphilis | SLE &RA | Normals End. | Normals NonEnd. | #P(Total) | (%) |
| C1 (chrt1) | 6(10) | ND | 4(10) | 8(8) | 18(28) | 64% | 1(10) | 1(10) | 2(10) | 0(8) | 4(38) | 11% |
| C2 (chrt2) | 4(10) | ND | 5(10) | 8(8) | 17(28) | 61% | 0(10) | 2(10) | 2(10) | 0(8) | 4(38) | 11% |
| C1C10 (chrt3) | 7(10) | ND | 4(10) | 5(8) | 16(28) | 57% | 4(10) | 1(10) | 2(10) | 0(8) | 7(38) | 18% |
| C1C12 (chrt4) | 2(10) | ND | 3(10) | 5(8) | 10(28) | 36% | 2(10) | 0(10) | 0(10) | ND | 2(30) | 7% |
| B31C10 (chrt5) | 8(10) | ND | 6(10) | 5(8) | 19(28) | 68% | 2(10) | 2(10) | 4(10) | 0(8) | 8(38) | 21% |
| B31C12 (chrt6) | 7(10) | ND | 6(10) | 6(8) | 19(28) | 68% | 1(10) | 1(10) | 1(10) | 0(8) | 3(38) | 8% |
| C2C7 (chrt7) | 5(10) | 6(8) | 3(10) | 4(7) | 18(35) | 51% | 1(11) | 0(10) | 1(20) | 0(8) | 2(49) | 4% |
| C2C10 (chrt8) | 4(10) | 7(8) | 5(10) | 4(7) | 20(35) | 57% | 0(11) | 0(10) | 1(20) | 0(8) | 1(49) | 2% |
| C2C12 (chrt9) | 5(10) | 7(8) | 6(10) | 4(7) | 22(35) | 63% | 0(11) | 1(10) | 3(20) | 0(8) | 4(49) | 8% |
| C5C7 (chrt10) | 7(10) | ND | 4(10) | 5(8) | 16(28) | 57% | 2(10) | 2(10) | 0(10) | ND | 4(30) | 13% |
| C5C10 (chrt11) | 6(10) | ND | 4(10) | 5(8) | 15(28) | 54% | 0(10) | 0(10) | 0(10) | ND | 0(30) | 0% |
| C5C12 (chrt12) | 8(10) | ND | 8(10) | 6(8) | 22(28) | 79% | 5(10) | 3(10) | 3(10) | 0(8) | 11(38) | 29% |

EMA = Erythema Migrans Acute
EA = Acute Disseminated
Ac. Dissem.= Acute Disseminated
Ac. Conval. = Acute Convalescent
P = Number of positives
SLE = Systemic Lupus Erythematosus
RA = Rheumatoid Arthritis
End. = Endemic Field Workers
NonEnd. = Non Endemic

Fig. 8

GROUPS OF BARRELIA BURGDORFERI AND BORRELIA AFZELII THAT CAUSE LYME DISEASE IN HUMANS

RELATED APPLICATIONS

This application claims the benefit of U.S. Provisional Application No. 60/140,042, filed Jun. 18, 1999, the entire teachings of which are incorporated herein by reference in their entirety.

GOVERNMENT SUPPORT

The invention was supported, in whole or in part, by grant AIAR37256 from The National Institutes of Health, grant ROA1AI33454 from the National Institute of Infectious Disease and cooperative agreement number U50/CCU210518 from the Centers for Disease Control. The Government has certain rights in the invention.

BACKGROUND OF THE INVENTION

Lyme disease begins at the site of a tick bite, producing a primary infection with spread of the organism to secondary sites occurring early in the course of infection. Lyme disease is a progressive multi-system disorder and is the most common vector-borne disease in both North America and Europe. This disease was first described as a focus of pediatric arthritis patients in Old Lyme, CT (Steere, A. C., et al., *Arth. Rheum.,* 20:17 (1977)). The association of this syndrome with the bite of the deer tick, *Ixodes scapularis*, led to the identification of the spirochete *Borrelia burgdorferi* as the causative agent (Burgdorfer, W., et al., *Science,* 216:1317–1319 (1982)). As culture isolation of the bacterium from clinical and field samples became more efficient, Baranton and colleagues described three pathogenic genospecies, *B. burgdorferi* sensu stricto (*B. burgdorferi* or B.b.s.s.), *B. afzelii*, and *B. garinii* (Baraton, G., et al., *Int. J. Syst. Bacteriol.,* 42:378–383 (1992)). These are members of a species complex, *B. burgdorferi* sensu lato, which consists of at least 10 different genospecies (Piken, R. N., et al., *J. Invest. Dermatol.,* 110:211–214 (1998); Postic, D., et al., *Int. J. Syst. Bacteriol.,* 44:743–752 (1994); Valsangiacomo, C. T., et al., *Int. J. Syst. Bacteriol.,* 47:1–10 (1997)). *B. burgdorferi, B. afzelii and B. garinii* are thought to be pathogenic and all are found in Europe, but in North America, *B. burgdorferi* is the only pathogenic genospecies found. Each of these three genospecies is associated with distinct clinical manifestations (Van Dam, A. P. et al., *Clin. Infect. Dis.,* 17:708–717 (1993)). This implies that differences in genospecies may play an important role in the wide array of clinical manifestations observed in Lyme Disease.

As an infected tick begins to feed on a mammal, the synthesis of outer surface protein C (OspC) is induced (Schwan, T. G., et al., *Proc. Natl. Acad. Sci.* 2:2909–2913 (1995)). Thus, in early infection, OspC is the major outer membrane protein expressed by the spirochete (Fung, B. P., et al., *Infect. Immun.* 62:3213–3221 (1994); Padula, S. J., et al., *J. Clin. Microbiol.,* 32:1733–1738 (1994)). Even through OspC has been demonstrated to have limited surface exposure (Cox, D. L., et al., *Proc. Natl. Acad. Sci.,* 93:7973–7978 (1996); Mathiesen, M. M., et al., *Infect Immun.* 66:4073–4079 (1998)), OspC is a potent immunogen. Immunization with OspC is protective against tick-transmitted *Borrelia* infection (Gilmore Jr., R. D., *Infect Immun.* 64:2234–2239 (1999)). However, because OspC is highly variable in its sequence, the protection is limited to the

*Borrelia burgdorferi* strain expressing the same immunizing OspC encoded by a specific allele. Challenge with heterologous isolates, expressing other ospC alleles results in infection (Probert, W. S., et al., *J. Infect. D.,* 175:400–405 (1997)). OspC is very diverse (Jauris-Heipke, S., et al., *Med. Microbiol. Immunol.* 182:37–50 (1993)). Livey et al. found thirty-four alleles in seventy-six *B. burgdorferi* sensu lato isolates (Livey, I., et al., *Mol. Microbiol.* 18:257–269 (1995)).

Currently, Lyme Disease is treated with antibiotics. However, such treatment is not always successful in clearing the infection. Treatment is often delayed due to improper diagnosis with the deleterious effect that the infection proceeds to a chronic condition, where treatment with antibiotics is often not useful. One of the factors contributing to delayed treatment is the lack of effective diagnostic tools.

Furthermore, while antigens such as OspC are known to be protective, in some cases the existence of multiple alleles of these antigens greatly hinders the development of vaccines based on such antigens that would protect against more than one strain of *Borrelia*. Two independent trials of first generation vaccines for the prevention of Lyme disease, recently studied the efficacy and safety of a vaccine that is based on recombinant outer surface protein A (OspA) (Sigal, L. H. et al., *N. Engl. J. Med* 339:216–222, 1998; Steere, A. C. et al., *N. Engl. J. Med.* 339:209–215, (1998)). However, a vaccine that consists of recombinant OspA may require frequent booster immunizations. Natural infection with *B. burgdorferi* does not elicit an antibody response to OspA, as it does against OspC. What is needed is a selection of *Borrelia* antigens that can be used to either diagnose or vaccinate against all or most forms of *Borrelia* that cause systemic disease.

Differences in the frequency of *B. burgdorferi, B. garinii,* and *B. afzelii* in ticks and human infection has lead to the hypothesis that the different genospecies are differentially pathogenic (Picken, R. N. et al., *J. Invest. Dermatol.* 110:211–214, 1998; Van Dam, A. P. et al., *Clin. Infect. Dis.* 17:708–717, 1993). Nevertheless, the number of different strains within a given genospecies and the differences between the strains of a given genospecies as well as between genospecies impose obstacles in the development of immunogenic protein compounds for use as diagnostic and vaccine agents in the detection, prevention and treatment of Lyme disease. A number of investigators have used OspC as a serodiagnostic antigen for early Lyme disease (Fung, B. P. et al., *Infect. Immun.* 62:3213–3221, 1994; Gerber, M. A. et al., *J. Infect. Dis.* 171:724–727, 1995; Padula, S. J. et al., *J. Clin. Microbiol.* 32:1733–1738, (1994)). In these tests, the use of OspC as a diagnostic antigen gave highly specific, but not sensitive results. However, these studies included only one *B. burgdorferi* strain and therefore only one type of OspC. Routine tests for the diagnosis of Lyme disease also use a single strain protocol and therefore a single OspC allele for detection of antibody to the sprirochete. It is not clear what mixture of OspC proteins must be used to make useful diagnostic and vaccine tools, effective against more than one Lyme disease causing strains of *Borrelia*, if not against most if not all of the invasive strains within a genospecies. Preferably, such a mixture would be effective against all invasive strains of Lyme disease causing *borrelia.*

SUMMARY OF THE INVENTION

The present invention is drawn to a composition comprising OspC polypeptides from Lyme Disease causing

*Borrelia.* In one embodiment, the composition of the present invention comprises an OspC polypeptide or fragment thereof from at least two *Borrelia burgdorferi* OspC families selected from the group consisting of A, B, I and K, excepting the combination consisting of two OspC proteins, wherein one OspC protein is from OspC family A and the second OspC protein is from OspC family I. In another embodiment, the composition of the present invention comprises at least one OspC polypeptide or fragment thereof from each of *Borrelia afzelii* OspC families A and B.

The present invention is also drawn to a method of immunizing an animal against Lyme disease, comprising administering a composition comprising OspC polypeptides from Lyme Disease causing *Borrelia*. In one embodiment of the present invention, the composition comprises a OspC polypeptide or fragment thereof from at least two *Borrelia burgdorferi* OspC families selected from the group consisting of: A, B, I and K, excepting the combination consisting of two OspC proteins, wherein one OspC protein is from OspC family A and the second OspC protein is from OspC family I. In another embodiment of the present invention, the composition comprises at least one OspC polypeptide or fragment thereof from each of *Borrelia afzelii* OspC families A and B. The composition of the present invention together with suitable excipients and/or adjuvants is administered to an animal such that the animal develops an immune response to at least one OspC polypeptide of the composition.

The present invention is also drawn to a method of detecting an immune response to Lyme Disease causing *Borrelia* in a host sample. The method comprises contacting a host sample with a composition comprising OspC polypeptides from Lyme disease causing strains of *Borrelia*, such that anti-OspC antibodies, if present, in said sample bind to said OspC polypeptides. In one embodiment, the composition comprises at least one OspC polypeptide or fragment thereof from each of *Borrelia burgdorferi* OspC families A, B, I and K. The amount of antibodies that have bound said OspC polypeptides or fragments thereof are measured; thereby detecting an immune response to Lyme disease causing *Borrelia*.

The present invention is also drawn to a diagnostic kit comprising OspC polypeptides from Lyme Disease causing *Borrelia*. In one embodiment of the present invention, the diagnostic kit comprises at least one OspC polypeptide or diagnostic fragment thereof from each of *Borrelia burgdorferi* OspC families A, B, I and K. In another embodiment of the present invention, the diagnostic composition comprises at least one OspC polypeptide or diagnostic fragment thereof from each of *Borrelia afzelii* OspC families A and B.

In other embodiments of the present invention, the composition comprises at least one OspC polypeptide or fragment thereof from each of *Borrelia afzelii* OspC families A and B. In still other embodiments, the composition comprises OspC polypeptides or fragments thereof from *Borrelia burgdorferi, Borrelia afzelii, Borrelia garinii* and combinations thereof.

The present invention is also drawn to chimeric proteins for use in the methods of the present invention. In one embodiment, the present invention is drawn to a chimeric protein comprising OspC polypeptides from two or more OspC families of Lyme Disease causing *Borrelia*. In one embodiment, the families comprise *Borrelia burgdorferi* OspC families A, B, I and K. In other embodiment, the families comprise *Borrelia afzelii* OspC families A and B. In still other embodiments, the composition comprises chimeric OspC polypeptides or fragments thereof from *Borrelia burgdorferi, Borrelia afzelii, Borrelia garinii* and combinations thereof.

The chimeric proteins of the present invention comprise at least a first and a second polypeptide of OspC, such that the first polypeptide comprises OspC from about base 26 to about base 630 of a first ospC gene and the second polypeptide comprises about base 28 to about base 570 of a second ospC gene. The chimeric proteins of the present invention can be used in the immunization and detection methods of the present invention.

The present invention provides the minimum number of *Borrelia burgdorferi* and *Borrelia afzelii* families that are responsible for systemic disease in humans and is useful for vaccines and diagnostic kits. The present invention provides a combination of proteins that, when used as a vaccine, prevent Lyme disease from becoming systemic. The proteins and chimeric proteins of the present invention can be effective in preventing of Lyme disease as well as having a therapeutic effect on established infection, for example after the tick bite is noticed by the patient. The proteins and chimeric proteins of the present invention are expected to act at the level of the tick as well as the level of the host in preventing both infection and disease due to *Borrelia burgdorferi, Borrelia afzelii* and/or *Borrelia garinii*. The present invention allows the development of a worldwide vaccine comprising only six proteins necessary to generate a protective immune response against all pathogenic strains of *Borrelia burgdorferi* and *Borrelia afzelii*.

The present invention also provides improved diagnostic tools. Because of the present invention, it is now possible to prepare diagnostic tools comprising OspC antigens representing the four pathogenic families of *Borrelia burgdorferi* and/or the two pathogenic families of *Borrelia afzelii*, thereby detecting clinically important exposure to pathogenic bacteria while overlooking the remainder of the families which do not cause pathogenic disease.

As demonstrated herein, a significant proportion, if not all, systemic *B. burgdorferi* sensu stricto infections in humans are associated with four ospC groups and that a significant portion, if not all, systematic *B. afzelii* infections in humans are associated with two ospC groups. Vaccines against OspC are known to be protective, but have been limited by the diversity of ospC (Probert, W. S. et al., *J. Infect. D.* 175:400–405, (1997)). The polypeptides of the present invention provide immunogenic proteins, fragments and chimeric proteins thereof for highly protective vaccines and diagnostics. The present invention provides a vaccine that includes one or more of these four forms of OspC. The vaccines of the present invention should be an important second level of protection against disseminated infection of the *B. burgdorferi* spirochete. Furthermore, single-stranded conformational polymorphism (SSCP) analysis described herein may provide a rapid and powerful tool to monitor vaccine efficacy by detecting rare or new invasive ospC groups.

New diagnostic assays of the present invention, based on major ospC groups A, B, I, and K are useful to identify those at risk for progressive illness. Given that OspC proteins are antigenically variable, individuals infected with one strain may produce an antibody response that is not reactive with an OspC protein from a different major group. Antibody detection using antigen preparations of the present invention, incorporating a proper mix of invasive clones of *B. burgdorferi* will be much more sensitive than the present, single strain protocols. The compositions of the present invention not only elicit humoral and cell mediated immune responses, the compositions of the present invention are also capable of detecting both humoral and cell mediated immune response when used to test a host sample.

The present invention provides both lipidated OspC polypeptides, fragments thereof and chimeric proteins comprising two or more OspC polypeptides, wherein the chimeric protein has a lipidation signal, such as the lipidation signal from outer surface protein B at the 5' terminus of the gene encoding the chimera. Furthermore, the present invention provides unlipidated OspC polypeptides, fragments thereof and chimeric proteins comprising two or more OspC polypeptides, wherein the gene encoding the chimeric protein does not comprise a lipidation signal and the chimeric protein is not lipidated. Unlipidated OspC polypeptides, fragments thereof and chimeric proteins thereof are advantageous due to simpler production methods, improved yields of protein and simpler purification. The unlipidated chimeric proteins of the present invention unexpectedly elicit an immune response against Lyme disease causing strains of Borrelia at least as broadly reactive as lipidated OspC proteins that are used as a positive control. Furthermore, the unlipidated OspC chimeric proteins of the present invention elicit an immune response to more than one genospecies of Lyme disease causing strains of Borrelia, including genospecies and strains that are not used to generate the chimeric OspC immunogen.

BRIEF DESCRIPTION OF THE DRAWINGS

FIG. 2 is a bar graph showing the reactivity of serum from mice immunized with the indicated Borrelia protein or recombinant chimeric Borrelia protein (X-axis) against the indicated OspC antigens (legend) where the serum is from the first bleed.

FIG. 4 is a bar graph showing the reactivity of serum from mice immunized with the indicated Borrelia protein or chimeric recombinant Borrelia protein (X-axis) against the indicated strains of Borrelia burgdorferi sensu stricto (legend).

FIG. 8 is a Table comparing the reactivity of lipidated OspC proteins C1 and C2 against sera from patients with the indicated condition with the reactivity of the unlipidated chimeric proteins of the present invention, where the number in parentheses is the total number of sera tested in that category.

DETAILED DESCRIPTION OF THE INVENTION

Figure 1:
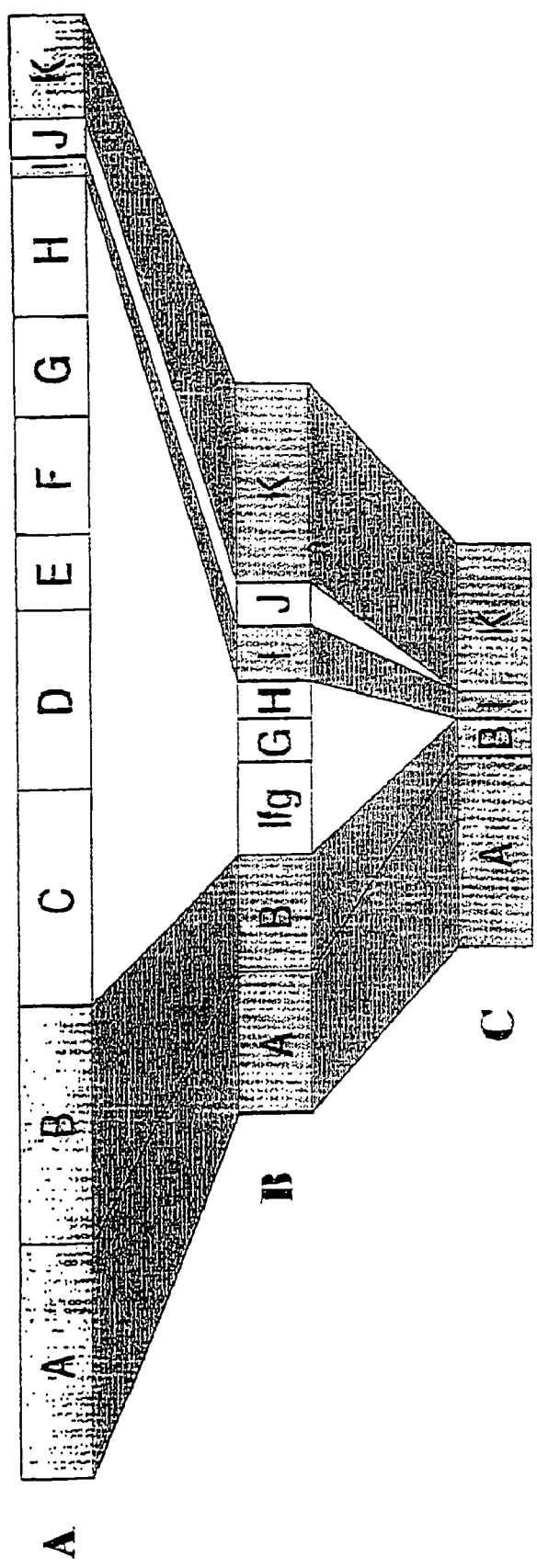
FIG. 1 is a schematic diagram of the frequency distribution of major ospC groups among B. burgdorferi isolates from Eastern Long Island Ixodes scapularis ticks.

As described herein, initially nineteen groups of ospC from B. burgdorferi sensu stricto were found within a small tick population (Wang, I-N., et al., Genetics, 151:15–30 (1999)). Major ospC groups were defined using the observation that ospC alleles are either very similar, having less than 2% sequence divergence, or very different, having greater than 8% sequence divergence, with most having greater than 14% sequence divergence.

Based on sequence divergences, alleles of ospC can be grouped into twenty-one major groups (Table II). To assess whether strain differences as defined by a given ospC group are linked to invasiveness and pathogenicity, the frequency distributions of major ospC groups from ticks, from the primary erythema migrans (EM) skin lesion, and from secondary sites, principally from blood and spinal fluid, were compared. As described herein, the frequency distribution of ospC groups from ticks is significantly different from that of primary site infection which in turn is significantly different from secondary sites. The major ospC groups A, B, I and K increased in frequency from ticks to the primary site and were the only groups found in secondary sites of the infection. Therefore, three categories of major ospC groups are defined herein. One category is common in ticks but very rarely, if ever, causes human disease, a second category that causes only local infection at the tick bite site, and a third category that causes systemic or disseminated disease. While many ospC groups found in ticks were also found in primary skin lesions, the frequency distributions are significantly different between ticks and primary skin lesions (Table III). All ospC groups were found more or less commonly in ticks. However, only four groups are commonly found in skin lesions or secondary infections (Tables III and IV). As described herein, the primary skin lesions harbored Borrelia having ospC groups other than A, B, I or K rarely or not at all. More importantly, only these four ospC groups were found in secondary sites. The finding that all systemic B. burgdorferi sensu stricto infections are associated with four ospC groups has importance in the diagnosis, treatment and prevention of Lyme disease.

There is evidence that ospC has been transferred between strains and even between genospecies (Wang I-N, et at., Genetics, 151:15–30 (1998)). This is not true of Borrelia chromosomal genes (Dykhuizen, D. E., et al., Proc. Natl. Acad. Sci., 30:10163–10167 (1999); Maynard Smith, J. and Smith, N. H., Mol. Biol. Evol., 15:590–599 (1998)). However, ospA and ospC alleles in B. burgdorferi sensu stricto are almost completely linked (Wang I-N, et al., Genetics, 151:15–30 (1999)). This suggests that once an ospC allele has been transferred into a particular background, there is little or no selection for another similar recombination event. Thus, each major ospC group represents a clonal population descended from a single recombination.

Twenty percent of untreated erythema migrans clear spontaneously without causing any systemic complications (Steere, A. C. et al., Arth. Rheum. 20:7–17, (1977)). As demonstrated herein, this is not significantly different (p=0.25 for a 2 by 2 contingency test with double dichotomy) from the percent of non-invasive strains found in the skin, suggesting that the erythema migrans that clear spontaneously are caused by non-invasive clones.

There is extensive genetic and antigenic diversity of ospC in all three pathogenic genospecies of B. burgdorferi sensu lato (Livey, I. et al., Mol. Microbiol. 18:257–269, 1995; Masuzawa, T. et al., Clin. Diagn. Lab. Immunol. 4:60–63, 1997; Picken, R. N. et al., *J. Invest. Dermatol.* 110:211–214, 1998; Theisen, M. et al., *J. Clin. Microbiol.* 31:2570–2576, 1993; Wang, I-N. et al., *Genetics* 151:15–30 (1999). As demonstrated herein, only four groups of ospC alleles are linked to both infectivity and invasiveness, and that invasiveness is confined to a small number of ospC clones. It is clear that the ospA and ospC alleles are tightly linked even though they are on different plasmids (Wang, I-N. et al., *Genetics* 151:15–30 (1999)). If the invasiveness is caused by allelic variation at another locus, this variation is likely to be tightly linked to the ospC variation. Thus, ospC is a good marker for human pathogenicity and perhaps its determinator. These findings have important implications not only for our understanding of the pathogenesis of this disease but for its diagnosis and prevention.

Spirochetemia is a transient phenomenon, but is presumably key in seeding secondary skin sites, the heart, joints, and nervous system, where these *Borrelia* cause the secondary and tertiary clinical manifestations of Lyme disease. All four invasive groups of *Borrelia burgdorferi* were found in isolates from blood and CSF. The one joint isolate belonged to group A. However, it can be inferred that groups not found in the blood will not be found in the joints since most if not all dissemination of *Borrelia* to secondary sites is via blood.

Normally, model organisms are used as substitutes for experiments on humans. However, this substitution works only as long as the properties of the model organism and of humans are the same for the studied phenomena. The human immune system plays a critical role which is expected to be different from the immune response in model organisms, particularly the mouse. Humans are accidental and usually dead-end hosts while the mouse is a critical host reservoir. The field of population genetics has developed sound procedures for reaching conclusions from survey data.

The chimeric polypeptides of the present invention elicit specific immune responses to OspC. The chimeric polypeptides also elicit immune response against strains of Lyme disease causing *Borrelia* of the same genospecies as that represented by the chimeric OspC as well as Lyme disease causing *Borrelia* of different genospecies than that represented by the chimeric OspC. The immune response includes humoral responses, secretory responses, cell-mediated responses and combinations thereof in an animal treated with the compositions of the present invention. The compositions of the present invention can include additional components suitable for in vitro and in vivo use. These additional components include buffers, carrier proteins, adjuvants, preservatives and combinations thereof.

The immunogenic compositions of the present invention can be used to immunize animals including humans. Immunization is understood to elicit specific immunogenic responses as described above. As described herein, an immunogenic response includes responses that result in at least some level of immunity in the treated animal, where the animal was treated with a composition comprising at least one protein or chimeric protein of the present invention. In one embodiment, the treated animal develops immunity against infection by Lyme disease causing *Borrelia*, wherein the chimeric proteins of the present invention elicit responses against *Borrelia burgdorferi, Borrelia afzelii* and *Borrelia garinii*.

Immunity, as described herein, is understood to mean the ability of the treated animal to resist infection, to resist systemic infection, to overcome infection such as systemic infection or to overcome infection such as systemic infection more easily or more quickly when compared to non-immunized or non-treated individuals. Immunity can also include an improved ability of the treated individual to sustain an infection with reduced or no clinical symptoms of systemic infection. The individual may be treated with the chimeric proteins of the present invention either proactively, e.g. once a year or maybe treated after sustaining a tick bite.

For use as a vaccine, the composition of the present invention can include suitable adjuvants, well known in the art, to enhance immunogenicity, potency or half-life of the chimeric proteins in the treated animal. Adjuvants and their use are well known in the art (see for example PCT Publication WO 96/40290, the entire teachings of which are incorporated herein by reference). The composition can be prepared by known methods of preparing vaccines. For example, the OspC proteins or chimeric proteins to be used in the compositions can be isolated and/or purified by known techniques such as by size exclusion chromatography, affinity chromatography, preparative electrophoresis, selective precipitation or combinations thereof. The prepared proteins or chimeric proteins can be mixed with suitable other reagents as described above, where the chimeric protein is at a suitable concentration. The dosage of protein or chimeric protein will vary from one µg to 500 µg and depends upon the age, weight and/or physical condition of the animal to be treated. The optimal dosage can be determined by routine optimization techniques, using suitable animal models.

The composition to be used as a vaccine can be administered by any suitable technique. In one embodiment, administration is by injection, e.g. subcutaneous, intramuscular, intravenous, or intra peritoneal injection. In another embodiment, the composition is administered to mucosa, e.g. by exposing nasal mucosa to nose drops containing the proteins of chimeric proteins of the present invention. In another embodiment, the immunogenic composition is administered by oral administration. In another embodiment of the present invention the chimeric proteins are administered by DNA immunization.

Like many outer surface proteins of *Borrelia*, OspC is produced in the *Borrelia* spirochete with 5' lipidation. The chimeric polypeptides of the present invention can be produced in both lipidated and non-lipidated form. In one embodiment, the lipidation signal encoded by the wild type ospC is removed from the coding sequence, such that the gene or chimeric gene encodes a non-lipidated OspC or chimeric OspC polypeptide. In another embodiment of the present invention, the lipidation signal of the wild type ospC gene is replaced with the lipidation signal of the ospB gene. In this embodiment, a lipidated OspC or OspC chimeric protein is produced.

The polypeptides of the present invention can be recombinantly expressed in suitable microbial hosts, wherein said hosts include, but are not limited to, bacterial hosts, such as *E. coli*, fungal hosts *S. cerevisiae*, or cell culture hosts such as mammalian cell culture or insect cell culture.

While the lack of lipidation signal allows for the production of large amounts of OspC proteins and chimeric OspC proteins, the lack of lipidation signal was previously thought to render outer surface proteins of *Borrelia* less or non-immunogenic. However, as described herein, the non lipidated chimeric polypeptides of the present invention unexpectedly elicit as broad an immunogenicity as lipidated OspC protein (FIGS. 2 and 3) and greater immunogenicity against strains of other genospecies (FIGS. 5–7) compared to the positive controls, which were lipidated OspC from B31 and lipidated OspC from C12.

The proteins and chimeric proteins of the present invention are also antigenic and therefore useful to detect or diagnose the presence of Lyme disease causing *Borrelia*, especially *Borrelia* from groups capable of causing disseminated symptoms of Lyme disease. As described herein, disseminated symptoms refers to infection outside of the erythema migrans skin lesion, e.g. infection in blood, CNS or synovia. As described herein, antigenic refers to the ability of a compound to bind products of an immune response, such as antibodies, T-cell receptors or both. Such responses can be measured using standard antibody detection assays, such as ELISA or standard T-cell activation assays.

The present invention is drawn to compositions comprising OspC polypeptides from Lyme disease causing *Borrelia* and chimeric OspC polypeptides. In one embodiment of the present invention, compositions include one or more OspC polypeptide or fragment thereof from at least two *Borrelia burgdorferi* ospC groups, referred also herein as families, selected from the group consisting of A, B, I and K, excepting the combination consisting of two OspC polypeptides from the A and I families. In another embodiment of the present invention, the compositions of the present invention include at least one OspC polypeptide or fragment thereof from each of *Borrelia burgdorferi* ospC families A, B, I and K. In another embodiment, the composition includes at least one OspC polypeptide or fragment thereof from each of *Borrelia afzelii* OspC families A and B. In still another embodiment, the composition includes OspC polypeptides from at least one *Borrelia burgdorferi* OspC group or family member selected from the group consisting of A, B, I and K and at least one *Borrelia afzelii* OspC family member selected from the group consisting of A and B.

As described herein, the ospC families of the present invention share about 98% homology at the nucleic acid level between strains of the same family and share no more than about 92% homology at the nucleic acid level between strains of different families. Determination of homology excludes any non-ospC sequences. Members of the same ospC family have similar antigenic profiles, e.g. elicit immune response against similar strains of Lyme disease causing *Borrelia*. The chimeric proteins of the present invention unexpectedly elicit immune response to Lyme disease causing *Borrelia* of different genospecies than the genospecies from which the component polypeptides were derived. In one embodiment of the present invention, *Borrelia burgdorferi* ospC family A comprises strains B31, CA4, HII, IP1, IP2, IP3, L5, PIF, PKA, TXGW and strains of *Borrelia* containing ospc allele OC1. In another embodiment of the present invention, *Borrelia burgdorferi* ospC family B comprises strains 35B808, 61BV3, BUR, DK7, PB3, ZS7 and strains containing ospC alleles OC2 and OC3. In still another embodiment of the present invention, *Borrelia burgdorferi* ospC family I comprises strains 297, HB19 and strains containing ospC allele OC10, wherein strain 297 is characterized by ospC of GenBank Accession No. L42893 (SEQ ID NO:85). In still another embodiment of the present invention, *Borrelia burgdorferi* ospC family K comprises strains 272, 297, 28354, KIPP, MUL and strains containing ospC allele OC12 and OC13, wherein strain 297 is characterized by ospC of GenBank Accession No. U08284 (SEQ ID NO:86).

In another embodiment of the present invention, said compositions comprise an OspC polypeptide or fragment thereof from each of *Borrelia afzelii* OspC families A and B. In one embodiment of the present invention, *Borrelia afzelii* OspC family A comprises strains Pbo, Pwud, Pko, Pgau, DK2, DK3, DK21, DK8, Bfox and JSB. In another embodiment of the present invention *Borrelia afzelii* OspC family B comprises strains DK5, ACA1, DK9, XB18h, Ple and 143M. As described above for *Borrelia burgdorferi* the compositions also include chimeric OspC polypeptides of *Borrelia afzelii* families A and B.

In one embodiment of the present invention, the OspC polypeptide OspC polypeptide is a chimeric OspC comprising at least one OspC protein variable region or portion thereof from at least one ospC gene. In one embodiment of the present invention, the OspC polypeptide variable region is encoded by a nucleic acid comprising the 3' two thirds of the OspC gene, about nucleotide 150 to about nucleotide 519 of an ospc gene (or about codon 50 to about codon 173). In another embodiment of the present invention, said OspC polypeptide variable region is encoded by a nucleic acid wherein the nucleic acid comprises, for example, nucleotide 244 to about nucleotide 519 (or about codon 81 to about codon 173), nucleic acid from about nucleotide 337 to about nucleotide 519 (or about codon 112 to about codon 173), nucleic acid from about nucleotide 418 to about nucleotide 519 (or about codon 139 to about codon 173), nucleic acid from about nucleotide 244 to about nucleotide 418 (or about codon 81 to about codon 139), nucleic acid from about nucleotide 337 to about nucleotide 418 (or about codon 112 to about codon 139), and nucleic acid from about nucleotide 150 to about nucleotide 243 (or about codon 50 to about codon 81) of an ospC gene.

In still another embodiment, the chimeric OspC polypeptides of the present invention comprises two or more polypeptides wherein a first polypeptide is from a first ospC gene from about nucleotide 26 (or about codon 8) to about nucleotide 630 (or about codon 210). In another embodiment, the first polypeptide is from about nucleotide 28. In another embodiment, the first polypeptide is from about nucleotide 53. In still another embodiment, the first polypeptide is from about nucleotide 55. In another embodiment, the first polypeptide is up to about nucleotide 621 of a first ospC gene. In still another embodiment, the first polypeptide is up to about nucleotide 582 of a first ospC gene. In still another embodiment, the first polypeptide is up to about nucleotide 576 of a first ospC gene.

The chimeric OspC of the present invention further comprises a second polypeptide, wherein the second polypeptide is derived from a second ospC gene from about nucleotide 28 (or about codon 9) to about nucleotide 571 (or about codon 190).

It is understood that the polypeptides than comprise the chimeric polypeptide can include extra nucleotides or fewer nucleotides from the given ospC gene from which the polypeptide is derived in order to simplify the construction of the gene encoding the chimeric polypeptide, e.g. to allow for the use of convenient restriction endonuclease sites or to allow the ligation of the gene fragments such that a contiguous coding region is created. Based on the guidance provided herein, one of ordinary skill in the art would readily be able to add or remove nucleotides from the termini of the gene fragments encoding the polypeptides of the chimeric OspC protein to generate chimeric proteins of the present invention with no or only routine experimentation. Furthermore, there can be an extra about 1 to about 10 amino acids on the N- and/or C-terminus of the polypeptides and chimeric proteins of the present invention and still retain the properties of the present invention.

The present invention also includes variants or altered versions of the OspC polypeptides and nucleic acids encoding said polypeptides. As used herein, a variant of a polynucleotide or polypeptide refers to a molecule that is substantially similar to either the entire molecule, or a fragment thereof. For example, when the molecule is a polypeptide, variant refers to an amino acid sequence that is altered by one or more amino acids, wherein either a biological function, structure or antigenicity of said sequence or combination thereof is maintained in the variant. The variant may have "conservative" changes, wherein a substituted amino acid has similar structural or chemical properties, e.g., replacement of leucine with isoleucine. Or a variant may have "nonconservative" changes, e.g., replacement of a glycine with a tryptophan. Similar minor variations may also include amino acid deletions or insertions, or both. Similarly, when the molecule is a polynucleotide, variant refers to a sequence that is altered by one or more nucleotides. The variant may have silent variations, wherein the change does not alter the amino acid encoded by the triplet comprising said variation or the variation is not silent, that is, alterations in encoded amino acids are generated.

As used herein, the term "altered version" refers to a polynucleotide sequence or a polypeptide sequence, wherein said sequence has one or more differences with a native or wildtype version of said sequence.

In another embodiment, the invention includes an isolated nucleic acid molecule comprising a nucleotide sequence which is homologous to one or more of the chimeric sequences of the present invention, or complements thereof. Such a nucleotide sequence exhibits at least about 80% homology, or sequence identity, with one of the chimeric OspC sequences, such that the encoded protein retains the antigenicity and immunogenicity of the unaltered chimeric protein. Preferably, the homologous sequences of the present invention shares at least about 90% homology or sequence identity with the corresponding unaltered chimeric ospC. Particularly preferred sequences have at least about 95% homology or have essentially the same sequence.

The altered nucleic acids and homologous nucleic acids of the present invention hybridize to the corresponding chimeric ospC under conditions of high stringency. A general description of stringency for hybridization conditions is provided by Ausubel, F. M., et al., *Current Protocols in Molecular Biology*, Greene Publishing Assoc. and Wiley-Interscience 1987, & Supp. 49, 2000. Factors such as probe length, base composition, percent mismatch between the hybridizing sequences, temperature and ionic strength influence the stability of nucleic acid hybrids. Thus, stringency conditions, sufficient to allow hybridization of oligonucleotides to the template, can be varied by routine optimization to generate high stringency conditions.

Alternatively, conditions for stringency are as described in WO 98/40404, the teachings of which are incorporated herein by reference. In particular, examples of highly stringent, stringent, reduced and least stringent conditions are provided in WO 98/40404 in the Table on page 36. Examples of stringency conditions are shown in Table I below which is from WO98/40404 to Jacobs et al., highly stringent conditions are those that are at least as stringent as, for example, conditions A–F; stringent conditions are at least as stringent as, for example, conditions G–L; and reduced stringency conditions are at least as stringent as, for example, conditions M–R.

TABLE 1

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≧50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≧50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≧50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≧50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≧50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≧50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≧50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≧50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≧50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.

†SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.

*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(% G + C) − (600/N), where N is the number of bases in the hybrid, and [$Na^+$] is the concentration of sodium ions in the hybridization buffer ([$Na^+$] for 1xSSC = 0.165M).

As used herein, "isolated" refers to nucleic acid or polypeptide that has been removed from its original environment (e.g., the natural environment if it is naturally occurring). For example, polynucleotide or DNA or polypeptide, which is separated from some or all of the coexisting materials in the natural system. An isolated polynucleotide can be part of a vector and/or composition, and still be isolated in that the vector or composition is not part of its natural environment. Likewise polypeptides can be part of a composition and still be isolated in that the composition is not part of its natural environment.

The chimeric proteins of the present invention comprise OspC proteins or polypeptides as described above from two or more OspC families of Lyme disease causing *Borrelia* as described in Table II. In one embodiment of the present invention, said families comprise *Borrelia burgdorferi* OspC families A, B, I and K and *Borrelia afzelii* OspC families A and B. The chimeric proteins of the present invention comprise, for example, a first OspC polypeptide encoded by a nucleic acid comprising a sequence from about codon 18 to about codon 210 of a first ospC gene. In another embodiment, the sequence is from about codon 8. In another embodiment, the sequence is to about codon 207. In another embodiment, the sequence is to about codon 194. In still another embodiment, the sequence is to about codon 192. The chimeric proteins of the present invention further comprise, for example, a second OspC polypeptide comprising an OspC variable polypeptide encoded by nucleic acid fragments as described above. In another embodiment of the present invention, the chimeric protein comprises two or more OspC variable polypeptides as described above.

The chimeric proteins of the present invention further comprise, for example, a second OspC polypeptide encoded by a nucleic acid comprising a sequence from about codon 9 to about codon 190 of a second ospC gene.

For the chimeric proteins of the present invention, at least two of said OspC polypeptides or immunogenic fragments thereof are fused together in a single protein, a chimeric protein, encoded by a single nucleic acid, wherein no two adjacent polypeptides in said fusion protein are found in the same configuration in a naturally occurring OspC protein.

In still another embodiment, the OspC proteins or chimeric proteins of the present invention from *Borrelia burgdorferi* and *Borrelia afzelii* are combined in a composition.

The present invention is drawn to a method of detecting an immune response to Lyme Disease causing *Borrelia* in a host sample. The method comprises contacting the host sample with a composition comprising OspC polypeptides from Lyme disease causing strains of *Borrelia*, such that anti-OspC antibodies, if present, in said sample bind to said OspC polypeptides. In one embodiment, the composition comprises one or more OspC polypeptide or diagnostic fragment thereof from two *Borrelia burgdorferi* OspC families selected from the group consisting of A, B, I and K, excluding the composition consisting of two OspC proteins wherein one OspC protein is from OspC family A and the second OspC protein is from OspC family I. The antibodies that bind the OspC polypeptides of the composition are detected or measured; thereby detecting an immune response to Lyme disease causing *Borrelia*. In another embodiment, the composition comprises at least two *Borrelia* OspC polypeptides or diagnostic fragment thereof from two *Borrelia afzelii* OspC families selected from the group consisting of A and B. In still another embodiment, the composition comprises polypeptides from OspC from *Borrelia burgdorferi* and *Borrelia afzelii*. In still another embodiment, the composition comprises one or more polypeptides from each of *Borrelia burgdorferi* families A, B, I and K and *Borrelia afzelii* families A and B. The composition can also comprise one or more of the chimeric polypeptides of the present invention.

The present invention is also drawn to kits comprising one or more OspC polypeptides or OspC chimeric polypeptides or combinations thereof together with suitable buffers and antibody detection reagents for the detection or diagnosis of Lyme disease causing strain of *Borrelia*. In another embodiment, the kits comprise nucleic acid sufficiently homologous to the OspC polypeptides or OspC chimeric polypeptides to detect nucleic acid encoding ospC genes from Lyme disease causing strains of *Borrelia* together with reagents to detect positive hybridization to target DNA or reagents to specifically DNA, for example.

For the purposes of a detection kit, "homologous" refers to two or more sequences that share substantial similarity but are not identical. Two DNA sequences are "substantially similar" when at least about 95% (preferably at least about 98%) of the nucleotides match over a defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Ausubel et al., *Current Protocols in Molecular Biology*, John Wiley & Sons, Inc., New York; Sambrook et al., *Molecular Cloning: A Laboratory Manual*, Cold Spring Harbor Laboratory Press. For purposes of the present invention, amino acid sequences having, for example, greater than 90 percent similarity are considered substantially homologous.

The vaccine compositions of the present invention elicit humoral and cell mediated immune responses in a host. Furthermore, the diagnostic compositions of the present invention are capable of detecting both humoral and cell mediated immune response from a host sample using standard immunodiagnostic techniques.

EXEMPLIFICATION

Example 1

Techniques

*Borrelia* Strains

One hundred and forty *B. burgdorferi* strains were isolated from primary erythema migrans (EM) lesions, blood or cerebrospinal fluid (CSF) of patients seen at the Lyme Disease Center at Stony Brook, New York, Lyme Disease Diagnostic Center at New York Medical College, Valhalla, New York or the private practices of the two collaborating physicians on the eastern end of Long Island or were obtained from the Centers for Disease Control (CDC). All patients met the Centers for Disease Control surveillance definition for Lyme Disease (CDC, *Morb. Mortal. Wkly. Rep.* 46:20–21, (1997)). Isolates from skin, blood and CSF were obtained using standard techniques (Barbour, A.G., Yale J. Biol. Med. 57:521–525, 1984; Berger, B. W. et al., *J. Clin. Microbiol.* 30:359–361, 1992; Wormser, G. P. et al., *J. Clin. Microbiol.* 36:296–298, (1998)). Punch biopsies were taken from the advancing border of the erythema migrans lesion and incubated in BSK-H medium (Sigma, St. Louis, Mo.) at 34° C. to create a culture. There was little culture bias as determined by direct analysis of biopsy tissue compared to culture isolates (Seinost, G. et al., *Arch. Derm.*, 135:1329–1333, (1999)), unlike isolation of *B. burgdorferi* from unfed ticks (Norris, D. E. et al., *J. Clin. Microbiol.* 35:2359–2364, (1997)). In addition, twenty-two *B. burgdorferi* sensu stricto ospC sequences were retrieved from GenBank. The tick data used was either from GenBank or from the study of Wang et al. (Wang, I-N. et al., *Genetics* 151:15–30 (1999)).

DNA Isolation

For isolation of genomic *Borrelia* DNA, log phase cells were harvested by centrifugation at 10,000 RPM for 30 minutes at 4° C. The bacterial pellet was resuspended in Tris/saline-buffer (10 mM Tris (pH 7.5), 150 mM NaCl). The bacteria were then pelleted and resuspended in TNE (10 mM Tris (pH 7.5) 150 mM NaCl, 1 mM EDTA). Freshly prepared lysozyme (20 mg/ml in TNE), sodium dodecyl sulfate (10%) and proteinase K (20 mg/ml) were added and the mixture was incubated at 50° C. for one hour, followed by RNAse treatment. DNA was extracted with phenol/chloroform, precipitated with ethanol and resuspended in TE buffer.

Polymerase Chain Reaction

The ospC gene was amplified using PCR, as described previously (Wang, I-N. et al., *Genetics* 151:15–30 (1999)). The OspC gene was amplified using two external primers: 5'-AAA GAA TAC ATT AAG TGC GAT ATT-3' (+), SEQ ID NO: 1, beginning at base 6; and 5'-GGG CTT GTA AGC TCT TTA ACT G-3' (−), SEQ ID NO: 4, ending at base 602. The 5' half of ospC was amplified using SEQ ID NO: 1 and the reverse primer, 5'-CAA TCC ACT TAA TTT TTG TGT TAT TAG-3' (−) SEQ ID NO: 2; ending at base 345. The 3' half of ospC was amplified using the primer, 5'-TTG TTA GCA GGA GCT TAT GCA ATA TC-3' (+), SEQ ID NO: 3, beginning at base 289, and SEQ ID NO: 4 as the reverse primer. The external primers amplified a 597 bp fragment. Amplification of the 5' half produced a 340 bp fragment while amplification of the 3' half produced a 314 bp fragment. All the base numbers and amplified fragment sizes are based on ospC sequence of strain B31 (GenBank accession number U01894), with start codon as base 1.

Amplification was conducted in 50 µl of a solution containing Perkin-Elmer Cetus 10× PCR buffer (100 mM Tris-HCl (pH 8.3), 500 mM KCl), 2.5 mM $MgCl_2$, deoxynucleoside triphosphates at 0.2 mM per nucleotide, 2.5 U of Taq polymerase (Perkin-Elmer/Cetus) and 0.5 µM of each primer. The amplification reaction was carried out for forty cycles in a DNA thermal-cycler (PTC-100; MJ Research, Inc., Watertown, Mass.) with an amplification profile of: denaturation at 95° C. for 40 seconds, annealing at 54° C. for 35 seconds, and extension at 72° C. for 1 min, after an initial denaturation step at 96° C. for 2 min. Negative controls were included in each experiment to control for contamination.

Cold SSCP-Analysis.

SSCP analysis was chosen to characterize genetic variation of the isolated ospC gene fragments based on its exquisitely high detection rate of DNA polymorphisms and point mutations at a variety of positions in DNA fragments (Orita, M. et al., *Proc. Natl. Acad. Sci.* 862766–2770, (1989)). Single point mutations have been detected in fragments up to 800 bp long (Michaud, J. et al., *Genomics*. 13:389–394, (1992)). However, there is evidence that the ability of SSCP analysis to detect mutations begins to decline significantly as PCR fragments approach 400 bp in size (Hayashi, K., *PCR Methods & Applications* 1:34–38, (1991)). Therefore, in order to achieve high efficiency of detection of nucleotide polymorphism, the length of the PCR products used herein was 340 bp from the 5' half and 314 bp from the 3' half of ospC.

Amplified ospC gene fragments from all one hundred and forty strains were analyzed for genetic variations by the cold SSCP protocol described by Hongyo et al. (Hongyo, T. et al., *Nucleic. Acids Res.* 21:3637–3642, (1993)). Briefly, 5 to 15 µl of the PCR product was added to a mixture containing 4 µl 5× TBE Ficoll sample Buffer (NOVEX, San Diego, Calif.) and 0.4 µl 1 µM methylmercury hydroxide (Alfa Aesaer, Ward Hill, Mass.). The amount of the PCR product used for the SSCP analysis was estimated after visualizing the PCR product on an agarose gel with ethidium bromide. The sample mixture was heated to 95° C. for 4 min, then chilled on ice prior to loading the entire 20 µl into the gel sample well. The sharpest bands were observed when the sample was applied to a pre-cast 20% TBE gel (NOVEX) electrophoresis system (ThermoFlow ETC Unit, NOVEX) with 1.25× TBE running buffer. Electrophoresis of SSCP products was conducted at a constant temperature of 8° C. for 17 h at 240 volts in order to reveal discernable mobility shifts. Gels were stained with 0.5 µl/ml ethidium bromide in 1× TBE buffer for 25 min and destained in distilled water for 30 min. Stained bands were viewed using a 340 nm UV staining box. Samples that showed more than two SSCP bands were reamplified to determine whether the bands found were real alleles or the product of PCR artifacts. Side-by-side SSCP analysis was performed in order to detect even slight shifts in electrophoretic mobility.

DNA Sequencing

The ospC gene or representatives of each mobility class were reamplified. Double-stranded PCR fragments were purified by agarose gel electrophoresis and subjected to automated DNA sequencing using fluorescent dideoxy terminator chemistry and the forward and reverse primers originally used for PCR amplification.

Statistical Analysis

Chi square analysis of contingency tables was performed. This analysis tests for significant difference in frequency distributions. The tables were 2×N where N is the number of major ospC groups distinguished. The average expected number in each element of the table needs to be about six or greater for an unbiased test (Zar, J. H., *Biostatistical Analysis*, 3rd ed, p. 206, (1996)). This means that the number of observations should be greater than 6 times 2N. When the expected average number was less than six, the major ospC groups with the lowest number in the sample were combined until the number of observations were about equal to or greater than 12N.

Results ospC Mobility Classes in Human *B. burgdorferi* Isolates.

One hundred and thirty-two isolates of *B. burgdorferi* sensu stricto from patient samples of skin, blood, and CSF (Table II) were propagated in vitro and used as a source of DNA for analysis. The ospC genotype of each strain was determined by cold SSCP analysis of the 5' end (340 bp) of the gene and was confirmed by SSCP analysis of the 3' end (314 bp) of ospC. In all *B. burgdorferi* isolates, the genetic variation at the 5' end of the gene corresponded to the variation at the 3' end. At least two representatives of each SSCP mobility class were subsequently sequenced. The sequences of the same mobility classes were identical in all samples and each mobility class had a unique sequence. Therefore, the sensitivity and specificity of SSCP analysis was 100%. Each SSCP mobility class was designated as an allele. Wang et al. recently described 13 ospC alleles (Wang, I-N. et al., *Genetics* 151:15–30). An additional five ospC (OC) mobility classes, OC14–18 are described herein. OC14 has the same ospC sequence as the ospC in strain 2591.

TABLE II

Alignment of major ospC groups with ospC alleles identified by SSCP analysis

| Major ospC Group | ospC allele (SSCP) | GenBank number[1] | Ticks | Skin[2] | Disseminated[2] |
|---|---|---|---|---|---|
| A | 1 | AF029860 | 17 | 23 | 21 |
| B | 2 | AF029861 | 17 | 19 | 4 |
| C | 3 | AF029862 | 11 | 3 | 0 |
| D | 4 | AF029863 | 10 | 1 | 0 |

TABLE II-continued

Alignment of major ospC groups with ospC alleles identified by SSCP analysis

| Major ospC Group | ospC allele (SSCP) | GenBank number[1] | Ticks | Skin[2] | Disseminated[2] |
|---|---|---|---|---|---|
| E | 5, 7 | AF029864 | 6 | 1 | 0 |
| F | 6 | AF029865 | 9 | 0 | 0 |
| G | 8 | AF029867 | 5 | 7 | 0 |
| H | 9 | AF029868 | 7 | 6 | 0 |
| I | 10 | AF029869 | 1 | 9 | 3 |
| J | 11, 18 | AF029870 | 3 | 7 | 0 |
| K | 12, 13 | AF029871 | 6 | 32 | 16 |
| L | — | L42899 | 2 | 0 | 0 |
| M | 14 | U01892 | 1 | 3 | 0 |
| N | 15 | L42899 | 1 | 3 | 0 |
| O | — | X84778 | 0 | 1 | 0 |
| P | — | U91796 | 1 | 0 | 0 |
| Q | — | U91790 | 1 | 0 | 0 |
| R | — | U91791 | 2 | 0 | 0 |
| S | — | U91793 | 1 | 0 | 0 |
| T | 16 | AF065143 | 0 | 1 | 0 |
| U | 17 | AF065144 | 0 | 2 | 0 |

[1]A single GenBank sequence of each type is given as an example.
[2]The number of each major ospC group observed in blood, synovial fluid or cerebrospinal fluid. This includes both SSCP data and data from the literature, including GenBank.
*B. burgdorferi sensu stricto Groups P through S are only found in Europe. Groups R and S are excluded from the analysis because nearly identical ospC alleles are found in B. afzelii and B. garinii, showing these groups were recently created by cross-species transfer.

Multiple Infections

Of the one hundred and thirty-two primary isolates from patients with Lyme disease in this study, most contained only a single strain. Seven skin isolates and one CSF isolate contained two different strains as determined by SSCP analysis, thus giving a total of one hundred and forty different strains. The ospC allele pairs found in multiply infected erythema migrans biopsy specimens were (OC1, OC12), (OC1, OC14), 2×(OC2, OC3), 2×(OC2, OC12), and (OC8, OC18). CSF isolate NY940657 contained ospC alleles OC1 and OC12. For CSF isolate 297, which was isolated in Connecticut, there were two ospC sequences published in GenBank: L42893 (SEQ ID NO:85), which is analogous to OC10 and U08284 (SE ID NO:86), which is analogous to OC12. The pair-wise difference of ospC sequences of both strains is 16.4%, suggesting CNS infection with two different strains in this isolate. Overall, 5.5% of all isolates described herein contained two strains. Because as many as 50% of ticks isolated in the wild are infected with multiple strains, exposure to multiple strains in a single tick bite is common, raising the possibility that different strains are differentially pathogenic.

To these one hundred forty strains for which the ospC allele was determined herein, twenty-two strains of known ospC sequence from GenBank were added to give a total of one hundred sixty-two. Fifty-one of these strains were obtained either from eastern Long Island; seventy-seven were obtained from Westchester County, New York, and the remainder from other endemic areas in the United States (twenty-two strains) and Europe (twelve strains). The isolates were divided into those from the site of the primary infection, the erythema migrans skin lesion (one hundred eighteen isolates), and those from secondary sites, where the infection had disseminated (forty-four isolates). This later group included, for example, twenty from cerebro-spinal fluid (CSF), twenty-three from blood, and one from synovial fluid.

Major ospC Groups in Human B. burgdorferi Isolates

Surprisingly, as described herein, the differences between ospC sequences among and between the families of B. burgdorferi sensu stricto fell into two groups. Pairs of ospc genes within the same family differed in nucleic acid sequence by less than two percent while pairs of ospC genes from separate families in nucleic acid sequence differed by more than eight percent. Wang et al., defined nineteen major ospC groups, designated A to S (Wang, I-N. et al., *Genetics* 151:15–30 (1999)). As described herein, two additional ospC groups are provided, designated T and U. OC16 represents major group T and OC17 represents major group U (Table I). The lowest pair-wise differences of group T and U to any other major ospC group are 16.1% and 20.5% respectively.

B. burgdorferi Clones are Differentially Pathogenic

As described herein, clones representing different ospC groups of *Borrelia burgdorferi* are differentially pathogenic. This is demonstrated by the differing frequencies of the various major ospC groups in ticks, in the initial infection in the skin, and in disseminated infections.

The strains in GenBank and the literature for which the ospC sequences have been determined were widely sampled from the entire geographic range of the species and were chosen irrespective of whether they were from ticks or humans. These strains gave a small but random sample of the frequencies of the major ospC groups in ticks and humans. As demonstrated herein, the frequency of the major ospc groups from human isolates was found to be significantly different from the frequency found in ticks on Long Island. Table III shows that the frequency distribution of strains from skin from eastern Long Island differ significantly from tick strains collected in the same area.

TABLE III

| | Major ospC groups | | | | | | | | | |
|---|---|---|---|---|---|---|---|---|---|---|
| Isolates From | A | B | C | D | F | G | H | I | K | Comb.[a] |
| Erythema migrans lesions (N = 46) | 13 | 6 | 2 | 0 | 0 | 1 | 0 | 4 | 16 | 4 |
| Ixodes scapularis ticks (N = 74) | 12 | 12 | 11 | 9 | 6 | 5 | 7 | 1 | 5 | 6 |

$\chi^2$ = 36.3 with 9 degrees of freedom
p < 0.001
[a]Combined major groups are defined by individual frequencies of 0.025 or less and include groups E, J, N, O.

The analysis provided herein of all ospc groups presented in this study showed that most groups are found in both ticks and in humans (Table II). However, major groups A, B, I and K predominated in humans, with A and K groups found most frequently. (FIG. 1).

The pattern of pathogenicity of the various clones as demonstrated by frequency in the primary site of infection, the skin, compared to the frequency in secondary sites revealed that only four major groups (A, B, I and K) were found in both the skin and secondary sites (compare Tables III an IV). All other major groups were found only in the skin. When all groups with three or fewer isolates are combined to give the combined group of Table IV, a 2 by 8 contingency test comparing the frequency distribution of skin versus secondary sites gives a significance of p<0.005. When no groups are combined, a 2 by 15 contingency test is still significant ($X^2$=24.07 with 14 degrees of freedom, p<0.05). The distribution of strains from primary and secondary sites indicated that only a certain of the major groups, A, B, I, and K cause disseminated disease. As described herein, these are referred to as invasive clones whereas other clones are referred to as non-invasive clones.

TABLE IV

| Isolates From | Major ospC groups | | | | | | | |
|---|---|---|---|---|---|---|---|---|
| | A | B | G | H | I | J | K | Comb.[a] |
| Erythema migrans lesions (N = 118) | 23 | 19 | 7 | 6 | 9 | 7 | 32 | 16 |
| Disseminated Infections (N = 44) | 21 | 4 | 0 | 0 | 3 | 0 | 16 | 0 |

$\chi^2$ = 23.6 with 7 degrees of freedom
p < 0.005
[a]Combined major groups are defined by individual frequencies of 0.025 or less and include groups C, D, E, M, N, O, T and U.

As described herein, the different clones of *B. burgdorferi* sensu stricto, as defined by ospC groups, are differentially pathogenic. Some groups very rarely, if ever, cause human disease, e.g. ospC groups D, E, F, and L. Some groups cause a local infection at the tick bite site, but not systemic disease, e.g. ospc groups G, H, J, and T. Finally, there are some groups which are responsible for systemic disease; these are ospC groups A, B, I, and K. Our findings indicate that all systemic *B. burgdorferi* sensu stricto infections in humans are caused by strains in these four ospC groups.

FIG. 1 shows the frequency distribution of major ospC groups among *B. burgdorferi* isolates from Eastern Long Island *Ixodes scapularis* ticks, n=72, (A); erythema migrans lesions, n=118, (B); and secondary sites of infection, n=44, (C). The percentage of group A plus K increased from 23% in the tick isolates, to 47% in the skin isolates, and to 84% in the secondary sites. The length of the bars in FIG. 1 reflect this increase, by holding the length of the combined A and K groups constant. In the skin, groups C, D, E, M, N, O, T and U have been combined since their individual frequencies are 0.025 or less. This combination of groups when combined make up 12.7% of the total number of strains.

A similar analysis was conducted for *Borrelia afzelii*. The analysis included OspC alleles from 21 strains from GenBank and 12 strains sequenced for this study. These sequences fell into 20 major groups where the definition of a group is less that 1% sequence diversity within a group and at least 7.7% sequence difference between groups. There were two exceptions to this rule which were caused by a deletion in one ospC gene and a cross-species transfer of a small section of DNA in another ospC gene. When these anomalous sections were removed, all ospC alleles fell into 20 groups. Only two groups contained strains from chronic infections—groups A and B. By analogy and the *B. burgdorferi* study, it appears that only two groups are pathogenic in *B. afzelii*.

Example 2

Protein Expression and Immunoblot

Protein Expression

The *Escherichia coli* (strain BL21 (pLysS) or strain B834 (DE3)) were transformed with the plasmid encoding the recombinant chimeric *Borrelia* proteins (RCBPs), and grown in 10 ml LB media (5 g/l NaCl, 10 g/l tryptone, 5 g/l yeast extract, 25 mg/l chloramphenicol and 50 mg/l ampicillin) at 37° C., with shaking. When the optical density at 600λ reached 0.3–0.4 units, recombinant protein expression was induced by adding IPTG (isopropyl B-D-thiogalactopyranoside) to a final concentration of 0.5 mM and the cells were grown for an additional three hours. The cultures were harvested by centrifugation at 3800× g for five minutes. The cells were resuspended in 20 mM $NaPO_4$, pH7.7 and stored at −20° C. overnight. Once thawed, the crude extracts were incubated with DNase (2 µg/ml) in the presence of 2.5 mM of $MgCl_2$ at room temperature for thirty minutes, spun at 14000 rpm (Eppendorf 5417C) for five minutes and 5 µl of the protein sample was run on a SDS-PAGE which was either stained in Commassie Blue or used for Immunoblot. Protein samples were solubilized, usually with a sodium dodecyl sulphate (SDS) containing buffer and in selected cases with reducing agents such as dithiothreitol (DTT) or 2-mercaptoethanol (2-ME). Following solubilization, the material was separated by SDS-PAGE. The proteins were then eletrophoretically transferred to a polyvinylidene difluoride membrane (PVDF, Immobilon-P®, Millipore). The transfer of proteins was monitored by a reversible staining procedure, Ponceau S. The stained membrane was made and the membrane destained by soaking in water for 10 minutes. All non-specific binding sites in the proteins and on the membrane were blocked by immersing the membrane in a solution containing a protein or detergent blocking agent (5% milk in tris-buffered saline (TBS) Tween-20® 0.1%). The membranes were then incubated with primary antibody (either a monoclonal antibody or Erythema Migrans Lyme disease human serum). The membrane was washed and the antibody-antigen complexes were identified using alkaline phosphatase (AP) enzymes coupled to secondary antibody, either anti-immunoglobulin G (anti-mouse IgG) to detect the monoclonal antibody or anti-human IgA+IgG+IgM to detect the serum antibodies. A chromogenic substrate for alkaline phosphatase was then used to visualize the activity.

Example 3

Serologic Characterization—ELISA
(Enzyme-Linked Immunosorbent Assay)

Immobilization of RCBPs onto ELISA Plates, Determining Optimal RCBP Binding:

A solution of purified RCBPs in sodium phosphate buffer, pH 9.0 was used to oat commercial microwell plates (MaxiSorp®, Nunc). Recombinant OspC *Borrelia* proteins are described in Table V. The coating procedure was as follows: 100 µl of a solution containing the appropriate concentration of each RCBP was added to each well and the microwell plate was incubated for either one hour at room temperature or at 4° C. overnight. The antigen solution was removed from the wells, the plate washed three times with phosphate buffered saline (PBS) pH 9.0, and 200 µl of blocking solution added (2% BSA fraction V (Sigma) in PBS). Following a thirty minute incubation at 37° C., the plates were washed three times with PBS, wrapped in plastic and stored at 4° C. until used. The binding of the individual RCBPs was measured using monoclonal antibodies specific for either OspA or OspC followed (after washing) by an alkaline phosphatase-conjugated goat anti-mouse secondary antibody. The upper limit of protein binding was found to be beyond the working range of the monoclonal antibody used to measure it, and the standard blocking protocol was found to successfully saturate this high protein binding capacity, leaving low background readings in the control wells. The results of these experiments indicated that a protein concentration of 0.5 µg/ml in the coating buffer was optimal for each of the RCBP tested. It was not found to be necessary that the chimeric proteins be immobilized in a specific molar ratio to one another; only that enough of each protein be bound so that epitopes in that chimeric protein do not become limiting in subsequent ELISA assays using patient serum. For practical purposes, it was found that these conditions were met when the monoclonal-capture assay reached an absorbance of about 1.5 units or greater for each mouse monoclonal antibody, with a specific epitope represented in one of the chimeric proteins on the well surface. If necessary, however, the concentrations of individual proteins in the mixture can be adjusted to achieve the desired levels of immobilized protein using routine optimization. Although the amount of each RCBP bound to the surface of the well and the amount of any one epitope exposed to the solution varies somewhat from protein to protein, the amount of bound epitope was not found to be limiting within the useful range of the ELISA.

ELISA Tests:

The standard procedure for the ELISA tests was as follows: human serum samples were diluted 1:100 in specimen diluent (10% fetal bovine serum in PBS pH 9.0) and 100 μl of each sample added to ELISA plate microwells that had been coated with antigen as described above. Following incubation for 1 hour at 37° C., the samples were removed and the plates washed three times in TBS-Tween™ (0.5 M Tris pH 7.2; 1.5 M NaCl; 0.5% Tween™). Goat anti-human antisera conjugated to alkaline phosphatase specific for either IgM (Fc) or IgG (Fab), (Jackson Immuno Research Laboratories) was diluted 1:1000 in PBS, pH 7.4 and 100 μl of the solution added to each well. Following incubation for thirty minutes at 37° C., the plates were washed three times with TBS-Tween™ and 100 μl of substrate solution (5 mg of p-nitrophenylphosphate tablets dissolved in 1× diethanolamine substrate buffer to yield a 2 mg/ml solution—Kirkegaard Perry Laboratory) was added to each well. The plates were incubated for thirty minutes at 37° C. and 100 μl of stop solution (5% EDTA) was added to each well. The absorbance at 410 nm was read on a microplate reader (Dynatech). A sample was considered positive if it produced an average absorbance greater than the mean of the negative controls plus three standard deviations. Cross-reactivity was measured against serum from patients with syphilis, systemic lupus erythematosus, rheumatoid arthritis as well as endemic field workers and non-endemic field worker.

Using the above-described ELISA test, serum from various patients was tested. Patients with Erythema Migrans Acute (EMA) had early, localized infections, typified by the presence of well-defined erythemamigvans (EM) in patients from an endemic area. Patients with Early Disseminated (EA), are Acute Disseminated (AcD) infections were typified by EM and one of the following: additional EM lesions, AV block, neurological abnormalities (e.g., seventh nerve pasly), or meningitis. Patients with Acute Convalescent (AcC) were obtained from the same patients as EA and AcD, 2–4 weeks later. Serum was also tested from the CDC from patients with well documented Syphilis (S), serum was also obtained from SUNY at Stony Brook, Division of Rheumatology from patients with well documented systemic Lupus Erythematosus (SLE) or patients with well documented Rheumatoid Arthritis (RA). Endemic field worker sera (End), were obtained from outdoor workers from Long Island, which is endemic for Lyme disease. Non-endemic sera (Nedn) were obtained from outdoor workers from Arizona, which is not endemic for Lyme disease. In addition, serum was tested from endemic field workers (End) and non-endemic field workers (NEnd). Polypeptides of the present invention were used to test these various sera as summarized in FIG. 8.

TABLE V

| Polypeptide | SEQ ID NO.:* (DNA) | SEQ ID NO: (POLYPEPTIDE) |
|---|---|---|
| C[[1]] 2 unlipidated | 5 | 6 |
| C[[2]] 5 unlipidated | 7 | 8 |
| [1]C1 | 9 | 10 |
| C2 | 11 | 12 |
| C5 | 13 | 14 |
| C7 | 15 | 16 |
| C10 | 17 | 18 |
| C11 | 19 | 20 |
| C12 | 21 | 22 |
| C1C10[2] | 23 | 24 |
| C1C12 | 25 | 26 |
| B31C10[3] | 27 | 28 |
| B31C12 | 29 | 30 |
| C2C7 | 31 | 32 |
| C2C10 | 33 | 34 |
| C2C12 | 35 | 36 |
| C5C7 | 37 | 38 |
| C5C10 | 39 | 40 |
| C5C12 | 41 | 42 |

Example 4

Mice Immunization with OSPC Chimeric Proteins as Immunogen

Female BALB/c mice, four-five weeks old, were immunized with 5 μg of OspC chimeric proteins in 100 μl of aluminum hydroxide adjuvant by SC (subcutaneous) injection. Five mice were used for each group. For the negative control, five female BALB/c mice were immunized with 100 μl of aluminum hydroxide adjuvant only. Two weeks after immunization, the mice received a boost with the same antigen and two weeks after that an equal boost was administered. One week after each boost, blood was drawn from each mouse (including negative controls) and the serum was tested, using the ELISA method described above, for the presence of the respective anti-OspC chimeric protein antibodies.

Mice were immunized with chimeric proteins as follows in Table VI.

TABLE VI

| Immunogen | SEQ ID NO.: (polypeptide) | OspC Family |
|---|---|---|
| LipCB31[1] | 44 (DNA 43) | A |
| LipC12[2] | 22 (DNA 21) | K |
| UnlipC2[3] | 8 | B |
| UnlipC2C7[4] | 32 | B/E |
| UnlipC2C10 | 34 | B/I |
| UnlipC2C12 | 36 | B/K |
| UnlipC5C10 | 40 | E/I |
| UnlipC5C12 | 42 | E/K |

[1]"Lip" means lipidated N-terminus, Lip CB31 is OspC protein from *B. burgdorferi* strain B31.
[2]The number immediately after "C" refers to the particular allele of OspC as described herein.
[3]"Unlip" means the unlipidated form of the N-terminus.

Figure 2:
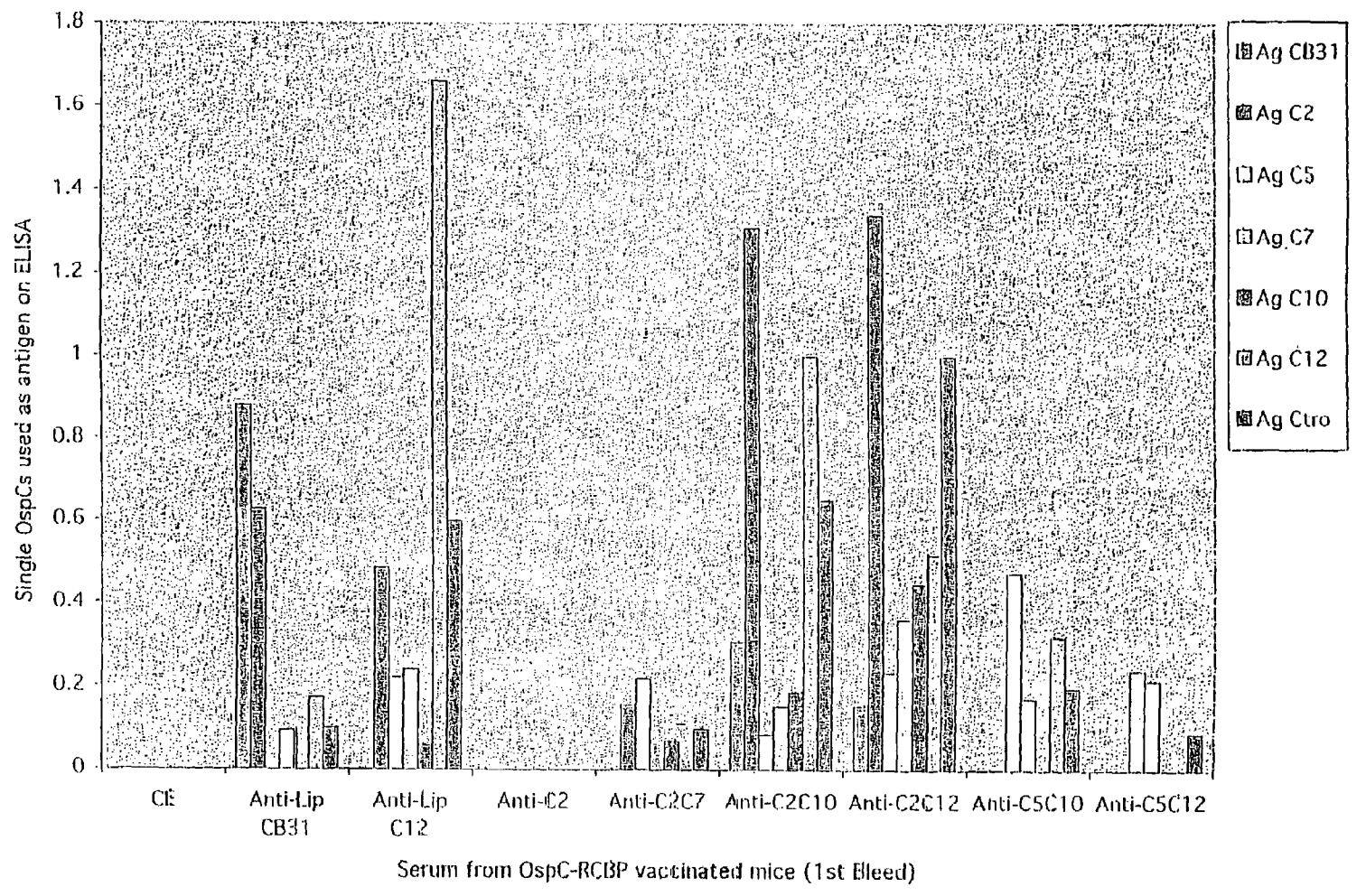
Figure 3:
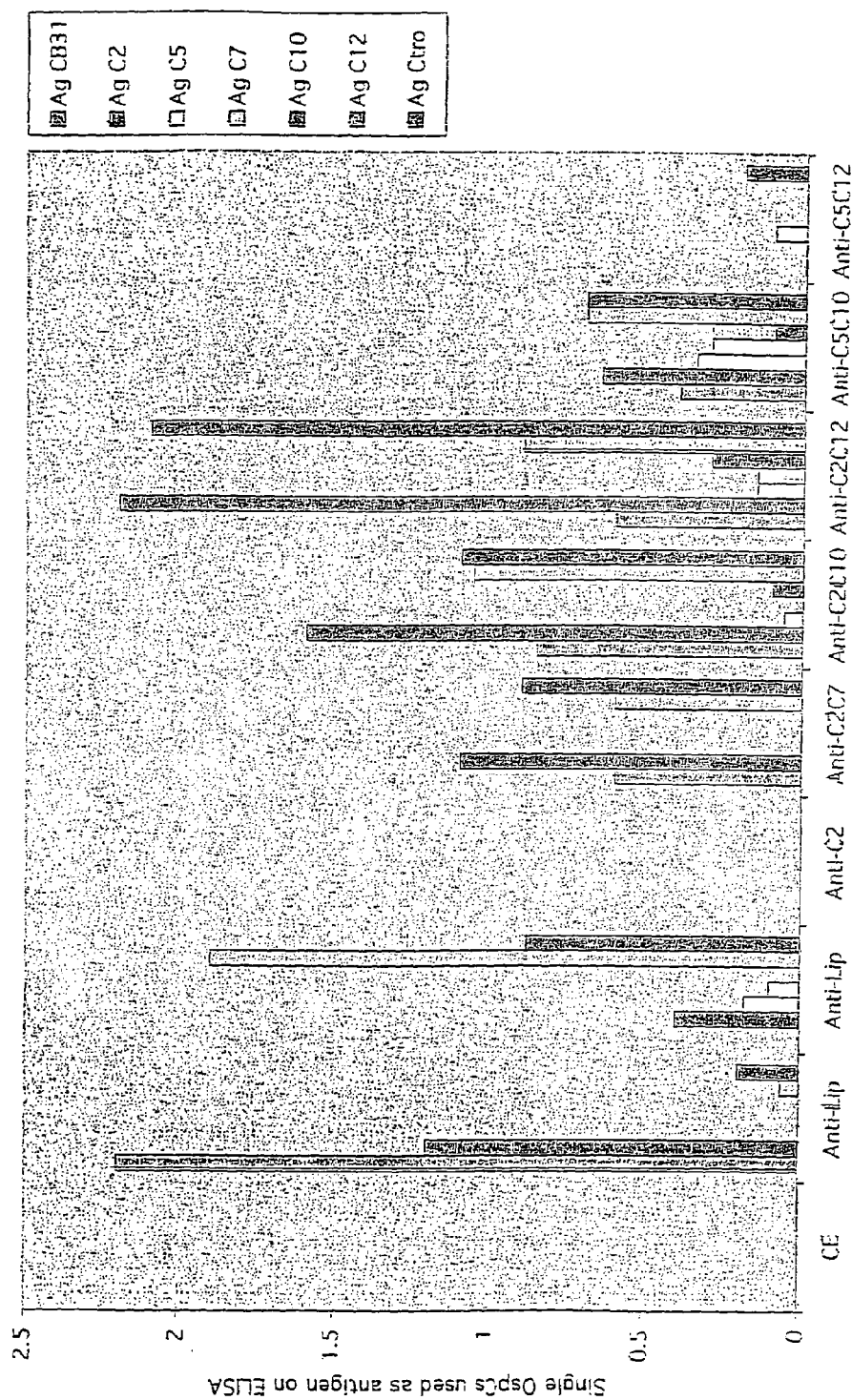
FIG. 3 is a bar graph showing the reactivity of serum from mice immunized with the indicated Borrelia protein or recombinant chimeric Borrelia protein (X-axis) against the indicated OspC antigens (legend) where the serum is from the second bleed.

Several types of single OspCs from *B. burgdorferi* sensu stricto, OspCB31, OspC2, OspC5, OspC7, OspC10, OspC12 and a single OspC from *B. afzelii*, Ctro, were used as the antigens in an ELISA to test the serum collected from the immunized mice. As shown in FIGS. 2 and 3, unlipC2C10 and unlipC2C12 elicited an immune response in the form of antibodies, (a humoral response) against a broad range of ospC families, after the first and second bleeds, respectively. The serum from unlipC2C10, unlipC2C12, LipCB31 and LipC12 immunized mice was then used to test against single OspC polypeptides from several strains of the three major Borrelia gene species Borrelia burgdorferi, Borrelia afzelii and Borrelia garinii.

Figure 4:
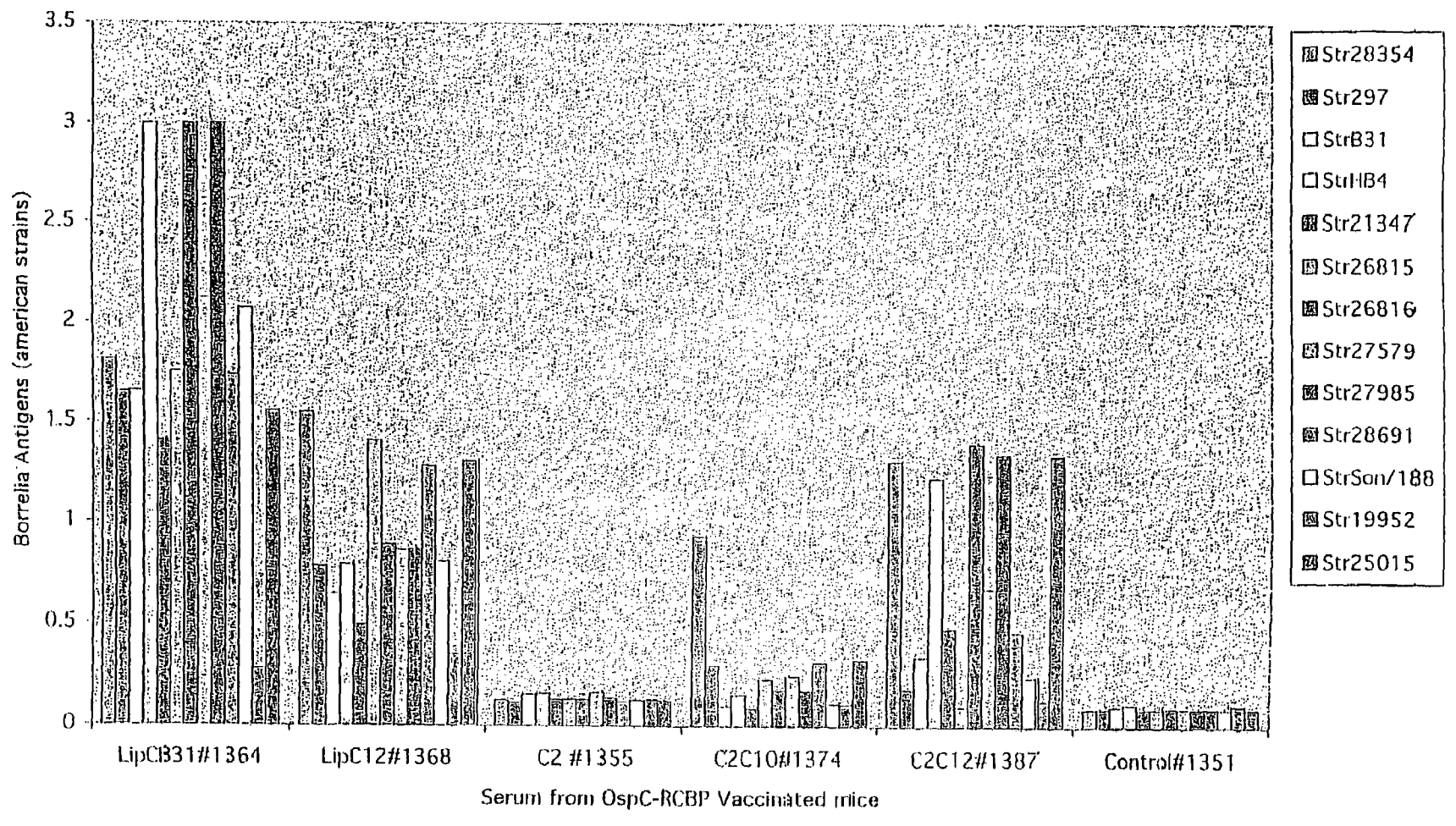

As shown in FIG. 4, 13 different strains of B. burgdorferi sensu stricto (B.b.s.s.) were tested for reactivity with the above described sera. Sera from mice immunized with both LipCB31 and LipC12, which were the gold standard of this experiment, detected 12/13 of the B.b.s.s. strains tested. Sera from mice immunized with unlipidated C2C12 detected 8/13 of the strains tested. Use of unlipidated forms of these proteins as vaccine immunogens or diagnostic antigens is desirable because the product yield by the expression vector is much greater and the proteins are much easier to purify. These two reasons alone made the production of these proteins less expensive.

Figure 5:
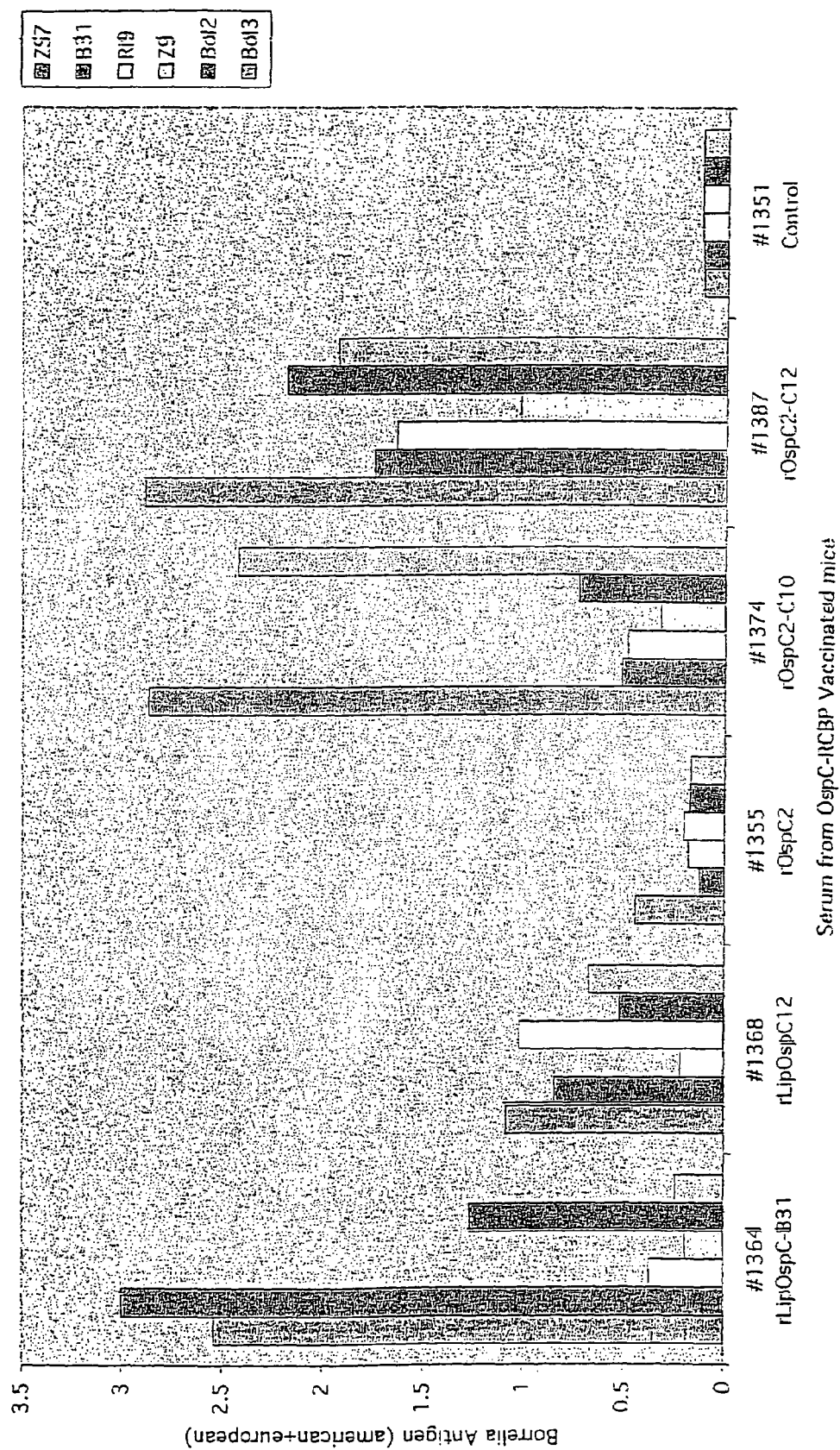
FIG. 5 is a bar graph showing the reactivity of serum from mice immunized with the indicated Borrelia protein or chimeric recombinant Borrelia protein (X-axis) against the indicated strains of Borrelia burgdorferi sensu lato (legend).

As shown in FIG. 5, chimeric proteins unlipC2C10 and unlipC2C12 of the present invention elicited an immune response that detected 5/6 and 6/6 of the strains tested, as compared to the gold standard lipidated proteins LipC12 and LipCB31, which detected 5/6 and 3/6 of the strains, respectively. When compared to the parental unlipidated OspC2 (rOspC2), the chimeric proteins unlipC2C10 and unlipC2C12 elicited an immune response and detected more strains than the gold standard ((0/6) versus (5/6) and (6/6) respectively). This result was unforeseen and unexpected.

Figure 6:
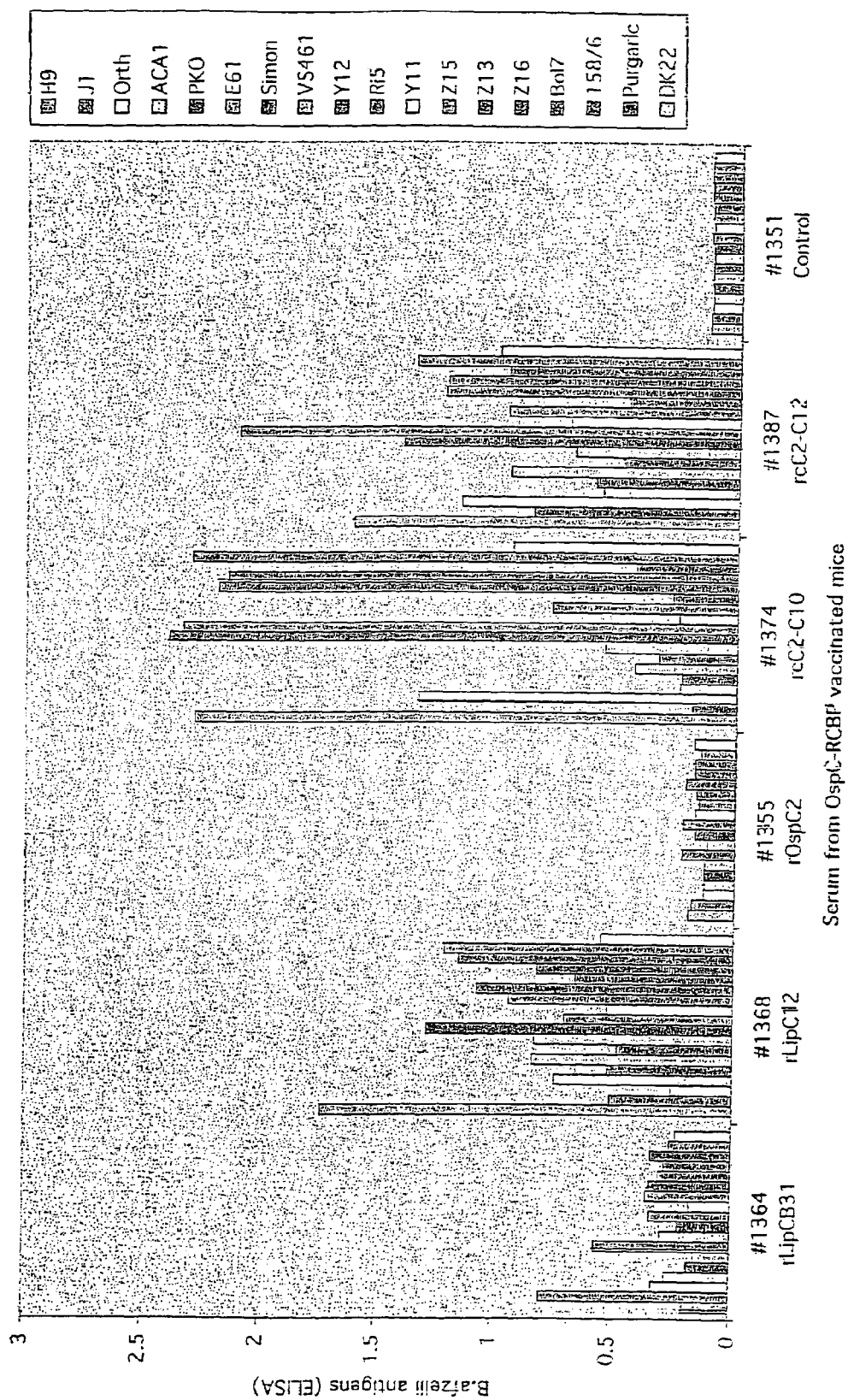
FIG. 6 is bar graph showing the reactivity of serum from mice immunized with the indicated Borrelia protein or chimeric recombinant Borrelia protein (X-axis) against the indicated strains of Borrelia afzelii (legend).
Figure 7:
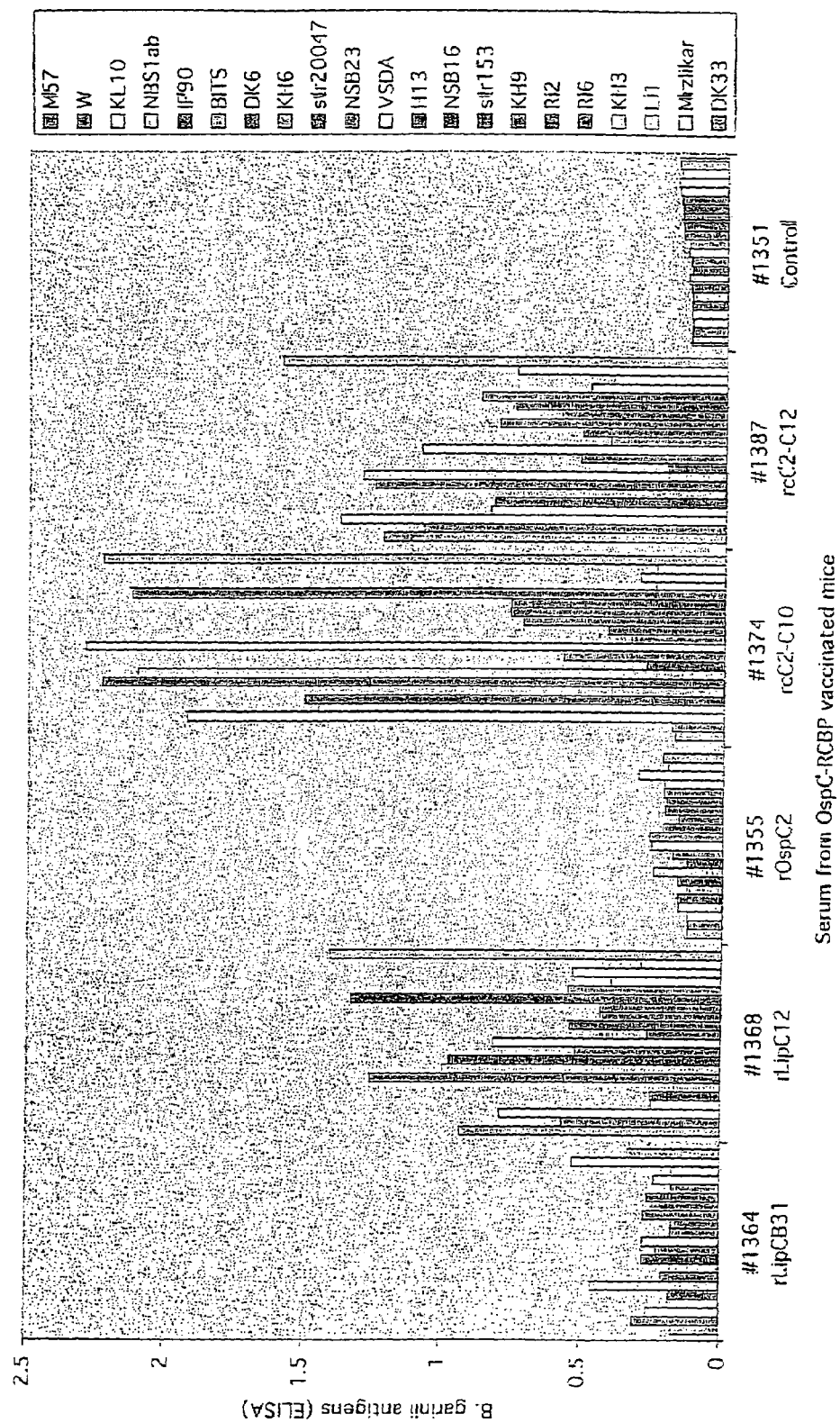
FIG. 7 is bar graph showing the reactivity of serum from mice immunized with the indicated Borrelia protein or chimeric recombinant Borrelia protein (X-axis) against the indicated strains of Borrelia garinii (legend).

In another experiment, as shown in FIGS. 6 and 7, chimeric proteins of the present invention elicited a significant immune response across all the 18 different strains of B. afzelii (FIG. 6) and all the 21 different strains of B. garinii (FIG. 7). For example, the chimeras unlipC2C10 and unlipC2C12 detected 12 and 18 of the 18 strains of B. afzelii, respectively, as compared to 0/18 detected by the parental unlipidated C2. The same chimeras detected 14 and 20 of the 21 strains of B. garinii, respectively, as compared to 0/21 detected by the parental unlipidated C2. Furthermore, the gold standards LipCB31 and LipC12 detected 2 and 17 of the 18 strains of B. afzelii, respectively, and 2 and 15 of the 21 strains of B. garinii. These results indicate that, unlike the LipOspCB31, LipOspC12 and unlipOspC2, the unlipidated C2C10 and unlipidated C2C12 used as immunogens elicited a significant immune response across all the different strains of B. burgdorferi, B. afzelii and B. garinii tested.

Additional chimeras were constructed and are listed in Table VII.

TABLE VII

OspC Polypeptides and Chimeric Polypeptides of the Present Invention

| POLYPEPTIDE | SEQ ID NO.: (DNA) | (POLYPEPTIDES) |
| --- | --- | --- |
| [1]unlip OspC kkp (55–621[+]) | 45 | 46 |
| unlip OspC PKO | 47 | 48 |
| unlip OspC TRO | 49 | 50 |
| [2]unlip OspC-55B31/58PKO/56TRO | 51 | 52 |
| unlip OspC2-TRO | 53 | 54 |
| unlip OspCB31-TRO | 55 | 56 |
| unlip OspCPkoCTro | 59 | 60 |
| [3]BlipOspC1C10 | 61 | 62 |
| Blip OspC5C7 | 77 | 78 |
| Blip OspC2C12 | 67 | 78 |
| Blip OspC1C12 | 63 | 64 |
| Blip OspC2C10 | 65 | 66 |
| Blip OspC2C7 | 69 | 70 |
| Blip OspC5C12 | 75 | 76 |
| Blip OspC2TRO | 71 | 72 |
| Blip OspC5C10 | 73 | 74 |
| Blip OspCB31TRO | 79 | 80 |
| Blip OspCB31C10 | 81 | 82 |
| Blip OspCB31C12 | 83 | 84 |
| Blip OspCPkoTro | 85 | 86 |

While this invention has been particularly shown and described with references to preferred embodiments thereof, it will be understood by those skilled in the art that various changes in form and details may be made therein without departing from the spirit and scope of the invention as defined by the appended claims.

SEQUENCE LISTING (1) GENERAL INFORMATION:

(iii) NUMBER OF SEQUENCES: 52

(2) INFORMATION FOR SEQ ID NO: 1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

AGGCGTCTCG AGACAGAGGA GAGCAAGAAA TG      32

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

TTTCCCTCTA GATAAGCCAT CCAATCACAC                        30

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GAAGGATCCA TGAAAAAATA TTTATTGGG                         29

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

ACTGTCGACT TATTTTAAAG CGTTTTTAAG                        30

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GCCAGTTTTG GATCCTTAAA AAAGGCTTGG                        30

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

TTGTGAGGGA CAGAATTCCA ATCAGGG                          27

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
CAGTGATATC CCGGGAGACT CCTC                                      24
```

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

```
GAATAGAAGA ACTCCTCTAG AATTC                                     25
```

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

```
GCCTTAGGCG GATCCTATGG CAGGAAG                                   27
```

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

```
TAAGATGGGT GGCCATGGTG AATT                                      24
```

(2) INFORMATION FOR SEQ ID NO: 11:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO: 11:

```
Cys Asn Thr Arg Lys Arg Ile Arg Ile Gln Arg Gly Pro Gly Arg Ala
 1               5                  10                  15
Phe Val Thr Ile Gly Lys
            20
```

(2) INFORMATION FOR SEQ ID NO: 12:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 12:

```
Tyr Asn Lys Arg Lys Arg Ile His Ile Gln Arg Gly Pro Gly Arg Ala
 1               5                  10                  15
Phe Tyr Thr Thr Lys Asn Ile Ile Cys
            20                  25
```

(2) INFORMATION FOR SEQ ID NO: 13:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 13:

```
Cys Arg Ile Lys Gln Phe Ile Asn Met Trp Gln Glu Val Gly Lys Ala
 1               5                  10                  15
Met Thr Ala Pro Pro Ile Ser Gly Ile Arg Cys
            20                  25
```

(2) INFORMATION FOR SEQ ID NO: 14:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 14:

```
Arg Ile Leu Ala Val Glu Arg Tyr Ile Lys Asp Gln Gln Leu Leu Gly Ile
 1               5                  10                  15
Trp Gly Cys Ser Gly Lys Leu Ile Cys
            20                  25
```

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

TTGTTTAACT TTTGATCGAT CCATTCC                                      27

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GATTTGTATC GATGATCTGA C                                    21

(2) INFORMATION FOR SEQ ID NO: 17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

TGTAGTAGCA AAAGAAATAG TTAAG                                25

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

AATTCTTAAC TATTTCTTTT GCTAC                                25

(2) INFORMATION FOR SEQ ID NO: 19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

ATTTGTCGAC TGGTTTCAGC CTGCCATGGC AGGAAGAAGC                 40

(2) INFORMATION FOR SEQ ID NO: 20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

ACGACGCGTA TTCTTTAGCT CCTGACTCC                            29

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

GCTGACGGTA GCGGCCGCAC AATT                                                24

(2) INFORMATION FOR SEQ ID NO: 22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GTATTAAGCG GCCGCAATTG TT                                                  22

(2) INFORMATION FOR SEQ ID NO: 23:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

AAAAAGCTTC GCGGATCCGC GTTGCGGCCG CAACCGGTCA CCGGCGACGC GTCGGTCGAC          60

CGGTCATGGC TGGGCCCC                                                       78

(2) INFORMATION FOR SEQ ID NO: 24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CCCAAGCTTA GACATGATAA GATACATTG                                           29

(2) INFORMATION FOR SEQ ID NO: 25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

CTAGCAGCTG GATCCCAGCT TC                                                  22

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

GGATTTCTGG GGATCCAAGC TAGT                                          24

(2) INFORMATION FOR SEQ ID NO: 27:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 27:

TATAGGATCC GCGCAATGAA AGACCCCACC T                                  31

(2) INFORMATION FOR SEQ ID NO: 28:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 28:

ATATGGATCC GCAATGAAAG ACCCCCGCTG A                                  31

(2) INFORMATION FOR SEQ ID NO: 29:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 29:

TAAAGCGGCC GCTCCTATGG CAGGAAGACG                                    30

(2) INFORMATION FOR SEQ ID NO: 30:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 30:

ATTACGCGTC TTATGCTTCT AGCCAGGCAC AATG                               34

(2) INFORMATION FOR SEQ ID NO: 31:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 31:

ATTACGCGTT TATTACAGAA TGGAAAACAG ATGGCAGGTG                           40

(2) INFORMATION FOR SEQ ID NO: 32:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

ATTACGCGTT ATTGCAGAAT TCTTATTATG GC                                  32

(2) INFORMATION FOR SEQ ID NO: 33:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

GAGGCTTGGA GAGGATTATA GAAGTACTGC AAGAGCTG                             38

(2) INFORMATION FOR SEQ ID NO: 34:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

GAATCCTCTC CAAGCCTCAG CTACTGCTAT AGCTGTGGC                            39

(2) INFORMATION FOR SEQ ID NO: 35:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

AAAAATAAAG CGGCCGCTCC TATGGCAGGA AGAGAAGCG                            39

(2) INFORMATION FOR SEQ ID NO: 36:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

AAAAAATTAC GCGTCTTATG CTTCTAGCCA GGCACAATG                                   39

(2) INFORMATION FOR SEQ ID NO: 37:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

CCCAAGCTTG GGAATGCTCT GCCAGTGTTA C                                           31

(2) INFORMATION FOR SEQ ID NO: 38:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

GGGGGCCGGA AGGGCACAAT AAAACTGTCT GCTTAC                                      36

(2) INFORMATION FOR SEQ ID NO: 39:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

CCTGATTCAG GTGAAAATAT TGTTGATGCG CTG                                         33

(2) INFORMATION FOR SEQ ID NO: 40:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

AACATCAATA CAACCTATTA ATTTCCCCTC GTCAAAAATA AGGTTATCAA GTGAGAAATC            60

ACCATCAGTG ACGACTGAAT CCGGTGAGAA TGGCAAAAGT TTATGCATTT C                    111

(2) INFORMATION FOR SEQ ID NO: 41:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 41:

CTAGCGCGGG GATCCGCGTT GCGGCCGCAA AAAGTCGACG GGCGACGCGT AAAAA          55

(2) INFORMATION FOR SEQ ID NO: 42:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 42:

GATCTTTTTA CGCGTCGCCC GTCGACTTTT TGCGGCCGCA ACGCGGATCC CCGCG          55

(2) INFORMATION FOR SEQ ID NO: 43:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 43:

ATGTCGACTG GTTTCAGCCT GCCATGGCAG GAAGAAGC                             38

(2) INFORMATION FOR SEQ ID NO: 44:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 44:

CCCCACGACG CGTCTATTCT TTAGCTCCTG ACTCC                                35

(2) INFORMATION FOR SEQ ID NO: 45:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 45:

TTTGCGGCCG CGTAAGTGGA GAGAGATGGT GCGAG                                35

(2) INFORMATION FOR SEQ ID NO: 46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 46:

CTGGTGGGGC TGTTGGCTCT G                                              21

(2) INFORMATION FOR SEQ ID NO: 47:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 47:

AATTTAATAA GTAAGTAAGT GTCATATGTT TGTTTGAATT CTGCAACAAC TGCTGTTTAT    60

CCATTTTCAG AATTGGGTG                                                 79

(2) INFORMATION FOR SEQ ID NO: 48:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 48:

TCGACACCCA ATTCTGAAAA TGGATAAACA GCACTTGTTG CAGAATTCAA ACAAACATAT    60

GACACTTACT TACTTATTA                                                 79

(2) INFORMATION FOR SEQ ID NO: 49:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 49:

GGGGTTTTTG GGCATATGTA TGAGGGACAA TTGGAGAAGT G                        41

(2) INFORMATION FOR SEQ ID NO: 50:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 50:

AAGCTTGTGG AATTCTTAAT TTCTCTGTCC GGGGTTTTTG GGCATATGTA TGAGGGACAT    60

TGGAGAAGTG                                                           70

(2) INFORMATION FOR SEQ ID NO: 51:

(i) SEQUENCE CHARACTERISTICS:
            (A) LENGTH: 19 base pairs
            (B) TYPE: nucleic acid -continued

```
        (C) STRANDEDNESS: single
        (D) TOPOLOGY: linear (ii) MOLECULE TYPE: DNA (xi) SEQUENCE DESCRIPTION: SEQ ID NO: 51:

CAGTATCTGG CATGGGTAC                                                  19

(2) INFORMATION FOR SEQ ID NO: 52:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 52:

CCATGCCAGA TACTGGTAC                                                  19
```

What is claimed is:

1. A composition comprising OspC polypeptides from Lyme Disease causing *Borrelia* wherein
said composition comprises one or more OspC polypeptides from at least two *Borrelia burgdorferi* sensu stricto OspC families selected from the group consisting of: A, B, I, and K, expecting the combination consisting of two OspC proteins wherein one OspC protein is from family A and the second OspC protein is from family I.

2. The composition of claim 1 comprising one or more OspC polypeptides from each of said *Borrelia burgdorferi* sensu stricto families.

3. The composition of claim 1, wherein said OspC polypeptide comprises the OspC protein variable region.

4. The composition of claim 3, wherein said OspC polypeptide is encoded by a nucleic acid comprising nucleotide 26 to about nucleotide 621 of an ospC gene.

5. The composition of claim 3, wherein said OspC polypeptide is encoded by a nucleic acid comprising nucleotide 53 to about nucleotide 570 of an ospC gene.

6. The composition of claim 1, wherein at least two of said OspC polypeptides are fused together in a single protein, encoded by a single nucleic acid, wherein polypeptides in said fusion protein are not found in the same configuration in a naturally occurring OspC protein.

7. The composition of claim 1, wherein the ospC genes encoding the OspC polypeptides within a given OspC family are at least 98% identical at the nucleic acid level.

8. The composition of claim 7, wherein *Borrelia burgdorferi* sensu stricto OspC family A comprises strains B31, CA4, HII, IP1, IP2, IP3, L5, PIF, Pka, Txgw and strains containing ospC allele OC1.

9. The composition of claim 7, wherein *Borrelia burgdorferi* sensu stricto OspC family B comprises strains 35B808, 61 BV3, BUR, DK7, PB3, Z57 and strains containing ospC genes OC2 and OC3.

10. The composition of claim 7, wherein *Borrelia burgdorferi* sensu stricto OspC family I comprises strains 297, HB19 and strains containing ospC gene OC10, wherein strain 297 is characterized by ospC of GenBank accession number L42893 (SEQ ID NO:85).

11. The composition of claim 7, wherein *Borrelia burgdorferi* sensu stricto OspC family K comprises strains 272, 297, 28354, KIPP, MUL and strains containing ospC gene OC12 and OC13, wherein strain 297 is characterized by ospC of GenBank accession number U08284 (SEQ ID NO:86).

12. A chimeric protein comprising OspC polypeptides from two or more Lyme Disease causing OspC families of Lyme Disease causing *Borrelia* wherein said chimeric protein comprises:
   a) a first OspC polypeptide encoded by a nucleic acid comprising a sequence from about nucleotide 26 to about nucleotide 621 of an ospC gene from a first OspC family and
   b) a second OspC polypeptide encoded by a nucleic acid comprising a sequence from about nucleotide 28 to about nucleotide 570 of an ospC gene from a second OspC family,
wherein said OspC families are selected from the group consisting of: *Borrelia burgdorferi* sensu stricto OspC families A, B, I, and K, and *Borrelia afzelii* OspC families A and B.

13. A chimeric protein comprising OspC polypeptides from two or more Lyme Disease causing OspC families of Lyme Disease causing *Borrelia* wherein said chimeric protein comprises:
   a) a first OspC polypeptide encoded by a nucleic acid comprising a sequence from about nucleotide 53 To about nucleotide 570 of an ospC gene from a first OspC family and
   b) a second OspC polypeptide encoded by a nucleic acid comprising a sequence from about nucleotide 28 to about nucleotide 570 of an ospC gene from a second OspC family,
wherein said OspC families are selected from the group consisting of: *Borrelia burgdorferi* sensu stricto OspC families A, B, I, and K, and *Borrelia afzelii* OspC families A and B.

14. The chimeric protein of claim 13, wherein said protein is unlipidated.

15. A chimeric OspC protein selected from the group consisting of: SEQ Id Nos: 24, 26, 28, 30, 32, 34, 36, 38, 40, 42, 52, 54, 56, 58, 60, 62, 64, 66, 68, 70, 72, 74, 76, 78, 80, 82, and 84.

16. The composition of claim 1, further comprising at least one OspC polypeptide from each of *Borrelia afzelii* OspC families A and B.

17. The composition of claim 16, wherein *Borrelia afzelii* OspC family A comprises strains Pbo, Pwud, PKO, Pgau, DK2, DK3, DK21, DK8, Bfox and JSB.

18. The composition of claim 16, wherein *Borrelia afzelii* OspC family B comprises strains DK5, ACA1, DK9, XB18h, Ple and 134M.

19. The chimeric protein of claim 12, wherein said protein is unlipidated.

* * * * *

UNITED STATES PATENT AND TRADEMARK OFFICE
CERTIFICATE OF CORRECTION

| | | |
|---|---|---|
| PATENT NO. | : 7,060,281 B1 | Page 1 of 1 |
| APPLICATION NO. | : 09/596746 | |
| DATED | : June 13, 2006 | |
| INVENTOR(S) | : Raymond J. Dattwyler et al. | |

It is certified that error appears in the above-identified patent and that said Letters Patent is hereby corrected as shown below:

On The Title Page 54, delete the word "Barrelia" and insert --- Borrelia---.

Column 45, line 31, delete the word "expecting" and insert --- excepting ---.

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,060,281 B1 | Page 1 of 63 |
| APPLICATION NO. | : 09/596746 | |
| DATED | : June 13, 2006 | |
| INVENTOR(S) | : Raymond J. Dattwyler et al. | |

It is certified that error appears in the above-identified patent and that said Letters Patent is hereby corrected as shown below:

Column 45, Insert SEQ ID NOS. 53-86 after SEQ ID NO: 52 as attached.

Signed and Sealed this

Sixteenth Day of October, 2007

JON W. DUDAS
*Director of the United States Patent and Trademark Office*

<210> 53

<211> 1137
<212> DNA
<213> ospC Chimera

<220>
<221> CDS
<222> (1)...(1137)

<400> 53

```
atg gct tgt aat aat tca ggg aaa gat ggg aat aca tct gca aat tct    48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa    96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg   144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata   192
```

```
Leu Leu Ser Ser Ile Asp Glu Leu Ala Lys Ala Ile Gly Lys Lys Ile
        50                  55                  60 aaa aac gat ggt agt tta gat aac gaa gca aat cgc aac gag tca ttg    240
Lys Asn Asp Gly Ser Leu Asp Asn Glu Ala Asn Arg Asn Glu Ser Leu
 65                  70                  75                  80 tta gca gga gct tat aca ata tca acc tta ata aca caa aaa tta agt    288
Leu Ala Gly Ala Tyr Thr Ile Ser Thr Leu Ile Thr Gln Lys Leu Ser
                 85                  90                  95 aaa tta aac gga tca gaa ggt tta aag gaa aag att gcc gca gct aag    336
Lys Leu Asn Gly Ser Glu Gly Leu Lys Glu Lys Ile Ala Ala Ala Lys
             100                 105                 110 aaa tgc tct gaa gay ttt agt act aaa cta aaa gat aat cat gca cag    384
Lys Cys Ser Glu Glu Phe Ser Thr Lys Leu Lys Asp Asn His Ala Gln
         115                 120                 125 ctt ggt ata cag ggc gtt act gat gaa aat gca aaa aaa gct att tta    432
Leu Gly Ile Gln Gly Val Thr Asp Glu Asn Ala Lys Lys Ala Ile Leu
     130                 135                 140 aaa gca aat gca gcg ggt aaa gat aag ggc gtt gaa gaa ctt gaa aag    480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt    528
Leu Ser Gly Ser Leu Glu Ser Leu Ser Lys Ala Ala Lys Glu Met Leu
                 165                 170                 175 gct aat tca gtt aaa gag ctt aca agc cct gtt gtc cat ggt aat aat    576
Ala Asn Ser Val Lys Glu Leu Thr Ser Pro Val Val His Gly Asn Asn
             180                 185                 190 tca ggt ggg gat tct gca tct act aat cct gat gag tct gca aaa gga    624
Ser Gly Gly Asp Ser Ala Ser Thr Asn Pro Asp Glu Ser Ala Lys Gly
         195                 200                 205 cct aat ctt acc gta ata agc aaa aaa att aca gat tct aat gca ttt    672
Pro Asn Leu Thr Val Ile Ser Lys Lys Ile Thr Asp Ser Asn Ala Phe
     210                 215                 220 tta ctg gct gtg aaa gaa gtt gag gct ttg ctt tca tct ata gat gaa    720
Leu Leu Ala Val Lys Glu Val Glu Ala Leu Leu Ser Ser Ile Asp Glu
225                 230                 235                 240
```

```
ctt tct aaa gct att ggt aaa aaa ata aaa aat gat ggt act tta gat    768
Leu Ser Lys Ala Ile Gly Lys Lys Ile Lys Asn Asp Gly Thr Leu Asp
            245             250             255 aac gaa gca aat cga aac gaa tca ttg ata gca gga gct tat gaa ata    816
Asn Glu Ala Asn Arg Asn Glu Ser Leu Ile Ala Gly Ala Tyr Glu Ile
            260             265             270 tca aaa cta ata aca caa aaa tta agt gta ttg aat tca gaa gaa tta    864
Ser Lys Leu Ile Thr Gln Lys Leu Ser Val Leu Asn Ser Glu Glu Leu
            275             280             285 aag aaa aaa att aaa gag gct aag gat tgt tcc caa aaa ttt act act    912
Lys Lys Lys Ile Lys Glu Ala Lys Asp Cys Ser Gln Lys Phe Thr Thr
            290             295             300 aag cta aaa gat agt cat gca gag ctt ggt ata caa agc gtt cag gat    960
Lys Leu Lys Asp Ser His Ala Glu Leu Gly Ile Gln Ser Val Gln Asp
305             310             315             320 gat aat gca aaa aaa gct att tta aaa aca cat gga act aaa gac aag    1008
Asp Asn Ala Lys Lys Ala Ile Leu Lys Thr His Gly Thr Lys Asp Lys
                325             330             335 ggt gct aaa gaa ctt gaa gag tta ttt aaa tca cta gaa agc ttg tca    1056
Gly Ala Lys Glu Leu Glu Glu Leu Phe Lys Ser Leu Glu Ser Leu Ser
            340             345             350 aaa gca gcg caa gca gca tta act aat tca gtt aaa gag ctt aca aat    1104
Lys Ala Ala Gln Ala Ala Leu Thr Asn Ser Val Lys Glu Leu Thr Asn
            355             360             365 cct gtt gtg gca gaa agt cca aaa aaa cct taa                        1137
Pro Val Val Ala Glu Ser Pro Lys Lys Pro  *
370             375
```

<210> 54
<211> 378
<212> PRT
<213> ospC Chimera

<400> 54

| | | | | | | | | | | | | | | |
|---|---|---|---|---|---|---|---|---|---|---|---|---|---|---|
| Met | Ala | Cys | Asn | Asn | Ser | Gly | Lys | Asp | Gly | Asn | Thr | Ser | Ala | Asn | Ser |
| 1 | | | | 5 | | | | | 10 | | | | | 15 | |
| Ala | Asp | Glu | Ser | Val | Lys | Gly | Pro | Asn | Leu | Thr | Glu | Ile | Ser | Lys | Lys |
| | | | 20 | | | | | 25 | | | | | 30 | | |
| Ile | Thr | Asp | Ser | Asn | Ala | Val | Leu | Leu | Ala | Val | Lys | Glu | Val | Glu | Ala |
| | | 35 | | | | | 40 | | | | | 45 | | | |
| Leu | Leu | Ser | Ser | Ile | Asp | Glu | Leu | Ala | Lys | Ala | Ile | Gly | Lys | Lys | Ile |
| | 50 | | | | | 55 | | | | | 60 | | | | |
| Lys | Asn | Asp | Gly | Ser | Leu | Asp | Asn | Glu | Ala | Asn | Arg | Asn | Glu | Ser | Leu |
| 65 | | | | | 70 | | | | | 75 | | | | | 80 |
| Leu | Ala | Gly | Ala | Tyr | Thr | Ile | Ser | Thr | Leu | Ile | Thr | Gln | Lys | Leu | Ser |
| | | | | 85 | | | | | 90 | | | | | 95 | |
| Lys | Leu | Asn | Gly | Ser | Glu | Gly | Leu | Lys | Glu | Lys | Ile | Ala | Ala | Ala | Lys |
| | | | 100 | | | | | 105 | | | | | 110 | | |
| Lys | Cys | Ser | Glu | Glu | Phe | Ser | Thr | Lys | Leu | Lys | Asp | Asn | His | Ala | Gln |
| | | 115 | | | | | 120 | | | | | 125 | | | |
| Leu | Gly | Ile | Gln | Gly | Val | Thr | Asp | Glu | Asn | Ala | Lys | Lys | Ala | Ile | Leu |
| | 130 | | | | | 135 | | | | | 140 | | | | |
| Lys | Ala | Asn | Ala | Ala | Gly | Lys | Asp | Lys | Gly | Val | Glu | Glu | Leu | Glu | Lys |
| 145 | | | | | 150 | | | | | 155 | | | | | 160 |
| Leu | Ser | Gly | Ser | Leu | Glu | Ser | Leu | Ser | Lys | Ala | Ala | Lys | Glu | Met | Leu |
| | | | | 165 | | | | | 170 | | | | | 175 | |
| Ala | Asn | Ser | Val | Lys | Glu | Leu | Thr | Ser | Pro | Val | Val | His | Gly | Asn | Asn |
| | | | 180 | | | | | 185 | | | | | 190 | | |
| Ser | Gly | Gly | Asp | Ser | Ala | Ser | Thr | Asn | Pro | Asp | Glu | Ser | Ala | Lys | Gly |
| | | 195 | | | | | 200 | | | | | 205 | | | |
| Pro | Asn | Leu | Thr | Val | Ile | Ser | Lys | Lys | Ile | Thr | Asp | Ser | Asn | Ala | Phe |
| | | 210 | | | | | 215 | | | | | 220 | | | |
| Leu | Leu | Ala | Val | Lys | Glu | Val | Glu | Ala | Leu | Leu | Ser | Ser | Ile | Asp | Glu |
| 225 | | | | | 230 | | | | | 235 | | | | | 240 |
| Leu | Ser | Lys | Ala | Ile | Gly | Lys | Lys | Ile | Lys | Asn | Asp | Gly | Thr | Leu | Asp |
| | | | | 245 | | | | | 250 | | | | | 255 | |
| Asn | Glu | Ala | Asn | Arg | Asn | Glu | Ser | Leu | Ile | Ala | Gly | Ala | Tyr | Glu | Ile |
| | | | 260 | | | | | 265 | | | | | 270 | | |
| Ser | Lys | Leu | Ile | Thr | Gln | Lys | Leu | Ser | Val | Leu | Asn | Ser | Glu | Glu | Leu |
| | | 275 | | | | | 280 | | | | | 285 | | | |
| Lys | Lys | Lys | Ile | Lys | Glu | Ala | Lys | Asp | Cys | Ser | Gln | Lys | Phe | Thr | Thr |
| | 290 | | | | | 295 | | | | | 300 | | | | |
| Lys | Leu | Lys | Asp | Ser | His | Ala | Glu | Leu | Gly | Ile | Gln | Ser | Val | Gln | Asp |
| 305 | | | | | 310 | | | | | 315 | | | | | 320 |

```
Asp Asn Ala Lys Lys Ala Ile Leu Lys Thr His Gly Thr Lys Asp Lys
                325                 330                 335
Gly Ala Lys Glu Leu Glu Glu Leu Phe Lys Ser Leu Glu Ser Leu Ser
            340                 345                 350
Lys Ala Ala Gln Ala Ala Leu Thr Asn Ser Val Lys Glu Leu Thr Asn
        355                 360                 365
Pro Val Val Ala Glu Ser Pro Lys Lys Pro
    370                 375
```

<210> 55
<211> 1158
<212> DNA
<213> ospC Chimera

<220>
<221> CDS
<222> (1)...(1158)

<400> 55

```
atg gct tgt aat aat tca ggg aaa gat ggg aat aca

```
gat gga ttg aaa aat gaa gga tta aag gaa aaa att gat gcg gct aag    336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat    384
Lys Cys Ser Glu Thr Phe Thr Asn Lys Leu Lys Glu Lys His Thr Asp
            115                 120                 125 ctt ggt aaa gaa ggt gtt act gat gct gat gca aaa gaa gcc att tta    432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta    480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct    528
Phe Glu Ser Val Glu Val Leu Ser Lys Ala Ala Lys Glu Met Leu Ala
            165                 170                 175 aat tca gtt aaa gag ctt aca agc cct gtt gtg gca gaa agt cca aaa    576
Asn Ser Val Lys Glu Leu Thr Ser Pro Val Val Ala Glu Ser Pro Lys
            180                 185                 190 aaa cct ttc cat ggt aat aat tca ggt ggg gat tct gca tct act aat    624
Lys Pro Phe His Gly Asn Asn Ser Gly Gly Asp Ser Ala Ser Thr Asn
            195                 200                 205 cct gat gag tct gca aaa gga cct aat ctt acc gta ata agc aaa aaa    672
Pro Asp Glu Ser Ala Lys Gly Pro Asn Leu Thr Val Ile Ser Lys Lys
    210                 215                 220 att aca gat tct aat gca ttt tta ctg gct gtg aaa gaa gtt gag gct    720
Ile Thr Asp Ser Asn Ala Phe Leu Leu Ala Val Lys Glu Val Glu Ala
225                 230                 235                 240 ttg ctt tca tct ata gat gaa ctt tct aaa gct att ggt aaa aaa ata    768
Leu Leu Ser Ser Ile Asp Glu Leu Ser Lys Ala Ile Gly Lys Lys Ile
            245                 250                 255 aaa aat gat ggt act tta gat aac gaa gca aat cga aac gaa tca ttg    816
Lys Asn Asp Gly Thr Leu Asp Asn Glu Ala Asn Arg Asn Glu Ser Leu
            260                 265                 270 ata gca gga gct tat gaa ata tca aaa cta ata aca caa aaa tta agt    864
Ile Ala Gly Ala Tyr Glu Ile Ser Lys Leu Ile Thr Gln Lys Leu Ser
            275                 280                 285
```

```
gta ttg aat tca gaa gaa tta aag aaa aaa att aaa gag gct aag gat    912
Val Leu Asn Ser Glu Glu Leu Lys Lys Lys Ile Lys Glu Ala Lys Asp
    290             295                 300 tgt tcc caa aaa ttt act act aag cta aaa gat agt cat gca gag ctt    960
Cys Ser Gln Lys Phe Thr Thr Lys Leu Lys Asp Ser His Ala Glu Leu
305             310                 315                 320 ggt ata caa agc gtt cag gat gat aat gca aaa aaa gct att tta aaa   1008
Gly Ile Gln Ser Val Gln Asp Asp Asn Ala Lys Lys Ala Ile Leu Lys
                325                 330                 335 aca cat gga act aaa gac aag ggt gct aaa gaa ctt gaa gag tta ttt   1056
Thr His Gly Thr Lys Asp Lys Gly Ala Lys Glu Leu Glu Glu Leu Phe
            340                 345                 350 aaa tca cta gaa agc ttg tca aaa gca gcg caa gca gca tta act aat   1104
Lys Ser Leu Glu Ser Leu Ser Lys Ala Ala Gln Ala Ala Leu Thr Asn
        355                 360                 365 tca gtt aaa gag ctt aca aat cct gtt gtg gca gaa agt cca aaa aaa   1152
Ser Val Lys Glu Leu Thr Asn Pro Val Val Ala Glu Ser Pro Lys Lys
    370             375                 380 cct taa                                                            1158
Pro *
385

<210> 56
<211> 385
<212> PRT
<213> ospC Chimera

<400> 56
Met Ala Cys Asn Asn Ser Gly Lys Asp Gly Asn Thr Ser Ala Asn Ser
1               5                   10                  15
Ala Asp Glu Ser Val Lys Gly Pro Asn Leu Thr Glu Ile Ser Lys Lys
                20                  25                  30
Ile Thr Asp Ser Asn Ala Val Leu Leu Ala Val Lys Glu Val Glu Ala
            35                  40                  45
Leu Leu Ser Ser Ile Asp Glu Ile Ala Ala Lys Ala Ile Gly Lys Lys
        50                  55                  60
Ile His Gln Asn Asn Gly Leu Asp Thr Glu Tyr Asn His Asn Gly Ser
65              70                  75                  80
```

```
Leu Leu Ala Gly Ala Tyr Ala Ile Ser Thr Leu Ile Lys Gln Lys Leu
                85                  90                      95
Asp Gly Leu Lys Asn Glu Gly Leu Lys Glu Lys Ile Asp Ala Ala Lys
            100                 105                 110
Lys Cys Ser Glu Thr Phe Thr Asn Lys Leu Lys Glu Lys His Thr Asp
            115                 120                 125
Leu Gly Lys Glu Gly Val Thr Asp Ala Asp Ala Lys Glu Ala Ile Leu
130             135                 140
Lys Thr Asn Gly Thr Lys Thr Lys Gly Ala Glu Glu Leu Gly Lys Leu
145                 150                 155                 160
Phe Glu Ser Val Glu Val Leu Ser Lys Ala Ala Lys Glu Met Leu Ala
                165                 170                 175
Asn Ser Val Lys Glu Leu Thr Ser Pro Val Val Ala Glu Ser Pro Lys
                180                 185                 190
Lys Pro Phe His Gly Asn Asn Ser Gly Gly Asp Ser Ala Ser Thr Asn
            195                 200                 205
Pro Asp Glu Ser Ala Lys Gly Pro Asn Leu Thr Val Ile Ser Lys Lys
    210                 215                 220
Ile Thr Asp Ser Asn Ala Phe Leu Leu Ala Val Lys Glu Val Glu Ala
225                 230                 235                 240
Leu Leu Ser Ser Ile Asp Glu Leu Ser Lys Ala Ile Gly Lys Lys Ile
                245                 250                 255
Lys Asn Asp Gly Thr Leu Asp Asn Glu Ala Asn Arg Asn Glu Ser Leu
            260                 265                 270
Ile Ala Gly Ala Tyr Glu Ile Ser Lys Leu Ile Thr Gln Lys Leu Ser
            275                 280                 285
Val Leu Asn Ser Glu Glu Leu Lys Lys Lys Ile Lys Glu Ala Lys Asp
    290                 295                 300
Cys Ser Gln Lys Phe Thr Thr Lys Leu Lys Asp Ser His Ala Glu Leu
305                 310                 315                 320
Gly Ile Gln Ser Val Gln Asp Asp Asn Ala Lys Lys Ala Ile Leu Lys
                325                 330                 335
Thr His Gly Thr Lys Asp Lys Gly Ala Lys Glu Leu Glu Glu Leu Phe
            340                 345                 350
Lys Ser Leu Glu Ser Leu Ser Lys Ala Ala Gln Ala Ala Leu Thr Asn
        355                 360                 365
Ser Val Lys Glu Leu Thr Asn Pro Val Val Ala Glu Ser Pro Lys Lys
370                 375                 380
```

Pro
385

<210> 57
<211> 1161
<212> DNA
<213> ospC Chimera

<220>
<221> CD

```
        Asp Leu Gly Lys Gln Asp Ala Thr Asp His Ala Lys Ala Ala Ile
            130                 135                 140 tta aaa aca cat gca act acc gat aaa ggt gct aaa gaa ttt aaa gat       480
Leu Lys Thr His Ala Thr Thr Asp Lys Gly Ala Lys Glu Phe Lys Asp
145                 150                 155                 160 tta ttt gaa tca gta gaa ggt ttg tta aaa gca gct caa gta gca cta       528
Leu Phe Glu Ser Val Glu Gly Leu Leu Lys Ala Ala Gln Val Ala Leu
                165                 170                 175 act aat tca gtt aaa gaa ctt aca agt cct gtt gta gca gaa agt cca       576
Thr Asn Ser Val Lys Glu Leu Thr Ser Pro Val Val Ala Glu Ser Pro
            180                 185                 190 aaa aaa cct cat atg gct aat aat tca ggt ggg gat tct gca tct act       624
Lys Lys Pro His Met Ala Asn Asn Ser Gly Gly Asp Ser Ala Ser Thr
        195                 200                 205 aat cct gat gag tct gca aaa gga cct aat ctt acc gta ata agc aaa       672
Asn Pro Asp Glu Ser Ala Lys Gly Pro Asn Leu Thr Val Ile Ser Lys
    210                 215                 220 aaa att aca gat tct aat gca ttt tta ctg gct gtg aaa gaa gtt gag       720
Lys Ile Thr Asp Ser Asn Ala Phe Leu Leu Ala Val Lys Glu Val Glu
225                 230                 235                 240 gct ttg ctt tca tct ata gat gaa ctt tct aaa gct att ggt aaa aaa       768
Ala Leu Leu Ser Ser Ile Asp Glu Leu Ser Lys Ala Ile Gly Lys Lys
                245                 250                 255 ata aaa aat gat ggt act tta gat aac gaa gca aat cga aac gaa tca       816
Ile Lys Asn Asp Gly Thr Leu Asp Asn Glu Ala Asn Arg Asn Glu Ser
            260                 265                 270 ttg ata gca gga gct tat gaa ata tca aaa cta ata aca caa aaa tta       864
Leu Ile Ala Gly Ala Tyr Glu Ile Ser Lys Leu Ile Thr Gln Lys Leu
        275                 280                 285 agt gta ttg aat tca gaa gaa tta aag aaa aaa att aaa gag gct aag       912
Ser Val Leu Asn Ser Glu Glu Leu Lys Lys Lys Ile Lys Glu Ala Lys
    290                 295                 300 gat tgt tcc caa aaa ttt act act aag cta aaa gat agt cat gca gag       960
Asp Cys Ser Gln Lys Phe Thr Thr Lys Leu Lys Asp Ser His Ala Glu
305                 310                 315                 320
``` ctt ggt ata caa agc gtt cag gat gat aat gca aaa aaa gct att tta 1008
Leu Gly Ile Gln Ser Val Gln Asp Asp Asn Ala Lys Lys Ala Ile Leu
325 330 335 aaa aca cat gga act aaa gac aag ggt gct aaa gaa ctt gaa gag tta 1056
Lys Thr His Gly Thr Lys Asp Lys Gly Ala Lys Glu Leu Glu Glu Leu
340 345 350 ttt aaa tca cta gaa agc ttg tca aaa gca gcg caa gca gca tta act 1104
Phe Lys Ser Leu Glu Ser Leu Ser Lys Ala Ala Gln Ala Ala Leu Thr
355 360 365 aat tca gtt aaa gag ctt aca aat cct gtt gtg gca gaa agt cca aaa 1152
Asn Ser Val Lys Glu Leu Thr Asn Pro Val Val Ala Glu Ser Pro Lys
370 375 380 aaa cct taa 1161
Lys Pro *
385

<210> 58
<211> 386
<212> PRT
<213> ospC Chimera

<400> 58
Met Cys Ser Asn Ser Gly Lys Gly Gly Asp Ser Ala Ser Thr Asn Pro
1 5 10 15
Ala Asp Glu Ser Ala Lys Gly Pro Asn Leu Thr Glu Ile Ser Lys Lys
20 25 30
Ile Thr Asp Ser Asn Ala Phe Val Leu Ala Val Lys Glu Val Glu Thr
35 40 45
Leu Val Leu Ser Ile Asp Glu Leu Ala Lys Lys Ala Ile Gly Gln Lys
50 55 60
Ile Asp Asn Asn Asn Gly Leu Ala Ala Leu Asn Asn Gln Asn Gly Ser
65 70 75 80
Leu Leu Ala Gly Ala Tyr Ala Ile Ser Thr Leu Ile Thr Glu Lys Leu
85 90 95
Ser Lys Leu Lys Asn Leu Glu Glu Leu Lys Thr Glu Ile Ala Lys Ala
100 105 110
Lys Lys Cys Ser Glu Glu Phe Thr Asn Lys Leu Lys Ser Gly His Ala
115 120 125
Asp Leu Gly Lys Gln Asp Ala Thr Asp Asp His Ala Lys Ala Ala Ile
130 135 140

```
Leu Lys Thr His Ala Thr Thr Asp Lys Gly Ala Lys Glu Phe Lys Asp
145                 150                 155                 160
Leu Phe Glu Ser Val Glu Gly Leu Leu Lys Ala Ala Gln Val Ala Leu
                165                 170                 175
Thr Asn Ser Val Lys Glu Leu Thr Ser Pro Val Val Ala Glu Ser Pro
                180                 185                 190
Lys Lys Pro His Met Ala Asn Asn Ser Gly Gly Asp Ser Ala Ser Thr
            195                 200                 205
Asn Pro Asp Glu Ser Ala Lys Gly Pro Asn Leu Thr Val Ile Ser Lys
            210                 215                 220
Lys Ile Thr Asp Ser Asn Ala Phe Leu Leu Ala Val Lys Glu Val Glu
225                 230                 235                 240
Ala Leu Leu Ser Ser Ile Asp Glu Leu Ser Lys Ala Ile Gly Lys Lys
                245                 250                 255
Ile Lys Asn Asp Gly Thr Leu Asp Asn Glu Ala Asn Arg Asn Glu Ser
            260                 265                 270
Leu Ile Ala Gly Ala Tyr Glu Ile Ser Lys Leu Ile Thr Gln Lys Leu
            275                 280                 285
Ser Val Leu Asn Ser Glu Glu Leu Lys Lys Lys Ile Lys Glu Ala Lys
            290                 295                 300
Asp Cys Ser Gln Lys Phe Thr Thr Lys Leu Lys Asp Ser His Ala Glu
305                 310                 315                 320
Leu Gly Ile Gln Ser Val Gln Asp Asp Asn Ala Lys Lys Ala Ile Leu
                325                 330                 335
Lys Thr His Gly Thr Lys Asp Lys Gly Ala Lys Glu Leu Glu Glu Leu
            340                 345                 350
Phe Lys Ser Leu Glu Ser Leu Ser Lys Ala Ala Gln Ala Ala Leu Thr
            355                 360                 365
Asn Ser Val Lys Glu Leu Thr Asn Pro Val Val Ala Glu Ser Pro Lys
            370                 375                 380
Lys Pro
385
```

<210> 59
<211> 1197
<212> DNA
<213> ospC Chimera

<220>
<221> CDS
<222> (1)...(1197)

<400> 59

```
Lys Leu Lys Glu Lys His Thr Asp Leu Gly Lys Glu Gly Val Thr Asp
145                 150                 155                 160 gct gat gca aaa gaa gcc att tta aaa aca aat ggt act aaa act aaa    528
Ala Asp Ala Lys Glu Ala Ile Leu Lys Thr Asn Gly Thr Lys Thr Lys
                165                 170                 175 ggt gct gaa gaa ctt gga aaa tta ttt gaa tca gta gag gtc ttg tca    576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc    624
Lys Ala Ala Lys Glu Met Leu Ala Asn Ser Val Lys Glu Leu Thr Ser
        195                 200                 205 cct gtt gtg gca gaa agt cca gcc atg gta aat aat tca ggg aaa gat    672
Pro Val Val Ala Glu Ser Pro Ala Met Val Asn Asn Ser Gly Lys Asp
    210                 215                 220 ggg aat aca tct gca aat tct gct gat gag tct gtt aaa ggg cct aat    720
Gly Asn Thr Ser Ala Asn Ser Ala Asp Glu Ser Val Lys Gly Pro Asn
225                 230                 235                 240 ctt aca gaa ata agt aaa aaa att aca gaa tct aac gca gtt gtt ctc    768
Leu Thr Glu Ile Ser Lys Lys Ile Thr Glu Ser Asn Ala Val Val Leu
                245                 250                 255 gcc gtg aaa gaa gtt gaa act ttg ctt aca tct ata gat gag ctt gct    816
Ala Val Lys Glu Val Glu Thr Leu Leu Thr Ser Ile Asp Glu Leu Ala
            260                 265                 270 aaa gct att ggt aaa aaa ata aaa aac gat gtt agt tta gat aat gag    864
Lys Ala Ile Gly Lys Lys Ile Lys Asn Asp Val Ser Leu Asp Asn Glu
        275                 280                 285 gca gat cac aac gga tca tta ata tca gga gca tat tta att tca aac    912
Ala Asp His Asn Gly Ser Leu Ile Ser Gly Ala Tyr Leu Ile Ser Asn
    290                 295                 300 tta ata aca aaa aaa ata agt gca ata aaa gat tca gga gaa ttg aag    960
Leu Ile Thr Lys Lys Ile Ser Ala Ile Lys Asp Ser Gly Glu Leu Lys
305                 310                 315                 320 gca gaa att gaa aag gct aag aaa tgt tct gaa gaa ttt act gct aaa   1008
Ala Glu Ile Glu Lys Ala Lys Lys Cys Ser Glu Glu Phe Thr Ala Lys
                325                 330                 335
```

```
tta aaa ggt gaa cac aca gat ctt ggt aaa gaa ggc gtt act gat gat    1056
Leu Lys Gly Glu His Thr Asp Leu Gly Lys Glu Gly Val Thr Asp Asp
            340                 345                 350 aat gca aaa aaa gcc att tta aaa aca aat aat gat aaa act aag ggc    1104
Asn Ala Lys Lys Ala Ile Leu Lys Thr Asn Asn Asp Lys Thr Lys Gly
            355                 360                 365 gct gat gaa ctt gaa aag tta ttt gaa tca gta aaa aac ttg tca aaa    1152
Ala Asp Glu Leu Glu Lys Leu Phe Glu Ser Val Lys Asn Leu Ser Lys
370                 375                 380 gca gct aaa gag atg ctt act aat tca gtt aaa gag ctt aca agc        1197
Ala Ala Lys Glu Met Leu Thr Asn Ser Val Lys Glu Leu Thr Ser
385                 390                 395

<210> 60
<211> 399
<212> PRT
<213> ospC Chimera

<400> 60
Met Arg Leu Leu Ile Gly Phe Ala Leu Ala Leu Ala Leu Ile Gly Cys
1               5                   10                  15
Ala Gln Lys Gly Ala Glu Ser Ile Gly Ser Cys Asn Asn Ser Gly Lys
                20                  25                  30
Asp Gly Asn Thr Ser Ala Asn Ser Ala Asp Glu Ser Val Lys Gly Pro
            35                  40                  45
Asn Leu Thr Glu Ile Ser Lys Lys Ile Thr Asp Ser Asn Ala Val Leu
        50                  55                  60
Leu Ala Val Lys Glu Val Glu Ala Leu Leu Ser Ser Ile Asp Glu Ile
65                  70                  75                  80
Ala Ala Lys Ala Ile Gly Lys Lys Ile His Gln Asn Asn Gly Leu Asp
                85                  90                  95
Thr Glu Tyr Asn His Asn Gly Ser Leu Leu Ala Gly Ala Tyr Ala Ile
                100                 105                 110
Ser Thr Leu Ile Lys Gln Lys Leu Asp Gly Leu Lys Asn Glu Gly Leu
            115                 120                 125
Lys Glu Lys Ile Asp Ala Ala Lys Lys Cys Ser Glu Thr Phe Thr Asn
        130                 135                 140
Lys Leu Lys Glu Lys His Thr Asp Leu Gly Lys Glu Gly Val Thr Asp
145                 150                 155                 160
Ala Asp Ala Lys Glu Ala Ile Leu Lys Thr Asn Gly Thr Lys Thr Lys
                165                 170                 175
Gly Ala Glu Glu Leu Gly Lys Leu Phe Glu Ser Val Glu Val Leu Ser
            180                 185                 190
```

```
Lys Ala Ala Lys Glu Met Leu Ala Asn Ser Val Lys Glu Leu Thr Ser
        195                 200                 205
Pro Val Val Ala Glu Ser Pro Ala Met Val Asn Asn Ser Gly Lys Asp
210                 215                 220
Gly Asn Thr Ser Ala Asn Ser Ala Asp Glu Ser Val Lys Gly Pro Asn
225                 230                 235                 240
Leu Thr Glu Ile Ser Lys Lys Ile Thr Glu Ser Asn Ala Val Val Leu
                245                 250                 255
Ala Val Lys Glu Val Glu Thr Leu Leu Thr Ser Ile Asp Glu Leu Ala
            260                 265                 270
Lys Ala Ile Gly Lys Lys Ile Lys Asn Asp Val Ser Leu Asp Asn Glu
            275                 280                 285
Ala Asp His Asn Gly Ser Leu Ile Ser Gly Ala Tyr Leu Ile Ser Asn
        290                 295                 300
Leu Ile Thr Lys Lys Ile Ser Ala Ile Lys Asp Ser Gly Glu Leu Lys
305                 310                 315                 320
Ala Glu Ile Glu Lys Ala Lys Lys Cys Ser Glu Glu Phe Thr Ala Lys
                325                 330                 335
Leu Lys Gly Glu His Thr Asp Leu Gly Lys Glu Gly Val Thr Asp Asp
            340                 345                 350
Asn Ala Lys Lys Ala Ile Leu Lys Thr Asn Asn Asp Lys Thr Lys Gly
            355                 360                 365
Ala Asp Glu Leu Glu Lys Leu Phe Glu Ser Val Lys Asn Leu Ser Lys
        370                 375                 380
Ala Ala Lys Glu Met Leu Thr Asn Ser Val Lys Glu Leu Thr Ser
385                 390                 395

<210> 61
<211> 1196
<212> DNA
<213> ospC Chimera

<220>
<221> CDS
<222> (1)...(1196)

<400> 61
atg aga tta tta ata gga ttt gct tta gcg tta gct tta ata gga tgt    48
Met Arg Leu Leu Ile Gly Phe Ala Leu Ala Leu Ala Leu Ile Gly Cys
1               5                   10                  15 gca caa aaa ggt gct gag tca att gga tcc tgt aat aat tca ggg aaa    96
Ala Gln Lys Gly Ala Glu Ser Ile Gly Ser Cys Asn Asn Ser Gly Lys
            20                  25                  30
```

```
gat ggg aat aca tct gca aat tct gct gat gag tct gtt aaa ggg cct    144
Asp Gly Asn Thr Ser Ala Asn Ser Ala Asp Glu Ser Val Lys Gly Pro
         35                  40                  45 aat ctt aca gaa ata agt aaa aaa att acg gat tct aat gcg gtt tta    192
Asn Leu Thr Glu Ile Ser Lys Lys Ile Thr Asp Ser Asn Ala Val Leu
 50                  55                  60 ctt gct gtg aaa gag gtt gaa gcg ttg ctg tca tct ata gat gaa att    240
Leu Ala Val Lys Glu Val Glu Ala Leu Leu Ser Ser Ile Asp Glu Ile
 65                  70                  75                  80 gct gct aaa gct att ggt aaa aaa ata cac caa aat aat ggt ttg gat    288
Ala Ala Lys Ala Ile Gly Lys Lys Ile His Gln Asn Asn Gly Leu Asp
             85                  90                  95 acc gaa tat aat cac aat gga tca ttg tta gcg gga gct tat gca ata    336
Thr Glu Tyr Asn His Asn Gly Ser Leu Leu Ala Gly Ala Tyr Ala Ile
            100                 105                 110 tca acc cta ata aaa caa aaa tta gat gga ttg aaa aat gaa gga tta    384
Ser Thr Leu Ile Lys Gln Lys Leu Asp Gly Leu Lys Asn Glu Gly Leu
        115                 120                 125 aag gaa aaa att gat gcg gct aag aaa tgt tct gaa aca ttt act aat    432
Lys Glu Lys Ile Asp Ala Ala Lys Lys Cys Ser Glu Thr Phe Thr Asn
130                 135                 140 aaa tta aaa gaa aaa cac aca gat ctt ggt aaa gaa ggt gtt act gat    480
Lys Leu Lys Glu Lys His Thr Asp Leu Gly Lys Glu Gly Val Thr Asp
145                 150                 155                 160 gct gat gca aaa gaa gcc att tta aaa aca aat ggt act aaa act aaa    528
Ala Asp Ala Lys Glu Ala Ile Leu Lys Thr Asn Gly Thr Lys Thr Lys
                165                 170                 175 ggt gct gaa gaa ctt gga aaa tta ttt gaa tca gta gag gtc ttg tca    576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc    624
Lys Ala Ala Lys Glu Met Leu Ala Asn Ser Val Lys Glu Leu Thr Ser
        195                 200                 205 cct gtt gtg gca gaa agt cca gcc atg gta aat aat tca gga aaa gat    672
Pro Val Val Ala Glu Ser Pro Ala Met Val Asn Asn Ser Gly Lys Asp
    210                 215                 220
```

```
ggg aat aca tct gca aat tct gct gat gag tct gtt aaa ggg cct aat      720
Gly Asn Thr Ser Ala Asn Ser Ala Asp Glu Ser Val Lys Gly Pro Asn
225                 230                 235                 240 ctt aca gaa ata agt aaa aaa att aca gaa tct aac gca gtt gtt ctg      768
Leu Thr Glu Ile Ser Lys Lys Ile Thr Glu Ser Asn Ala Val Val Leu
                245                 250                 255 gct gtg aaa gaa att gaa act ttg ctt gca tct ata gat gaa ctt gct      816
Ala Val Lys Glu Ile Glu Thr Leu Leu Ala Ser Ile Asp Glu Leu Ala
            260                 265                 270 act aaa gct att ggt aaa aaa ata caa caa aat ggt ggt tta gct gtc      864
Thr Lys Ala Ile Gly Lys Lys Ile Gln Gln Asn Gly Gly Leu Ala Val
        275                 280                 285 gaa gcg ggg cat aat gga aca ttg tta gca ggt gct tat aca ata tca      912
Glu Ala Gly His Asn Gly Thr Leu Leu Ala Gly Ala Tyr Thr Ile Ser
    290                 295                 300 aaa cta ata aca caa aaa tta gat gga ttg aaa aat tca gaa aaa tta      960
Lys Leu Ile Thr Gln Lys Leu Asp Gly Leu Lys Asn Ser Glu Lys Leu
305                 310                 315                 320 aag gaa aaa att gaa aat gct aag aaa tgt tct gaa gat ttt act aaa     1008
Lys Glu Lys Ile Glu Asn Ala Lys Lys Cys Ser Glu Asp Phe Thr Lys
                325                 330                 335 aaa cta gaa gga gaa cat gcg caa ctt gga att gaa aat gtt act gat     1056
Lys Leu Glu Gly Glu His Ala Gln Leu Gly Ile Glu Asn Val Thr Asp
            340                 345                 350 gag aat gca aaa aaa gct att tta ata aca gat gca gct aaa gat aag     1104
Glu Asn Ala Lys Lys Ala Ile Leu Ile Thr Asp Ala Ala Lys Asp Lys
        355                 360                 365 ggc gct gca gag ctt gaa aag cta ttt aaa gca gta gaa aac ttg gca     1152
Gly Ala Ala Glu Leu Glu Lys Leu Phe Lys Ala Val Glu Asn Leu Ala
    370                 375                 380 aaa gca gct aaa gag atg ctt gct aat tca gtt aaa gag ctt ac          1196
Lys Ala Ala Lys Glu Met Leu Ala Asn Ser Val Lys Glu Leu
385                 390                 395
```

<210> 62
<211> 398
<212> PRT
<213> ospC Chimera

<400> 62

```
Met Arg Leu Leu Ile Gly Phe Ala Leu Ala Leu Ala Leu Ile Gly Cys
1               5                   10                  15
Ala Gln Lys Gly Ala Glu Ser Ile Gly Ser Cys Asn Asn Ser Gly Lys

```
Lys Glu Lys Ile Glu Asn Ala Lys Lys Cys Ser Glu Asp Phe Thr Lys
                325                 330                 335
Lys Leu Glu Gly Glu His Ala Gln Leu Gly Ile Glu Asn Val Thr Asp
            340                 345                 350
Glu Asn Ala Lys Lys Ala Ile Leu Ile Thr Asp Ala Ala Lys Asp Lys
            355                 360                 365
Gly Ala Ala Glu Leu Glu Lys Leu Phe Lys Ala Val Glu Asn Leu Ala
    370                 375                 380
Lys Ala Ala Lys Glu Met Leu Ala Asn Ser Val Lys Glu Leu
385                 390                 395

<210> 63
<211> 1185
<212> DNA
<213> ospC Chimera

<220>
<221> CDS
<222> (1)...

```
gaa gca aat cgc aac gag tca ttg tta gca gga gct tat aca ata tca   336
Glu Ala Asn Arg Asn Glu Ser Leu Leu Ala Gly Ala Tyr Thr Ile Ser
            100             105             110 acc tta ata aca caa aaa tta agt aaa tta aac gga tca gaa ggt tta   384
Thr Leu Ile Thr Gln Lys Leu Ser Lys Leu Asn Gly Ser Glu Gly Leu
            115             120             125 aag gaa aag att gcc gca gct aag aaa tgc tct gaa gag ttt agt act   432
Lys Glu Lys Ile Ala Ala Ala Lys Lys Cys Ser Glu Glu Phe Ser Thr
130             135             140 aaa cta aaa gat aat cat gca cag ctt ggt ata cag ggc gtt act gat   480
Lys Leu Lys Asp Asn His Ala Gln Leu Gly Ile Gln Gly Val Thr Asp
145             150             155             160 gaa aat gca aaa aaa gct att tta aaa gca aat gca gcg ggt aaa gat   528
Glu Asn Ala Lys Lys Ala Ile Leu Lys Ala Asn Ala Ala Gly Lys Asp
            165             170             175 aag ggc gtt gaa gaa ctt gaa aag ttg tcc gga tca tta gaa agc tta   576
Lys Gly Val Glu Glu Leu Glu Lys Leu Ser Gly Ser Leu Glu Ser Leu
            180             185             190 tca aaa gca gct aaa gag atg ctt gct aat tca gtt aaa gag ctt aca   624
Ser Lys Ala Ala Lys Glu Met Leu Ala Asn Ser Val Lys Glu Leu Thr
            195             200             205 agc cct gtt gtc cat ggt aat aat tca ggg aaa gat ggg aat aca tct   672
Ser Pro Val Val His Gly Asn Asn Ser Gly Lys Asp Gly Asn Thr Ser
            210             215             220 gca aat tct gct gat gag tct gtt aaa ggg cct aat ctt aca gaa ata   720
Ala Asn Ser Ala Asp Glu Ser Val Lys Gly Pro Asn Leu Thr Glu Ile
225             230             235             240 agt aaa aaa att aca gaa tct aac gca gtt gtt ctc gcc gtg aaa gaa   768
Ser Lys Lys Ile Thr Glu Ser Asn Ala Val Val Leu Ala Val Lys Glu
            245             250             255 gtt gaa act ttg ctt aca tct ata gat gag ctt gct aaa gct att ggt   816
Val Glu Thr Leu Leu Thr Ser Ile Asp Glu Leu Ala Lys Ala Ile Gly
            260             265             270 aaa aaa ata aaa aac gat gtt agt tta gat aat gag gca gat cac aac   864
```

```
                Lys Lys Ile Lys Asn Asp Val Ser Leu Asp Asn Glu Ala Asp His Asn
                        275                 280                 285 gga tca tta ata tca gga gca tat tta att tca aac tta ata aca aaa     912
Gly Ser Leu Ile Ser Gly Ala Tyr Leu Ile Ser Asn Leu Ile Thr Lys
        290                 295                 300 aaa ata agt gca ata aaa gat tca gga gaa ttg aag gca gaa att gaa     960
Lys Ile Ser Ala Ile Lys Asp Ser Gly Glu Leu Lys Ala Glu Ile Glu
305                 310                 315                 320 aag gct aag aaa tgt tct gaa gaa ttt act gct aaa tta aaa ggt gaa     1008
Lys Ala Lys Lys Cys Ser Glu Glu Phe Thr Ala Lys Leu Lys Gly Glu
                325                 330                 335 cac aca gat ctt ggt aaa gaa ggc gtt act gat gat aat gca aaa aaa     1056
His Thr Asp Leu Gly Lys Glu Gly Val Thr Asp Asp Asn Ala Lys Lys
        340                 345                 350 gcc att tta aaa aca aat aat gat aaa act aag ggc gct gat gaa ctt     1104
Ala Ile Leu Lys Thr Asn Asn Asp Lys Thr Lys Gly Ala Asp Glu Leu
        355                 360                 365 gaa aag tta ttt gaa tca gta aaa aac ttg tca aaa gca gct aaa gag     1152
Glu Lys Leu Phe Glu Ser Val Lys Asn Leu Ser Lys Ala Ala Lys Glu
        370                 375                 380 atg ctt act aat tca gtt aaa gag ctt aca agc                         1185
Met Leu Thr Asn Ser Val Lys Glu Leu Thr Ser
385                 390                 395

<210> 64
<211> 395
<212> PRT
<213> ospC Chimera

<400> 64
Met Arg Leu Leu Ile Gly Phe Ala Leu Ala Leu Ala Leu Ile Gly Cys
1               5                   10                  15
Ala G

```
Leu Ala Val Lys Glu Val Glu Ala Leu Leu Ser Ser Ile Asp Glu Leu
65                  70                  75                  80
Ala Lys Ala Ile Gly Lys Lys Ile Lys Asn Asp Gly Ser Leu Asp Asn
                85                  90                  95
Glu Ala Asn Arg Asn Glu Ser Leu Leu Ala Gly Ala Tyr Thr Ile Ser
                100                 105                 110
Thr Leu Ile Thr Gln Lys Leu Ser Lys Leu Asn Gly Ser Glu Gly Leu
                115                 120                 125
Lys Glu Lys Ile Ala Ala Ala Lys Lys Cys Ser Glu Glu Phe Ser Thr
130                 135                 140
Lys Leu Lys Asp Asn His Ala Gln Leu Gly Ile Gln Gly Val Thr Asp
145                 150                 155                 160
Glu Asn Ala Lys Lys Ala Ile Leu Lys Ala Asn Ala Ala Gly Lys Asp
                165                 170                 175
Lys Gly Val Glu Glu Leu Glu Lys Leu Ser Gly Ser Leu Glu Ser Leu
                180                 185                 190
Ser Lys Ala Ala Lys Glu Met Leu Ala Asn Ser Val Lys Glu Leu Thr
                195                 200                 205
Ser Pro Val Val His Gly Asn Asn Ser Gly Lys Asp Gly Asn Thr Ser
210                 215                 220
Ala Asn Ser Ala Asp Glu Ser Val Lys Gly Pro Asn Leu Thr Glu Ile
225                 230                 235                 240
Ser Lys Lys Ile Thr Glu Ser Asn Ala Val Val Leu Ala Val Lys Glu
                245                 250                 255
Val Glu Thr Leu Leu Thr Ser Ile Asp Glu Leu Ala Lys Ala Ile Gly
                260                 265                 270
Lys Lys Ile Lys Asn Asp Val Ser Leu Asp Asn Glu Ala Asp His Asn
275                 280                 285
Gly Ser Leu Ile Ser Gly Ala Tyr Leu Ile Ser Asn Leu Ile Thr Lys
290                 295                 300
Lys Ile Ser Ala Ile Lys Asp Ser Gly Glu Leu Lys Ala Glu Ile Glu
305                 310                 315                 320
Lys Ala Lys Lys Cys Ser Glu Glu Phe Thr Ala Lys Leu Lys Gly Glu
                325                 330                 335
His Thr Asp Leu Gly Lys Glu Gly Val Thr Asp Asp Asn Ala Lys Lys
                340                 345                 350
Ala Ile Leu Lys Thr Asn Asn Asp Lys Thr Lys Gly Ala Asp Glu Leu
                355                 360                 365
Glu Lys Leu Phe Glu Ser Val Lys Asn Leu Ser Lys Ala Ala Lys Glu
370                 375                 380
Met Leu Thr Asn Ser Val Lys Glu Leu Thr Ser
385                 390                 395
```

<210> 65
<211> 1184
<212> DNA
<213> ospC Chimera

<220>
<221> CDS
<222> (1)...(1184)

<400> 65

|

```
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat    528
Glu Asn Ala Lys Lys Ala Ile Leu Lys Ala Asn Ala Ala Gly Lys Asp
                165                 170                 175 aag ggc gtt gaa gaa ctt gaa aag ttg tcc gga tca tta gaa agc tta    576
Lys Gly Val Glu Glu Leu Glu Lys Leu Ser Gly Ser Leu Glu Ser Leu
            180                 185                 190 tca aaa gca gct aaa gag atg ctt gct aat tca gtt aaa gag ctt aca    624
Ser Lys Ala Ala Lys Glu Met Leu Ala Asn Ser Val Lys Glu Leu Thr
        195                 200                 205 agc cct gtt gtc cat ggt aat aat tca gga aaa gat ggg aat aca tct    672
Ser Pro Val Val His Gly Asn Asn Ser Gly Lys Asp Gly Asn Thr Ser
    210                 215                 220 gca aat tct gct gat gag tct gtt aaa ggg cct aat ctt aca gaa ata    720
Ala Asn Ser Ala Asp Glu Ser Val Lys Gly Pro Asn Leu Thr Glu Ile
225                 230                 235                 240 agt aaa aaa att aca gaa tct aac gca gtt gtt ctg gct gtg aaa gaa    768
Ser Lys Lys Ile Thr Glu Ser Asn Ala Val Val Leu Ala Val Lys Glu
                245                 250                 255 att gaa act ttg ctt gca tct ata gat gaa ctt gct act aaa gct att    816
Ile Glu Thr Leu Leu Ala Ser Ile Asp Glu Leu Ala Thr Lys Ala Ile
                260                 265                 270 ggt aaa aaa ata caa caa aat ggt ggt tta gct gtc gaa gcg ggg cat    864
Gly Lys Lys Ile Gln Gln Asn Gly Gly Leu Ala Val Glu Ala Gly His
        275                 280                 285 aat gga aca ttg tta gca ggt gct tat aca ata tca aaa cta ata aca    912
Asn Gly Thr Leu Leu Ala Gly Ala Tyr Thr Ile Ser Lys Leu Ile Thr
    290                 295                 300 caa aaa tta gat gga ttg aaa aat tca gaa aaa tta aag gaa aaa att    960
Gln Lys Leu Asp Gly Leu Lys Asn Ser Glu Lys Leu Lys Glu Lys Ile
305                 310                 315                 320 gaa aat gct aag aaa tgt tct gaa gat ttt act aaa aaa cta gaa gga   1008
Glu Asn Ala Lys Lys Cys Ser Glu Asp Phe Thr Lys Lys Leu Glu Gly
                325                 330                 335
```

```
gaa cat gcg caa ctt gga att gaa aat gtt act gat gag aat gca aaa      1056
Glu His Ala Gln Leu Gly Ile Glu Asn Val Thr Asp Glu Asn Ala Lys
            340                 345                 350 aaa gct att tta ata aca gat gca gct aaa gat aag ggc gct gca gag      1104
Lys Ala Ile Leu Ile Thr Asp Ala Ala Lys Asp Lys Gly Ala Ala Glu
            355                 360                 365 ctt gaa aag cta ttt aaa gca gta gaa aac ttg gca aaa gca gct aaa      1152
Leu Glu Lys Leu Phe Lys Ala Val Glu Asn Leu Ala Lys Ala Ala Lys
            370                 375                 380 gag atg ctt gct aat tca gtt aaa gag ctt ac                           1184
Glu Met Leu Ala Asn Ser Val Lys Glu Leu
385                 390

<210> 66
<211> 394
<212> PRT
<213> ospC Chimera

<400> 66
Met Arg Leu Leu Ile Gly Phe Ala Leu Ala Leu Ala Leu Ile Gly Cys
1               5                   10                  15
Ala Gln Lys Gly Ala Glu Ser Ile Gly Ser Cys Asn Asn Ser Gly Lys
                20                  25                  30
Asp Gly As

```
Lys Gly Val Glu Glu Leu Glu Lys Leu Ser Gly Ser Leu Glu Ser Leu
            180                 185                 190
Ser Lys Ala Ala Lys Glu Met Leu Ala Asn Ser Val Lys Glu Leu Thr
            195                 200                 205
Ser Pro Val Val His Gly Asn Asn Ser Gly Lys Asp Gly Asn Thr Ser
            210                 215                 220
Ala Asn Ser Ala Asp Glu Ser Val Lys Gly Pro Asn Leu Thr Glu Ile
225                 230                 235                 240
Ser Lys Lys Ile Thr Glu Ser Asn Ala Val Val Leu Ala Val Lys Glu
            245                 250                 255
Ile Glu Thr Leu Leu Ala Ser Ile Asp Glu Leu Ala Thr Lys Ala Ile
            260                 265                 270
Gly Lys Lys Ile Gln Gln Asn Gly Gly Leu Ala Val Glu Ala Gly His
            275                 280                 285
Asn Gly Thr Leu Leu Ala Gly Ala Tyr Thr Ile Ser Lys Leu Ile Thr
            290                 295                 300
Gln Lys Leu Asp Gly Leu Lys Asn Ser Glu Lys Leu Lys Glu Lys Ile
305                 310                 315                 320
Glu Asn Ala Lys Lys Cys Ser Glu Asp Phe Thr Lys Lys Leu Glu Gly
            325                 330                 335
Glu His Ala Gln Leu Gly Ile Glu Asn Val Thr Asp Glu Asn Ala Lys
            340                 345                 350
Lys Ala Ile Leu Ile Thr Asp Ala Ala Lys Asp Lys Gly Ala Ala Glu
            355                 360                 365
Leu Glu Lys Leu Phe Lys Ala Val Glu Asn Leu Ala Lys Ala Ala Lys
            370                 375                 380
Glu Met Leu Ala Asn Ser Val Lys Glu Leu
385                 390

<210> 67
<211> 1184
<212> DNA
<213> ospC Chimera

<220>
<221> CDS
<222> (1)...(1184)

<400>

```
gat ggg aat aca tct gca aat tct gct gat gag tct gtt aaa ggg cct    144
Asp Gly Asn Thr Ser Ala Asn Ser Ala Asp Glu Ser Val Lys Gly Pro
         35                  40                  45 aat ctt aca gaa ata agt aaa aaa att acg gat tct aat gcg gtt tta    192
Asn Leu Thr Glu Ile Ser Lys Lys Ile Thr Asp Ser Asn Ala Val Leu
     50                  55                  60 ctt gct gtg aaa gag gtt gaa gcg ttg ctg tca tct ata gat gag ctt    240
Leu Ala Val Lys Glu Val Glu Ala Leu Leu Ser Ser Ile Asp Glu Leu
 65                  70                  75                  80 gct aaa gct att ggt aaa aaa ata aaa aac gat ggt agt tta gat aat    288
Ala Lys Ala Ile Gly Lys Lys Ile Lys Asn Asp Gly Ser Leu Asp Asn
                 85                  90                  95 gaa gca aat cgc aac gag tca ttg tta gca gga gct tat aca ata tca    336
Glu Ala Asn Arg Asn Glu Ser Leu Leu Ala Gly Ala Tyr Thr Ile Ser
             100                 105                 110 acc tta ata aca caa aaa tta agt aaa tta aac gga tca gaa ggt tta    384
Thr Leu Ile Thr Gln Lys Leu Ser Lys Leu Asn Gly Ser Glu Gly Leu
         115                 120                 125 aag gaa aag att gcc gca gct aag aaa tgc tct gaa gag ttt agt act    432
Lys Glu Lys Ile Ala Ala Ala Lys Lys Cys Ser Glu Glu Phe Ser Thr
 130                 135                 140 aaa cta aaa gat aat cat gca cag ctt ggt ata cag ggc gtt act gat    480
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat    528
Glu Asn Ala Lys Lys Ala Ile Leu Lys Ala Asn Ala Ala Gly Lys Asp
                 165                 170                 175 aag ggc gtt gaa gaa ctt gaa aag ttg tcc gga tca tta gaa agc tta    576
Lys Gly Val Glu Glu Leu Glu Lys Leu Ser Gly Ser Leu Glu Ser Leu
             180                 185                 190 tca aaa gca gct aaa gag atg ctt gct aat tca gtt aaa gag ctt aca    624
Ser Lys Ala Ala Lys Glu Met Leu Ala Asn Ser Val Lys Glu Leu Thr
         195                 200                 205
```

```
agc cct gtt gtc cat ggt aat aat tca aga aaa gat ggg aat gca tct    672
Ser Pro Val Val His Gly Asn Asn Ser Arg Lys Asp Gly Asn Ala Ser
    210             215                 220 aca aat tct gcc gat gag tct gtt aaa ggg cct aat ctt aca gaa ata    720
Thr Asn Ser Ala Asp Glu Ser Val Lys Gly Pro Asn Leu Thr Glu Ile
225             230                 235                 240 agt aaa aaa att aca gaa tct aac gca gtt gtt ctg gcc gtg aaa gaa    768
Ser Lys Lys Ile Thr Glu Ser Asn Ala Val Val Leu Ala Val Lys Glu
            245                 250                 255 gtt gag acc tta ctt gca tct ata gat gaa ctt gct acc aaa gct att    816
Val Glu Thr Leu Leu Ala Ser Ile Asp Glu Leu Ala Thr Lys Ala Ile
        260                 265                 270 ggt aag aaa ata ggc aat aat ggt tta gag gcc aat cag agt aaa aac    864
Gly Lys Lys Ile Gly Asn Asn Gly Leu Glu Ala Asn Gln Ser Lys Asn
    275                 280                 285 aca tca ttg tta tca gga gct tat gca ata tct gac cta ata gca gaa    912
Thr Ser Leu Leu Ser Gly Ala Tyr Ala Ile Ser Asp Leu Ile Ala Glu
290             295                 300 aaa tta aat gta ttg aaa aat gaa gaa tta aag gaa aag att gat aca    960
Lys Leu Asn Val Leu Lys Asn Glu Glu Leu Lys Glu Lys Ile Asp Thr
305             310                 315                 320 gct aag caa tgt tct aca gaa ttt act aat aaa cta aaa agt gaa cat   1008
Ala Lys Gln Cys Ser Thr Glu Phe Thr Asn Lys Leu Lys Ser Glu His
            325                 330                 335 gca gtg ctt ggt ctg gac aat ctt act gat gat aat gca caa aga gct   1056
Ala Val Leu Gly Leu Asp Asn Leu Thr Asp Asp Asn Ala Gln Arg Ala
        340                 345                 350 att tta aaa aaa cat gca aat aaa gat aag ggt gct gca gaa ctt gaa   1104
Ile Leu Lys Lys His Ala Asn Lys Asp Lys Gly Ala Ala Glu Leu Glu
    355                 360                 365 aag tta ttt aaa gcg gta gaa aac tta tca aaa gca gct caa gac aca   1152
Lys Leu Phe Lys Ala Val Glu Asn Leu Ser Lys Ala Ala Gln Asp Thr
370             375                 380 tta aaa aat gct gtt aaa gag ctt aca agt cc                        1184
Leu Lys Asn Ala Val Lys Glu Leu Thr Ser
385             390
```

<210> 68
<211> 394
<212> PRT
<213> ospC Chimera

<400> 68

```
Met Arg Leu Leu Ile Gly Phe Ala Leu Ala Leu Ile Gly Cys
 1               5                  10                  15
Ala Gln Lys Gly Ala Glu Ser Ile Gly Ser Cys Asn Asn Ser Gly Lys
            20                  25                  30
Asp Gly Asn Thr Ser Ala Asn Ser Ala Asp Glu Ser Val Lys Gly Pro
            35                  40                  45
Asn Leu Thr Glu Ile Ser Lys Lys Ile Thr Asp Ser Asn Ala Val Leu
            50                  55                  60
Leu Ala Val Lys Glu Val Glu Ala Leu Leu Ser Ser Ile Asp Glu Leu
65                  70                  75                  80
Ala Lys Ala Ile Gly Lys Lys Ile Lys Asn Asp Gly Ser Leu Asp Asn
                85                  90                  95
Glu Ala Asn Arg Asn Glu Ser Leu Leu Ala Gly Ala Tyr Thr Ile Ser
            100                 105                 110
Thr Leu Ile Thr Gln Lys Leu Ser Lys Leu Asn Gly Ser Glu Gly Leu
            115                 120                 125
Lys Glu Lys Ile Ala Ala Ala Lys Lys Cys Ser Glu Glu Phe Ser Thr
130                 135                 140
Lys Leu Lys Asp Asn His Ala Gln Leu Gly Ile Gln Gly Val Thr Asp
145                 150                 155                 160
Glu Asn Ala Lys Lys Ala Ile Leu Lys Ala Asn Ala Ala Gly Lys Asp
                165                 170                 175
Lys Gly Val Glu Glu Leu Glu Lys Leu Ser Gly Ser Leu Glu Ser Leu
            180                 185                 190
Ser Lys Ala Ala Lys Glu Met Leu Ala Asn Ser Val Lys Glu Leu Thr
            195                 200                 205
Ser Pro Val Val His Gly Asn Asn Ser Arg Lys Asp Gly Asn Ala Ser
210                 215                 220
Thr Asn Ser Ala Asp Glu Ser Val Lys Gly Pro Asn Leu Thr Glu Ile
225                 230                 235                 240
Ser Lys Lys Ile Thr Glu Ser Asn Ala Val Val Leu Ala Val Lys Glu
                245                 250                 255
Val Glu Thr Leu Leu Ala Ser Ile Asp Glu Leu Ala Thr Lys Ala Ile
            260                 265                 270
Gly Lys Lys Ile Gly Asn Asn Gly Leu Glu Ala Asn Gln Ser Lys Asn
            275                 280                 285
Thr Ser Leu Leu Ser Gly Ala Tyr Ala Ile Ser Asp Leu Ile Ala Glu
290                 295                 300
```

```
Lys Leu Asn Val Leu Lys Asn Glu Glu Leu Lys Glu Lys Ile Asp Thr
305                 310                 315                 320
Ala Lys Gln Cys Ser Thr Glu Phe Thr Asn Lys Leu Lys Ser Glu His
            325                 330                 335
Ala Val Leu Gly Leu Asp Asn Leu Thr Asp Asp Asn Ala Gln Arg Ala
                340                 345                 350
Ile Leu Lys Lys His Ala Asn Lys Asp Lys Gly Ala Ala Glu Leu Glu
            355                 360                 365
Lys Leu Phe Lys Ala Val Glu Asn Leu Ser Lys Ala Ala Gln Asp Thr
        370                 375                 380
Leu Lys Asn Ala Val Lys Glu Leu Thr Ser
385                 390

<210> 69
<211> 1209
<212> DNA
<213> ospC Chimera

<220>
<221> CDS
<222> (1)...(1209)

<400> 69
atg aga tta tta ata gga ttt gct tta gcg tta gct tta ata gga tgt    48
Met Arg Leu Leu Ile Gly Phe Ala Leu Ala Leu Ala Leu Ile Gly Cys
1

```
gaa gca aat cgc aac gag tca ttg tta gca gga gct tat aca ata tca    336
Glu Ala Asn Arg Asn Glu Ser Leu Leu Ala Gly Ala Tyr Thr Ile Ser
            100                 105                 110 acc tta ata aca caa aaa tta agt aaa tta aac gga tca gaa ggt tta    384
Thr Leu Ile Thr Gln Lys Leu Ser Lys Leu Asn Gly Ser Glu Gly Leu
            115                 120                 125 aag gaa aag att gcc gca gct aag aaa tgc tct gaa gag ttt agt act    432
Lys Glu Lys Ile Ala Ala Ala Lys Lys Cys Ser Glu Glu Phe Ser Thr
    130                 135                 140 aaa cta aaa gat aat cat gca cag ctt ggt ata cag ggc gtt act gat    480
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat    528
Glu Asn Ala Lys Lys Ala Ile Leu Lys Ala Asn Ala Ala Gly Lys Asp
                165                 170                 175 aag ggc gtt gaa gaa ctt gaa aag ttg tcc gga tca tta gaa agc tta    576
Lys Gly Val Glu Glu Leu Glu Lys Leu Ser Gly Ser Leu Glu Ser Leu
            180                 185                 190 tca aaa gca gct aaa gag atg ctt gct aat tca gtt aaa gag ctt aca    624
Ser Lys Ala Ala Lys Glu Met Leu Ala Asn Ser Val Lys Glu Leu Thr
        195                 200                 205 agc cct gtt gtc cat ggt aat aat tca ggt ggg gat tct gca tct act    672
Ser Pro Val Val His Gly Asn Asn Ser Gly Gly Asp Ser Ala Ser Thr
        210.                215                 220 aat cct gat gag tct gca aaa gga cct aat ctt acc gta ata agc aaa    720
Asn Pro Asp Glu Ser Ala Lys Gly Pro Asn Leu Thr Val Ile Ser Lys
225                 230                 235                 240 aaa att aca gat tct aat gca ttt tta ctg gct gtg aaa gaa gtt gag    768
Lys Ile Thr Asp Ser Asn Ala Phe Leu Leu Ala Val Lys Glu Val Glu
                245                 250                 255 gct ttg ctt tca tct ata gat gaa ctt tct aaa gct att ggt aaa aaa    816
Ala Leu Leu Ser Ser Ile Asp Glu Leu Ser Lys Ala Ile Gly Lys Lys
            260                 265                 270
```

```
ata aaa aat gat ggt act tta gat aac gaa gca aat cga aac gaa tca 864
Ile Lys Asn Asp Gly Thr Leu Asp Asn Glu Ala Asn Arg Asn Glu Ser
275 280 285
ttg ata gca gga gct tat gaa ata tca aaa cta ata aca caa aaa tta 912
Leu Ile Ala Gly Ala Tyr Glu Ile Ser Lys Leu Ile Thr Gln Lys Leu
290 295 300
agt gta ttg aat tca gaa gaa tta aag aaa aaa att aaa gag gct aag 960
Ser Val Leu Asn Ser Glu Glu Leu Lys Lys Lys Ile Lys Glu Ala Lys
305 310 315 320
gat tgt tcc caa aaa ttt act act aag cta aaa gat agt cat gca gag 1008
Asp Cys Ser Gln Lys Phe Thr Thr Lys Leu Lys Asp Ser His Ala Glu
325 330 335
ctt ggt ata caa agc gtt cag gat gat aat gca aaa aaa gct att tta 1056
Leu Gly Ile Gln Ser Val Gln Asp Asp Asn Ala Lys Lys Ala Ile Leu
340 345 350
aaa aca cat gga act aaa gac aag ggt gct aaa gaa ctt gaa gag tta 1104
Lys Thr His Gly Thr Lys Asp Lys Gly Ala Lys Glu Leu Glu Glu Leu
355 360 365
ttt aaa tca cta gaa agc ttg tca aaa gca gcg caa gca gca tta act 1152
Phe Lys Ser Leu Glu Ser Leu Ser Lys Ala Ala Gln Ala Ala Leu Thr
370 375 380
aat tca gtt aaa gag ctt aca aat cct gtt gtg gca gaa agt cca aaa 1200
Asn Ser Val Lys Glu Leu Thr Asn Pro Val Val Ala Glu Ser Pro Lys
385 390 395 400
aaa cct taa 1209
Lys Pro *

<210> 70
<211> 402
<212> PRT
<213> ospC Chimera

<400> 70
Met Arg Leu Leu Ile Gly Phe Ala Leu Ala Leu Ala Leu Ile Gly Cys
1 5 10 15
Ala Gln Lys Gly Ala Glu Ser Ile Gly Ser Cys Asn Asn Ser Gly Lys
20 25 30

```
Asp Gly Asn Thr Ser Ala Asn Ser Ala Asp Glu Ser Val Lys Gly Pro
        35                  40                  45
Asn Leu Thr Glu Ile Ser Lys Lys Ile Thr Asp Ser Asn Ala Val Leu
    50                  55                  60
Leu Ala Val Lys Glu Val Glu Ala Leu Leu Ser Ser Ile Asp Glu Leu
65                  70                  75                  80
Ala Lys Ala Ile Gly Lys Lys Ile Lys Asn Asp Gly Ser Leu Asp Asn
                85                  90                  95
Glu Ala Asn Arg Asn Glu Ser Leu Leu Ala Gly Ala Tyr Thr Ile Ser
                100                 105                 110
Thr Leu Ile Thr Gln Lys Leu Ser Lys Leu Asn Gly Ser Glu Gly Leu
            115                 120                 125
Lys Glu Lys Ile Ala Ala Ala Lys Lys Cys Ser Glu Glu Phe Ser Thr
        130                 135                 140
Lys Leu Lys Asp Asn His Ala Gln Leu Gly Ile Gln Gly Val Thr Asp
145                 150                 155                 160
Glu Asn Ala Lys Lys Ala Ile Leu Lys Ala Asn Ala Ala Gly Lys Asp
                165                 170                 175
Lys Gly Val Glu Glu Leu Glu Lys Leu Ser Gly Ser Leu Glu Ser Leu
                180                 185                 190
Ser Lys Ala Ala Lys Glu Met Leu Ala Asn Ser Val Lys Glu Leu Thr
            195                 200                 205
Ser Pro Val Val His Gly Asn Asn Ser Gly Gly Asp Ser Ala Ser Thr
        210                 215                 220
Asn Pro Asp Glu Ser Ala Lys Gly Pro Asn Leu Thr Val Ile Ser Lys
225                 230                 235                 240
Lys Ile Thr Asp Ser Asn Ala Phe Leu Leu Ala Val Lys Glu Val Glu
                245                 250                 255
Ala Leu Leu Ser Ser Ile Asp Glu Leu Ser Lys Ala Ile Gly Lys Lys
                260                 265                 270
Ile Lys Asn Asp Gly Thr Leu Asp Asn Glu Ala Asn Arg Asn Glu Ser
            275                 280                 285
Leu Ile Ala Gly Ala Tyr Glu Ile Ser Lys Leu Ile Thr Gln Lys Leu
        290                 295                 300
Ser Val Leu Asn Ser Glu Glu Leu Lys Lys Lys Ile Lys Glu Ala Lys
305                 310                 315                 320
Asp Cys Ser Gln Lys Phe Thr Thr Lys Leu Lys Asp Ser His Ala Glu
                325                 330                 335
Leu Gly Ile Gln Ser Val Gln Asp Asn Ala Lys Lys Ala Ile Leu
            340                 345                 350
Lys Thr His Gly Thr Lys Asp Lys Gly Ala Lys Glu Leu Glu Glu Leu
        355                 360                 365
Phe Lys Ser Leu Glu Ser Leu Ser Lys Ala Ala Gln Ala Ala Leu Thr
        370                 375                 380
Asn Ser Val Lys Glu Leu Thr Asn Pro Val Val Ala Glu Ser Pro Lys
385                 390                 395                 400
Lys Pro
```

<210> 71
<211> 1179
<212> DNA
<213> ospC Chimera

<220>
<221> CDS
<222> (1)...(1179)

<400> 71

|

```
cta aaa agt gaa cat gca gtg ctt ggt ctg gac aat ctt act gat gat    480
Leu Lys Ser Glu His Ala Val Leu Gly Leu Asp Asn Leu Thr Asp Asp
145             150                 155                 160 aat gca caa aga gct att tta aaa aaa cat gca aat aaa gat aag ggt    528
Asn Ala Gln Arg Ala Ile Leu Lys Lys His Ala Asn Lys Asp Lys Gly
                165                 170                 175 gct gca gaa ctt gaa aag tta ttt aaa gcg gta gaa aac tta tca aaa    576
Ala Ala Glu Leu Glu Lys Leu Phe Lys Ala Val Glu Asn Leu Ser Lys
            180                 185                 190 gca gct caa gac aca tta aaa aat gct gtt aaa gag ctt aca agt cct    624
Ala Ala Gln Asp Thr Leu Lys Asn Ala Val Lys Glu Leu Thr Ser Pro
        195                 200                 205 att gtc cat ggt aat aat tca ggg aaa gat ggg aat aca tct gca aat    672
Ile Val His Gly Asn Asn Ser Gly Lys Asp Gly Asn Thr Ser Ala Asn
    210                 215                 220 tct gct gat gag tct gtt aaa ggg cct aat ctt aca gaa ata agt aaa    720
Ser Ala Asp Glu Ser Val Lys Gly Pro Asn Leu Thr Glu Ile Ser Lys
225             230                 235                 240 aaa att aca gaa tct aac gca gtt gtt ctc gcc gtg aaa gaa gtt gaa    768
Lys Ile Thr Glu Ser Asn Ala Val Val Leu Ala Val Lys Glu Val Glu
                245                 250                 255 act ttg ctt aca tct ata gat gag ctt gct aaa gct att ggt aaa aaa    816
Thr Leu Leu Thr Ser Ile Asp Glu Leu Ala Lys Ala Ile Gly Lys Lys
            260                 265                 270 ata aaa aac gat gtt agt tta gat aat gag gca gat cac aac gga tca    864
Ile Lys Asn Asp Val Ser Leu Asp Asn Glu Ala Asp His Asn Gly Ser
        275                 280                 285 tta ata tca gga gca tat tta att tca aac tta ata aca aaa aaa ata    912
Leu Ile Ser Gly Ala Tyr Leu Ile Ser Asn Leu Ile Thr Lys Lys Ile
    290                 295                 300 agt gca ata aaa gat tca gga gaa ttg aag gca gaa att gaa aag gct    960
Ser Ala Ile Lys Asp Ser Gly Glu Leu Lys Ala Glu Ile Glu Lys Ala
305             310                 315                 320 aag aaa tgt tct gaa gaa ttt act gct aaa tta aaa ggt gaa cac aca   1008
Lys Lys Cys Ser Glu Glu Phe Thr Ala Lys Leu Lys Gly Glu His Thr
                325                 330                 335
```

```
gat ctt ggt aaa gaa ggc gtt act gat gat aat gca aaa aaa gcc att    1056
Asp Leu Gly Lys Glu Gly Val Thr Asp Asp Asn Ala Lys Lys Ala Ile
            340                 345                 350 tta aaa aca aat aat gat aaa act aag ggc gct gat gaa ctt gaa aag    1104
Leu Lys Thr Asn Asn Asp Lys Thr Lys Gly Ala Asp Glu Leu Glu Lys
            355                 360                 365 tta ttt gaa tca gta aaa aac ttg tca aaa gca gct aaa gag atg ctt    1152
Leu Phe Glu Ser Val Lys Asn Leu Ser Lys Ala Ala Lys Glu Met Leu
            370                 375                 380 act aat tca gtt aaa gag ctt aca agc                                1179
Thr Asn Ser Val Lys Glu Leu Thr Ser
385                 390

<210> 72
<211> 393
<212> PRT
<213> ospC Chimera

<400> 72
Met Arg Leu Leu Ile Gly Phe Ala Leu Ala Leu Ala Leu Ile Gly Cys
1               5                   10                  15
Ala Gln Lys Gly Ala Glu Ser Ile Gly Ser Cys Asn Asn Ser Gly Lys
                20

```
Ala Ala Glu Leu Glu Lys Leu Phe Lys Ala Val Glu Asn Leu Ser Lys
        180                 185                 190
Ala Ala Gln Asp Thr Leu Lys Asn Ala Val Lys Glu Leu Thr Ser Pro
        195                 200                 205
Ile Val His Gly Asn Asn Ser Gly Lys Asp Gly Asn Thr Ser Ala Asn
        210                 215                 220
Ser Ala Asp Glu Ser Val Lys Gly Pro Asn Leu Thr Glu Ile Ser Lys
225                 230                 235                 240
Lys Ile Thr Glu Ser Asn Ala Val Val Leu Ala Val Lys Glu Val Glu
                245                 250                 255
Thr Leu Leu Thr Ser Ile Asp Glu Leu Ala Lys Ala Ile Gly Lys Lys
        260                 265                 270
Ile Lys Asn Asp Val Ser Leu Asp Asn Glu Ala Asp His Asn Gly Ser
        275                 280                 285
Leu Ile Ser Gly Ala Tyr Leu Ile Ser Asn Leu Ile Thr Lys Lys Ile
        290                 295                 300
Ser Ala Ile Lys Asp Ser Gly Glu Leu Lys Ala Glu Ile Glu Lys Ala
305                 310                 315                 320
Lys Lys Cys Ser Glu Glu Phe Thr Ala Lys Leu Lys Gly Glu His Thr
                325                 330                 335

Asp Leu Gly Lys Glu Gly Val Thr Asp Asp Asn Ala Lys Lys Ala Ile
        340                 345                 350
Leu Lys Thr Asn Asn Asp Lys Thr Lys Gly Ala Asp Glu Leu Glu Lys
        355                 360                 365
Leu Phe Glu Ser Val Lys Asn Leu Ser Lys Ala Ala Lys Glu Met Leu
        370                 375                 380
Thr Asn Ser Val Lys Glu Leu Thr Ser
385                 390

<210> 73
<211> 1178
<212> DNA
<213> ospC Chimera

<220>
<221> CDS
<222> (1)...(1178)

<400> 73
atg aga tta tta ata gga ttt gct tta gcg tta gct tta ata gga tgt    48
Met Arg Leu Leu Ile Gly Phe Ala Leu Ala Leu Ala Leu Ile Gly Cys
  1               5                  10                  15
```

```
gca caa aaa ggt gct gag tca att gga tcc tgt aat aat tca gga aaa     96
Ala Gln Lys Gly Ala Glu Ser Ile Gly Ser Cys Asn Asn Ser Gly Lys
             20                  25                  30 gat ggg aat gca tct gca aat tct gct gat gag tct gtt aaa ggg cct    144
Asp Gly Asn Ala Ser Ala Asn Ser Ala Asp Glu Ser Val Lys Gly Pro
         35                  40                  45 aat ctt aca gaa ata agt aaa aaa att aca gaa tct aac gca gtt gtt    192
Asn Leu Thr Glu Ile Ser Lys Lys Ile Thr Glu Ser Asn Ala Val Val
     50                  55                  60 ctg gcc gtg aaa gaa gtt gag acc tta ctt gca tct ata gat gaa ctt    240
Leu Ala Val Lys Glu Val Glu Thr Leu Leu Ala Ser Ile Asp Glu Leu
 65                  70                  75                  80 gct acc aaa gct att ggt aaa aaa ata ggc aat aat ggt tta gag gcc    288
Ala Thr Lys Ala Ile Gly Lys Lys Ile Gly Asn Asn Gly Leu Glu Ala
                 85                  90                  95 aat cag agt aaa aac aca tca ttg tta tca gga gct tat gca ata tct    336
Asn Gln Ser Lys Asn Thr Ser Leu Leu Ser Gly Ala Tyr Ala Ile Ser
            100                 105                 110 gac cta ata gca gaa aaa tta aat gta ttg aaa aat gaa gaa tta aag    384
Asp Leu Ile Ala Glu Lys Leu Asn Val Leu Lys Asn Glu Glu Leu Lys
        115                 120                 125 gaa aag att gat aca gct aag caa tgt tct aca gaa ttt act aat aaa    432
Glu Lys Ile Asp Thr Ala Lys Gln Cys Ser Thr Glu Phe Thr Asn Lys
    130                 135                 140 cta aaa agt gaa cat gca gtg ctt ggt ctg gac aat ctt act gat gat    480
Leu Lys Ser Glu His Ala Val Leu Gly Leu Asp Asn Leu Thr Asp Asp
145                 150                 155                 160 aat gca caa aga gct att tta aaa aaa cat gca aat aaa gat aag ggt    528
Asn Ala Gln Arg Ala Ile Leu Lys Lys His Ala Asn Lys Asp Lys Gly
                165                 170                 175 gct gca gaa ctt gaa aag tta ttt aaa gcg gta gaa aac tta tca aaa    576
Ala Ala Glu Leu Glu Lys Leu Phe Lys Ala Val Glu Asn Leu Ser Lys
            180                 185                 190 gca gct caa gac aca tta aaa aat gct gtt aaa gag ctt aca agt cct    624
Ala Ala Gln Asp Thr Leu Lys Asn Ala Val Lys Glu Leu Thr Ser Pro
        195                 200                 205
```

| | | | | | | | | | | | | | | |
|---|---|---|---|---|---|---|---|---|---|---|---|---|---|---|
| att | gtc | cat | ggt | aat | aat | tca | gga | aaa | gat | ggg | aat | aca | tct | gca | aat | 672 |
| Ile | Val | His | Gly | Asn | Asn | Ser | Gly | Lys | Asp | Gly | Asn | Thr | Ser | Ala | Asn | |
| | | 210 | | | | 215 | | | | 220 | | | | | | |

| tct | gct | gat | gag | tct | gtt | aaa | ggg | cct | aat | ctt | aca | gaa | ata | agt | aaa | 720 |
| Ser | Ala | Asp | Glu | Ser | Val | Lys | Gly | Pro | Asn | Leu | Thr | Glu | Ile | Ser | Lys | |
| 225 | | | | | 230 | | | | | 235 | | | | | 240 | |

| aaa | att | aca | gaa | tct | aac | gca | gtt | gtt | ctg | gct | gtg | aaa | gaa | att | gaa | 768 |
| Lys | Ile | Thr | Glu | Ser | Asn | Ala | Val | Val | Leu | Ala | Val | Lys | Glu | Ile | Glu | |
| | | | | 245 | | | | | 250 | | | | | 255 | | |

| act | ttg | ctt | gca | tct | ata | gat | gaa | ctt | gct | act | aaa | gct | att | ggt | aaa | 816 |
| Thr | Leu | Leu | Ala | Ser | Ile | Asp | Glu | Leu | Ala | Thr | Lys | Ala | Ile | Gly | Lys | |
| | | | 260 | | | | | 265 | | | | | 270 | | | |

| aaa | ata | caa | caa | aat | ggt | ggt | tta | gct | gtc | gaa | gcg | ggg | cat | aat | gga | 864 |
| Lys | Ile | Gln | Gln | Asn | Gly | Gly | Leu | Ala | Val | Glu | Ala | Gly | His | Asn | Gly | |
| | | 275 | | | | | 280 | | | | | 285 | | | | |

| aca | ttg | tta | gca | ggt | gct | tat | aca | ata | tca | aaa | cta | ata | aca | caa | aaa | 912 |
| Thr | Leu | Leu | Ala | Gly | Ala | Tyr | Thr | Ile | Ser | Lys | Leu | Ile | Thr | Gln | Lys | |
| | 290 | | | | | 295 | | | | | 300 | | | | | |

| tta | gat | gga | ttg | aaa | aat | tca | gaa | aaa | tta | aag | gaa | aaa | att | gaa | aat | 960 |
| Leu | Asp | Gly | Leu | Lys | Asn | Ser | Glu | Lys | Leu | Lys | Glu | Lys | Ile | Glu | Asn | |
| 305 | | | | | 310 | | | | | 315 | | | | | 320 | |

| gct | aag | aaa | tgt | tct | gaa | gat | ttt | act | aaa | aaa | cta | gaa | gga | gaa | cat | 1008 |
| Ala | Lys | Lys | Cys | Ser | Glu | Asp | Phe | Thr | Lys | Lys | Leu | Glu | Gly | Glu | His | |
| | | | | 325 | | | | | 330 | | | | | 335 | | |

| gcg | caa | ctt | gga | att | gaa | aat | gtt | act | gat | gag | aat | gca | aaa | aaa | gct | 1056 |
| Ala | Gln | Leu | Gly | Ile | Glu | Asn | Val | Thr | Asp | Glu | Asn | Ala | Lys | Lys | Ala | |
| | | | 340 | | | | | 345 | | | | | 350 | | | |

| att | tta | ata | aca | gat | gca | gct | aaa | gat | aag | ggc | gct | gca | gag | ctt | gaa | 1104 |
| Ile | Leu | Ile | Thr | Asp | Ala | Ala | Lys | Asp | Lys | Gly | Ala | Ala | Glu | Leu | Glu | |
| | | | 355 | | | | | 360 | | | | | 365 | | | |

| aag | cta | ttt | aaa | gca | gta | gaa | aac | ttg | gca | aaa | gca | gct | aaa | gag | atg | 1152 |
| Lys | Leu | Phe | Lys | Ala | Val | Glu | Asn | Leu | Ala | Lys | Ala | Ala | Lys | Glu | Met | |
| 370 | | | | | 375 | | | | | 380 | | | | | | |

```
ctt gct aat tca gtt aaa gag ctt ac                                           1178
Leu Ala Asn Ser Val Lys Glu Leu
385                 390
```

<210> 74
<211> 392
<212> PRT
<213> ospC Chimera

<400> 74

| | | | | | | | | | | | | | | |
|---|---|---|---|---|---|---|---|---|---|---|---|---|---|---|
| Met | Arg | Leu | Leu | Ile | Gly | Phe | Ala | Leu | Ala | Leu | Ile | Gly | Cys | |
| 1 | | | | 5 | | | | 10 | | | | 15 | | |
| Ala | Gln | Lys | Gly | Ala | Glu | Ser | Ile | Gly | Ser | Cys | Asn | Asn | Ser | Gly | Lys |
| | | | 20 | | | | 25 | | | | 30 | | | |

```
Lys Ile Gln Gln Asn Gly Gly Leu Ala Val Glu Ala Gly His Asn Gly
            275                 280                 285
Thr Leu Leu Ala Gly Ala Tyr Thr Ile Ser Lys Leu Ile Thr Gln Lys
    290                 295                 300
Leu Asp Gly Leu Lys Asn Ser Glu Lys Leu Lys Glu Lys Ile Glu Asn
305                 310                 315                 320
Ala Lys Lys Cys Ser Glu Asp Phe Thr Lys Lys Leu Glu Gly Glu His
                325                 330                 335
Ala Gln Leu Gly Ile Glu Asn Val Thr Asp Glu Asn Ala Lys Lys Ala
            340                 345                 350
Ile Leu Ile Thr Asp Ala Ala Lys Asp Lys Gly Ala Ala Glu Leu Glu
        355                 360                 365
Lys Leu Phe Lys Ala Val Glu Asn Leu Ala Lys Ala Ala Lys Glu Met
    370                 375                 380
Leu Ala Asn Ser Val Lys Glu Leu
385                 390

<210> 75
<211> 1178
<212> DNA
<213> ospC Chimera

<220>
<221> CDS
<222> (1)...(1178)

<400> 75
atg aga tta tta ata gga ttt gct tta gc

```
gct acc aaa gct att ggt aaa aaa ata ggc aat aat ggt tta gag gcc    288
Ala Thr Lys Ala Ile Gly Lys Lys Ile Gly Asn Asn Gly Leu Glu Ala
            85                  90                  95 aat cag agt aaa aac aca tca ttg tta tca gga gct tat gca ata tct    336
Asn Gln Ser Lys Asn Thr Ser Leu Leu Ser Gly Ala Tyr Ala Ile Ser
            100                 105                 110 gac cta ata gca gaa aaa tta aat gta ttg aaa aat gaa gaa tta aag    384
Asp Leu Ile Ala Glu Lys Leu Asn Val Leu Lys Asn Glu Glu Leu Lys
            115                 120                 125 gaa aag att gat aca gct aag caa tgt tct aca gaa ttt act aat aaa    432
Glu Lys Ile Asp Thr Ala Lys Gln Cys Ser Thr Glu Phe Thr Asn Lys
            130                 135                 140 cta aaa agt gaa cat gca gtg ctt ggt ctg gac aat ctt act gat gat    480
Leu Lys Ser Glu His Ala Val Leu Gly Leu Asp Asn Leu Thr Asp Asp
145                 150                 155                 160 aat gca caa aga gct att tta aaa aaa cat gca aat aaa gat aag ggt    528
Asn Ala Gln Arg Ala Ile Leu Lys Lys His Ala Asn Lys Asp Lys Gly
            165                 170                 175 gct gca gaa ctt gaa aag tta ttt aaa gcg gta gaa aac tta tca aaa    576
Ala Ala Glu Leu Glu Lys Leu Phe Lys Ala Val Glu Asn Leu Ser Lys
            180                 185                 190 gca gct caa gac aca tta aaa aat gct gtt aaa gag ctt aca agt cct    624
Ala Ala Gln Asp Thr Leu Lys Asn Ala Val Lys Glu Leu Thr Ser Pro
            195                 200                 205 att gtc cat ggt aat aat tca aga aaa gat ggg aat gca tct aca aat    672
Ile Val His Gly Asn Asn Ser Arg Lys Asp Gly Asn Ala Ser Thr Asn
210                 215                 220 tct gcc gat gag tct gtt aaa ggg cct aat ctt aca gaa ata agt aaa    720
Ser Ala Asp Glu Ser Val Lys Gly Pro Asn Leu Thr Glu Ile Ser Lys
225                 230                 235                 240 aaa att aca gaa tct aac gca gtt gtt ctg gcc gtg aaa gaa gtt gag    768
Lys Ile Thr Glu Ser Asn Ala Val Val Leu Ala Val Lys Glu Val Glu
            245                 250                 255
```

```
acc tta ctt gca tct ata gat gaa ctt gct acc aaa gct att ggt aag    816
Thr Leu Leu Ala Ser Ile Asp Glu Leu Ala Thr Lys Ala Ile Gly Lys
            260                 265                 270 aaa ata ggc aat aat ggt tta gag gcc aat cag agt aaa aac aca tca    864
Lys Ile Gly Asn Asn Gly Leu Glu Ala Asn Gln Ser Lys Asn Thr Ser
            275                 280                 285 ttg tta tca gga gct tat gca ata tct gac cta ata gca gaa aaa tta    912
Leu Leu Ser Gly Ala Tyr Ala Ile Ser Asp Leu Ile Ala Glu Lys Leu
            290                 295                 300 aat gta ttg aaa aat gaa gaa tta aag gaa aag att gat aca gct aag    960
Asn Val Leu Lys Asn Glu Glu Leu Lys Glu Lys Ile Asp Thr Ala Lys
305                 310                 315                 320 caa tgt tct aca gaa ttt act aat aaa cta aaa agt gaa cat gca gtg   1008
Gln Cys Ser Thr Glu Phe Thr Asn Lys Leu Lys Ser Glu His Ala Val
            325                 330                 335 ctt ggt ctg gac aat ctt act gat gat aat gca caa aga gct att tta   1056
Leu Gly Leu Asp Asn Leu Thr Asp Asp Asn Ala Gln Arg Ala Ile Leu
            340                 345                 350 aaa aaa cat gca aat aaa gat aag ggt gct gca gaa ctt gaa aag tta   1104
Lys Lys His Ala Asn Lys Asp Lys Gly Ala Ala Glu Leu Glu Lys Leu
            355                 360                 365 ttt aaa gcg gta gaa aac tta tca aaa gca gct caa gac aca tta aaa   1152
Phe Lys Ala Val Glu Asn Leu Ser Lys Ala Ala Gln Asp Thr Leu Lys
            370                 375                 380 aat gct gtt aaa gag ctt aca agt cc                                 1178
Asn Ala Val Lys Glu Leu Thr Ser
385                 390
```

<210> 76
<211> 392
<212> PRT
<213> ospC Chimera

<400> 76
```
Met Arg Leu Leu Ile Gly Phe Ala Leu Ala Leu Ala Leu Ile Gly C

```
Asp Gly Asn Ala Ser Ala Asn Ser Ala Asp Glu Ser Val Lys Gly Pro
         35                  40                  45
Asn Leu Thr Glu Ile Ser Lys Lys Ile Thr Glu Ser Asn Ala Val Val
 50                  55                  60
Leu Ala Val Lys Glu Val Glu Thr Leu Leu Ala Ser Ile Asp Glu Leu
 65                  70                  75                  80
Ala Thr Lys Ala Ile Gly Lys Lys Ile Gly Asn Asn Gly Leu Glu Ala
                 85                  90                  95
Asn Gln Ser Lys Asn Thr Ser Leu Leu Ser Gly Ala Tyr Ala Ile Ser
                100                 105                 110
Asp Leu Ile Ala Glu Lys Leu Asn Val Leu Lys Asn Glu Glu Leu Lys
            115                 120                 125
Glu Lys Ile Asp Thr Ala Lys Gln Cys Ser Thr Glu Phe Thr Asn Lys
    130                 135                 140
Leu Lys Ser Glu His Ala Val Leu Gly Leu Asp Asn Leu Thr Asp Asp
145                 150                 155                 160
Asn Ala Gln Arg Ala Ile Leu Lys Lys His Ala Asn Lys Asp Lys Gly
                165                 170                 175
Ala Ala Glu Leu Glu Lys Leu Phe Lys Ala Val Glu Asn Leu Ser Lys
            180                 185                 190
Ala Ala Gln Asp Thr Leu Lys Asn Ala Val Lys Glu Leu Thr Ser Pro
    195                 200                 205
Ile Val His Gly Asn Asn Ser Arg Lys Asp Gly Asn Ala Ser Thr Asn
210                 215                 220
Ser Ala Asp Glu Ser Val Lys Gly Pro Asn Leu Thr Glu Ile Ser Lys
225                 230                 235                 240
Lys Ile Thr Glu Ser Asn Ala Val Val Leu Ala Val Lys Glu Val Glu
                245                 250                 255
Thr Leu Leu Ala Ser Ile Asp Glu Leu Ala Thr Lys Ala Ile Gly Lys
            260                 265                 270
Lys Ile Gly Asn Asn Gly Leu Glu Ala Asn Gln Ser Lys Asn Thr Ser
    275                 280                 285
Leu Leu Ser Gly Ala Tyr Ala Ile Ser Asp Leu Ile Ala Glu Lys Leu
290                 295                 300
Asn Val Leu Lys Asn Glu Glu Leu Lys Glu Lys Ile Asp Thr Ala Lys
305                 310                 315                 320
Gln Cys Ser Thr Glu Phe Thr Asn Lys Leu Lys Ser Glu His Ala Val
                325                 330                 335
Leu Gly Leu Asp Asn Leu Thr Asp Asp Asn Ala Gln Arg Ala Ile Leu
            340                 345                 350
Lys Lys His Ala Asn Lys Asp Lys Gly Ala Ala Glu Leu Glu Lys Leu
    355                 360                 365
Phe Lys Ala Val Glu Asn Leu Ser Lys Ala Ala Gln Asp Thr Leu Lys
370                 375                 380
Asn Ala Val Lys Glu Leu Thr Ser
385                 390
```

<210> 77
<211> 1230
<212> DNA
<213> ospC Chimera

<220>
<221> CDS
<222> (1)...(1230)

<400> 77

```
atg aga tta tta ata gga ttt gct tta gcg tta gct tta ata gga tgt    48
Met Arg Leu Leu Ile Gly Phe Ala Leu Ala Leu Ala Leu Ile Gly Cys
 1               5                  10                  15 gca caa aaa ggt gct gag tca att gga tcc tgt aat aat tca ggg aaa    96
Ala Gln Lys Gly Ala Glu Ser Ile Gly Ser Cys Asn Asn Ser Gly Lys
            20                  25                  30 gat ggg aat aca tct gca aat tct gct gat gag tct gtt aaa ggg cct    144
Asp Gly Asn Thr Ser Ala Asn Ser Ala Asp Glu Ser Val Lys Gly Pro
        35                  40                  45 aat ctt aca gaa ata agt aaa aaa att acg gat tct aat gcg gtt tta    192
Asn Leu Thr Glu Ile Ser Lys Lys Ile Thr Asp Ser Asn Ala Val Leu
    50                  55                  60 ctt gct gtg aaa gag gtt gaa gcg ttg ctg tca tct ata gat gaa att    240
Leu Ala Val Lys Glu Val Glu Ala Leu Leu Ser Ser Ile Asp Glu Ile
65                  70                  75                  80 gct gct aaa gct att ggt aaa aaa ata cac caa aat aat ggt ttg gat    288
Ala Ala Lys Ala Ile Gly Lys Lys Ile His Gln Asn Asn Gly Leu Asp
                85                  90                  95 acc gaa tat aat cac aat gga tca ttg tta gcg gga gct tat gca ata    336
Thr Glu Tyr Asn His Asn Gly Ser Leu Leu Ala Gly Ala Tyr Ala Ile
            100                 105                 110 tca acc cta ata aaa caa aaa tta gat gga ttg aaa aat gaa gga tta    384
Ser Thr Leu Ile Lys Gln Lys Leu Asp Gly Leu Lys Asn Glu Gly Leu
        115                 120                 125 aag gaa aaa att gat gcg gct aag aaa tgt tct gaa aca ttt act aat    432
```

```
Lys Glu Lys Ile Asp Ala Ala Lys Lys Cys Ser Glu Thr Phe Thr Asn
    130                 135                 140 aaa tta aaa gaa aaa cac aca gat ctt ggt aaa gaa ggt gtt act gat      480
Lys Leu Lys Glu Lys His Thr Asp Leu Gly Lys Glu Gly Val Thr Asp
145                 150                 155                 160 gct gat gca aaa gaa gcc att tta aaa aca aat ggt act aaa act aaa      528
Ala Asp Ala Lys Glu Ala Ile Leu Lys Thr Asn Gly Thr Lys Thr Lys
                    165                 170                 175 ggt gct gaa gaa ctt gga aaa tta ttt gaa tca gta gag gtc ttg tca      576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc      624
Lys Ala Ala Lys Glu Met Leu Ala Asn Ser Val Lys Glu Leu Thr Ser
        195                 200                 205 cct gtt gtg gca gaa agt cca aaa aaa cct ttc cat ggt aat aat tca      672
Pro Val Val Ala Glu Ser Pro Lys Lys Pro Phe His Gly Asn Asn Ser
    210                 215                 220 ggt ggg gat tct gca tct act aat cct gat gag tct gca aaa gga cct      720
Gly Gly Asp Ser Ala Ser Thr Asn Pro Asp Glu Ser Ala Lys Gly Pro
225                 230                 235                 240 aat ctt acc gta ata agc aaa aaa att aca gat tct aat gca ttt tta      768
Asn Leu Thr Val Ile Ser Lys Lys Ile Thr Asp Ser Asn Ala Phe Leu
                    245                 250                 255 ctg gct gtg aaa gaa gtt gag gct ttg ctt tca tct ata gat gaa ctt      816
Leu Ala Val Lys Glu Val Glu Ala Leu Leu Ser Ser Ile Asp Glu Leu
            260                 265                 270 tct aaa gct att ggt aaa aaa ata aaa aat gat ggt act tta gat aac      864
Ser Lys Ala Ile Gly Lys Lys Ile Lys Asn Asp Gly Thr Leu Asp Asn
        275                 280                 285 gaa gca aat cga aac gaa tca ttg ata gca gga gct tat gaa ata tca      912
Glu Ala Asn Arg Asn Glu Ser Leu Ile Ala Gly Ala Tyr Glu Ile Ser
    290                 295                 300 aaa cta ata aca caa aaa tta agt gta ttg aat tca gaa gaa tta aag      960
Lys Leu Ile Thr Gln Lys Leu Ser Val Leu Asn Ser Glu Glu Leu Lys
305                 310                 315                 320
```

```
aaa aaa att aaa gag gct aag gat tgt tcc caa aaa ttt act act aag    1008
Lys Lys Ile Lys Glu Ala Lys Asp Cys Ser Gln Lys Phe Thr Thr Lys
            325                 330                 335 cta aaa gat agt cat gca gag ctt ggt ata caa agc gtt cag gat gat    1056
Leu Lys Asp Ser His Ala Glu Leu Gly Ile Gln Ser Val Gln Asp Asp
            340                 345                 350 aat gca aaa aaa gct att tta aaa aca cat gga act aaa gac aag ggt    1104
Asn Ala Lys Lys Ala Ile Leu Lys Thr His Gly Thr Lys Asp Lys Gly
            355                 360                 365 gct aaa gaa ctt gaa gag tta ttt aaa tca cta gaa agc ttg tca aaa    1152
Ala Lys Glu Leu Glu Glu Leu Phe Lys Ser Leu Glu Ser Leu Ser Lys
            370                 375                 380 gca gcg caa gca gca tta act aat tca gtt aaa gag ctt aca aat cct    1200
Ala Ala Gln Ala Ala Leu Thr Asn Ser Val Lys Glu Leu Thr Asn Pro
385                 390                 395                 400 gtt gtg gca gaa agt cca aaa aaa cct taa                            1230
Val Val Ala Glu Ser Pro Lys Lys Pro *
                405
```

<210> 78
<211> 409
<212> PRT
<213> ospC Chimera

<400> 78

```
Met Arg Leu Leu Ile Gly Phe Ala Leu Ala Leu Ile Gly Cys
 1               5                  10                  15
Ala Gln Lys Gly Ala Glu Ser Ile Gly Ser Cys Asn Asn Ser Gly Lys
                20                  25                  30
Asp Gly Asn Thr Ser Ala Asn Ser Ala Asp Glu Ser Val Lys Gly Pro
            35                  40                  45
Asn Leu Thr Glu Ile Ser Lys Lys Ile Thr Asp Ser Asn Ala Val Leu
        50                  55                  60
Leu Ala Val Lys Glu Val Glu Ala Leu Leu Ser Ser Ile Asp Glu Ile
65                  70                  75                  80
Ala Ala Lys Ala Ile Gly Lys Lys Ile His Gln Asn Asn Gly Leu Asp
                85                  90                  95
Thr Glu Tyr Asn His Asn Gly Ser Leu Leu Ala Gly Ala Tyr Ala Ile
            100                 105                 110
Ser Thr Leu Ile Lys Gln Lys Leu Asp Gly Leu Lys Asn Glu Gly Leu
        115                 120                 125
```

```
Lys Glu Lys Ile Asp Ala Ala Lys Lys Cys Ser Glu Thr Phe Thr Asn
    130                 135                 140
Lys Leu Lys Glu Lys His Thr Asp Leu Gly Lys Glu Gly Val Thr Asp
145                 150                 155                 160
Ala Asp Ala Lys Glu Ala Ile Leu Lys Thr Asn Gly Thr Lys Thr Lys
                165                 170                 175
Gly Ala Glu Glu Leu Gly Lys Leu Phe Glu Ser Val Glu Val Leu Ser
                180                 185                 190
Lys Ala Ala Lys Glu Met Leu Ala Asn Ser Val Lys Glu Leu Thr Ser
            195                 200                 205
Pro Val Val Ala Glu Ser Pro Lys Lys Pro Phe His Gly Asn Asn Ser
    210                 215                 220
Gly Gly Asp Ser Ala Ser Thr Asn Pro Asp Glu Ser Ala Lys Gly Pro
225                 230                 235                 240
Asn Leu Thr Val Ile Ser Lys Lys Ile Thr Asp Ser Asn Ala Phe Leu
                245                 250                 255
Leu Ala Val Lys Glu Val Glu Ala Leu Leu Ser Ser Ile Asp Glu Leu
                260                 265                 270
Ser Lys Ala Ile Gly Lys Lys Ile Lys Asn Asp Gly Thr Leu Asp Asn
            275                 280                 285
Glu Ala Asn Arg Asn Glu Ser Leu Ile Ala Gly Ala Tyr Glu Ile Ser
    290                 295                 300
Lys Leu Ile Thr Gln Lys Leu Ser Val Leu Asn Ser Glu Glu Leu Lys
305                 310                 315                 320
Lys Lys Ile Lys Glu Ala Lys Asp Cys Ser Gln Lys Phe Thr Thr Lys
                325                 330                 335
Leu Lys Asp Ser His Ala Glu Leu Gly Ile Gln Ser Val Gln Asp Asp
                340                 345                 350
Asn Ala Lys Lys Ala Ile Leu Lys Thr His Gly Thr Lys Asp Lys Gly
            355                 360                 365
Ala Lys Glu Leu Glu Glu Leu Phe Lys Ser Leu Glu Ser Leu Ser Lys
    370                 375                 380
Ala Ala Gln Ala Ala Leu Thr Asn Ser Val Lys Glu Leu Thr Asn Pro
385                 390                 395                 400
Val Val Ala Glu Ser Pro Lys Lys Pro
                405

<210> 79
<211> 1209
<212> DNA
<213> ospC Chimera

<220>
<221> CDS
<222> (1)...(1209)
```

<400> 79

| | | | | | | | | | | | | | | | | |
|---|---|---|---|---|---|---|---|---|---|---|---|---|---|---|---|---|
| atg | aga | tta | tta | ata | gga | ttt | gct | tta | gcg | tta | gct | tta | ata | gga | tgt | 48 |
| Met | Arg | Leu | Leu | Ile | Gly | Phe | Ala | Leu | Ala | Leu | Ala | Leu | Ile | Gly | Cys | |
| 1 | | | | 5 | | | | | 10 | | | | | 15 | | |

| gca | caa | aaa | ggt | gct | gag | tca | att | gga | tcc | tgt | aat | aat | tca | ggg | aaa | 96 |
|---|---|---|---|---|---|---|---|---|---|---|---|---|---|---|---|---|
| Ala | Gln | Lys | Gly | Ala | Glu | Ser | Ile | Gly | Ser | Cys | Asn | Asn | Ser | Gly | Lys | |
| | | | 20 | | | | | 25 | | | | | 30 | | | |

| gat | ggg | aat | aca | tct | gca | aat | tct | gct | gat | gag | tct | gtt | aaa | ggg | cct | 144 |
|---|---|---|---|---|---|---|---|---|---|---|---|---|---|---|---|---|
| Asp | Gly | Asn | Thr | Ser | Ala | Asn | Ser | Ala | Asp | Glu | Ser | Val | Lys | Gly | Pro | |
| | | 35 | | | | | 40 | | | | | 45 | | | | |

| aat | ctt | aca | gaa | ata | agt | aaa | aaa | att | acg | gat | tct | aat | gcg | gtt | tta | 192 |
|---|---|---|---|---|---|---|---|---|---|---|---|---|---|---|---|---|
| Asn | Leu | Thr | Glu | Ile | Ser | Lys | Lys | Ile | Thr | Asp | Ser | Asn | Ala | Val | Leu | |
| 50 | | | | | 55 | | | | | 60 | | | | | | |

| ctt | gct | gtg | aaa | gag | gtt | gaa | gcg | ttg | ctg | tca | tct | ata | gat | gaa | att | 240 |
|---|---|---|---|---|---|---|---|---|---|---|---|---|---|---|---|---|
| Leu | Ala | Val | Lys | Glu | Val | Glu | Ala | Leu | Leu | Ser | Ser | Ile | Asp | Glu | Ile | |
| 65 | | | | | 70 | | | | | 75 | | | | | 80 | |

| gct | gct | aaa | gct | att | ggt | aaa | aaa | ata | cac | caa | aat | aat | ggt | ttg | gat | 288 |
|---|---|---|---|---|---|---|---|---|---|---|---|---|---|---|---|---|
| Ala | Ala | Lys | Ala | Ile | Gly | Lys | Lys | Ile | His | Gln | Asn | Asn | Gly | Leu | Asp | |
| | | | | 85 | | | | | 90 | | | | | 95 | | |

| acc | gaa | tat | aat | cac | aat | gga | tca | ttg | tta | gcg | gga | gct | tat | gca | ata | 336 |
|---|---|---|---|---|---|---|---|---|---|---|---|---|---|---|---|---|
| Thr | Glu | Tyr | Asn | His | Asn | Gly | Ser | Leu | Leu | Ala | Gly | Ala | Tyr | Ala | Ile | |
| | | | | 100 | | | | | 105 | | | | | 110 | | |

| tca | acc | cta | ata | aaa | caa | aaa | tta | gat | gga | ttg | aaa | aat | gaa | gga | tta | 384 |
|---|---|---|---|---|---|---|---|---|---|---|---|---|---|---|---|---|
| Ser | Thr | Leu | Ile | Lys | Gln | Lys | Leu | Asp | Gly | Leu | Lys | Asn | Glu | Gly | Leu | |
| | | | 115 | | | | | 120 | | | | | 125 | | | |

| aag | gaa | aaa | att | gat | gcg | gct | aag | aaa | tgt | tct | gaa | aca | ttt | act | aat | 432 |
|---|---|---|---|---|---|---|---|---|---|---|---|---|---|---|---|---|
| Lys | Glu | Lys | Ile | Asp | Ala | Ala | Lys | Lys | Cys | Ser | Glu | Thr | Phe | Thr | Asn | |
| | | 130 | | | | | 135 | | | | | 140 | | | | |

| aaa | tta | aaa | gaa | aaa | cac | aca | gat | ctt | ggt | aaa | gaa | ggt | gtt | act | gat | 480 |
|---|---|---|---|---|---|---|---|---|---|---|---|---|---|---|---|---|
| Lys | Leu | Lys | Glu | Lys | His | Thr | Asp | Leu | Gly | Lys | Glu | Gly | Val | Thr | Asp | |
| 145 | | | | | 150 | | | | | 155 | | | | | 160 | |

| gct | gat | gca | aaa | gaa | gcc | att | tta | aaa | aca | aat | ggt | act | aaa | act | aaa | 528 |
|---|---|---|---|---|---|---|---|---|---|---|---|---|---|---|---|---|
| Ala | Asp | Ala | Lys | Glu | Ala | Ile | Leu | Lys | Thr | Asn | Gly | Thr | Lys | Thr | Lys | |
| | | | | 165 | | | | | 170 | | | | | 175 | | |

| ggt | gct | gaa | gaa | ctt | gga | aaa | tta | ttt | gaa | tca | gta | gag | gtc | ttg | tca | 576 |
|---|---|---|---|---|---|---|---|---|---|---|---|---|---|---|---|---|

```
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc    624
Lys Ala Ala Lys Glu Met Leu Ala Asn Ser Val Lys Glu Leu Thr Ser
            195                 200                 205 cct gtt gtg gca gaa agt cca aaa aaa cct tcc atg gta aat aat tca    672
Pro Val Val Ala Glu Ser Pro Lys Lys Pro Ser Met Val Asn Asn Ser
    210                 215                 220 ggg aaa gat ggg aat aca tct gca aat tct gct gat gag tct gtt aaa    720
Gly Lys Asp Gly Asn Thr Ser Ala Asn Ser Ala Asp Glu Ser Val Lys
225                 230                 235                 240 ggg cct aat ctt aca gaa ata agt aaa aaa att aca gaa tct aac gca    768
Gly Pro Asn Leu Thr Glu Ile Ser Lys Lys Ile Thr Glu Ser Asn Ala
            245                 250                 255 gtt gtt ctc gcc gtg aaa gaa gtt gaa act ttg ctt aca tct ata gat    816
Val Val Leu Ala Val Lys Glu Val Glu Thr Leu Leu Thr Ser Ile Asp
            260                 265                 270 gag ctt gct aaa gct att ggt aaa aaa ata aaa aac gat gtt agt tta    864
Glu Leu Ala Lys Ala Ile Gly Lys Lys Ile Lys Asn Asp Val Ser Leu
            275                 280                 285 gat aat gag gca gat cac aac gga tca tta ata tca gga gca tat tta    912
Asp Asn Glu Ala Asp His Asn Gly Ser Leu Ile Ser Gly Ala Tyr Leu
            290                 295                 300 att tca aac tta ata aca aaa aaa ata agt gca ata aaa gat tca gga    960
Ile Ser Asn Leu Ile Thr Lys Lys Ile Ser Ala Ile Lys Asp Ser Gly
305                 310                 315                 320 gaa ttg aag gca gaa att gaa aag gct aag aaa tgt tct gaa gaa ttt   1008
Glu Leu Lys Ala Glu Ile Glu Lys Ala Lys Lys Cys Ser Glu Glu Phe
            325                 330                 335 act gct aaa tta aaa ggt gaa cac aca gat ctt ggt aaa gaa ggc gtt   1056
Thr Ala Lys Leu Lys Gly Glu His Thr Asp Leu Gly Lys Glu Gly Val
            340                 345                 350 act gat gat aat gca aaa aaa gcc att tta aaa aca aat aat gat aaa   1104
Thr Asp Asp Asn Ala Lys Lys Ala Ile Leu Lys Thr Asn Asn Asp Lys
            355                 360                 365
```

```
act aag ggc gct gat gaa ctt gaa aag tta ttt gaa tca gta aaa aac   1152
Thr Lys Gly Ala Asp Glu Leu Glu Lys Leu Phe Glu Ser Val Lys Asn
    370                 375                 380 ttg tca aaa gca gct aaa gag atg ctt act aat tca gtt aaa gag ctt   1200
Leu Ser Lys Ala Ala Lys Glu Met Leu Thr Asn Ser Val Lys Glu Leu
385                 390                 395                 400 aca agc taa                                                       1209
Thr Ser *
```

<210> 80
<211> 402
<212> PRT
<213> ospC Chimera

<400> 80

```
Met Arg Leu Leu Ile Gly Phe Ala Leu Ala Leu Ala Leu Ile Gly Cys
 1               5                  10                  15
Ala Gln Lys Gly Ala Glu Ser Ile Gly Ser Cys Asn Asn Ser Gly Lys
            20                  25                  30
Asp Gly Asn Thr Ser Ala Asn Ser Ala Asp Glu Ser Val Lys Gly Pro
        35                  40                  45

```
Gly Lys Asp Gly Asn Thr Ser Ala Asn Ser Ala Asp Glu Ser Val Lys
225                 230                 235                 240
Gly Pro Asn Leu Thr Glu Ile Ser Lys Lys Ile Thr Glu Ser Asn Ala
                245                 250                 255
Val Val Leu Ala Val Lys Glu Val Glu Thr Leu Leu Thr Ser Ile Asp
            260                 265                 270
Glu Leu Ala Lys Ala Ile Gly Lys Lys Ile Lys Asn Asp Val Ser Leu
        275                 280                 285
Asp Asn Glu Ala Asp His Asn Gly Ser Leu Ile Ser Gly Ala Tyr Leu
    290                 295                 300
Ile Ser Asn Leu Ile Thr Lys Lys Ile Ser Ala Ile Lys Asp Ser Gly
305                 310                 315                 320
Glu Leu Lys Ala Glu Ile Glu Lys Ala Lys Lys Cys Ser Glu Glu Phe
                325                 330                 335
Thr Ala Lys Leu Lys Gly Glu His Thr Asp Leu Gly Lys Glu Gly Val
            340                 345                 350
Thr Asp Asp Asn Ala Lys Lys Ala Ile Leu Lys Thr Asn Asn Asp Lys
        355                 360                 365
Thr Lys Gly Ala Asp Glu Leu Glu Lys Leu Phe Glu Ser Val Lys Asn
    370                 375                 380
Leu Ser Lys Ala Ala Lys Glu Met Leu Thr Asn Ser Val Lys Glu Leu
385                 390                 395                 400
Thr Ser

<210> 81
<211> 1205
<212> DNA
<213> ospC Chimera

<220>
<221> CDS
<222> (1)...(1205)

<400> 81
atg aga tta tta ata

```
aat ctt aca gaa ata agt aaa aaa att acg gat tct aat gcg gtt tta    192
Asn Leu Thr Glu Ile Ser Lys Lys Ile Thr Asp Ser Asn Ala Val Leu
        50              55                  60 ctt gct gtg aaa gag gtt gaa gcg ttg ctg tca tct ata gat gaa att    240
Leu Ala Val Lys Glu Val Glu Ala Leu Leu Ser Ser Ile Asp Glu Ile
65              70                  75                  80 gct gct aaa gct att ggt aaa aaa ata cac caa aat aat ggt ttg gat    288
Ala Ala Lys Ala Ile Gly Lys Lys Ile His Gln Asn Asn Gly Leu Asp
                85                  90                  95 acc gaa tat aat cac aat gga tca ttg tta gcg gga gct tat gca ata    336
Thr Glu Tyr Asn His Asn Gly Ser Leu Leu Ala Gly Ala Tyr Ala Ile
            100                 105                 110 tca acc cta ata aaa caa aaa tta gat gga ttg aaa aat gaa gga tta    384
Ser Thr Leu Ile Lys Gln Lys Leu Asp Gly Leu Lys Asn Glu Gly Leu
        115                 120                 125 aag gaa aaa att gat gcg gct aag aaa tgt tct gaa aca ttt act aat    432
Lys Glu Lys Ile Asp Ala Ala Lys Lys Cys Ser Glu Thr Phe Thr Asn
        130                 135                 140 aaa tta aaa gaa aaa cac aca gat ctt ggt aaa gaa ggt gtt act gat    480
Lys Leu Lys Glu Lys His Thr Asp Leu Gly Lys Glu Gly Val Thr Asp
145                 150                 155                 160 gct gat gca aaa gaa gcc att tta aaa aca aat ggt act aaa act aaa    528
Ala Asp Ala Lys Glu Ala Ile Leu Lys Thr Asn Gly Thr Lys Thr Lys
                165                 170                 175 ggt gct gaa gaa ctt gga aaa tta ttt gaa tca gta gag gtc ttg tca    576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc    624
Lys Ala Ala Lys Glu Met Leu Ala Asn Ser Val Lys Glu Leu Thr Ser
        195                 200                 205 cct gtt gtg gca gaa agt cca aaa aaa cct tcc atg gta aat aat tca    672
Pro Val Val Ala Glu Ser Pro Lys Lys Pro Ser Met Val Asn Asn Ser
        210                 215                 220 gga aaa gat ggg aat aca tct gca aat tct gct gat gag tct gtt aaa    720
Gly Lys Asp Gly Asn Thr Ser Ala Asn Ser Ala Asp Glu Ser Val Lys
225                 230                 235                 240
```

```
ggg cct aat ctt aca gaa ata agt aaa aaa att aca gaa tct aac gca    768
Gly Pro Asn Leu Thr Glu Ile Ser Lys Lys Ile Thr Glu Ser Asn Ala
            245                 250                 255 gtt gtt ctg gct gtg aaa gaa att gaa act ttg ctt gca tct ata gat    816
Val Val Leu Ala Val Lys Glu Ile Glu Thr Leu Leu Ala Ser Ile Asp
            260                 265                 270 gaa ctt gct act aaa gct att ggt aaa aaa ata caa caa aat ggt ggt    864
Glu Leu Ala Thr Lys Ala Ile Gly Lys Lys Ile Gln Gln Asn Gly Gly
            275                 280                 285 tta gct gtc gaa gcg ggg cat aat gga aca ttg tta gca ggt gct tat    912
Leu Ala Val Glu Ala Gly His Asn Gly Thr Leu Leu Ala Gly Ala Tyr
            290                 295                 300 aca ata tca aaa cta ata aca caa aaa tta gat gga ttg aaa aat tca    960
Thr Ile Ser Lys Leu Ile Thr Gln Lys Leu Asp Gly Leu Lys Asn Ser
305                 310                 315                 320 gaa aaa tta aag gaa aaa att gaa aat gct aag aaa tgt tct gaa gat   1008
Glu Lys Leu Lys Glu Lys Ile Glu Asn Ala Lys Lys Cys Ser Glu Asp
            325                 330                 335 ttt act aaa aaa cta gaa gga gaa cat gcg caa ctt gga att gaa aat   1056
Phe Thr Lys Lys Leu Glu Gly Glu His Ala Gln Leu Gly Ile Glu Asn
            340                 345                 350 gtt act gat gag aat gca aaa aaa gct att tta ata aca gat gca gct   1104
Val Thr Asp Glu Asn Ala Lys Lys Ala Ile Leu Ile Thr Asp Ala Ala
            355                 360                 365 aaa gat aag ggc gct gca gag ctt gaa aag cta ttt aaa gca gta gaa   1152
Lys Asp Lys Gly Ala Ala Glu Leu Glu Lys Leu Phe Lys Ala Val Glu
            370                 375                 380 aac ttg gca aaa gca gct aaa gag atg ctt gct aat tca gtt aaa gag   1200
Asn Leu Ala Lys Ala Ala Lys Glu Met Leu Ala Asn Ser Val Lys Glu
385                 390                 395                 400 ctt ac                                                             1205
Leu
```

<210> 82
<211> 401
<212> PRT
<213> ospC Chimera

<400> 82

| | | | | | | | | | | | | | | | |
|---|---|---|---|---|---|---|---|---|---|---|---|---|---|---|---|
| Met | Arg | Leu | Leu | Ile | Gly | Phe | Ala | Leu | Ala | Leu | Ile | Gly | Cys |
| 1 | | | | 5 | | | | | 10 | | | | | 15 |
| Ala | Gln | Lys | Gly | Ala | Glu | Ser | Ile | Gly | Ser | Cys | Asn | Asn | Ser | Gly | Lys |
| | | | 20 | | | | | 25 | | | | | 30 | |
| Asp | Gly | Asn | Thr | Ser | Ala | Asn | Ser | Ala | Asp | Glu | Ser | Val | Lys | Gly | Pro |
| | | 35 | | | | | 40 | | | | | 45 | | |
| Asn | Leu | Thr | Glu | Ile | Ser | Lys | Lys | Ile | Thr | Asp | Ser | Asn | Ala | Val | Leu |
| | 50 | | | | | 55 | | | | | 60 | | | |
| Leu | Ala | Val | Lys | Glu | Val | Glu | Ala | Leu | Leu | Ser | Ser | Ile | Asp | Glu | Ile |
| 65 | | | | | 70 | | | | | 75 | | | | | 80 |
| Ala | Ala | Lys | Ala | Ile | Gly | Lys | Lys | Ile | His | Gln | Asn | Asn | Gly | Leu | Asp |
| | | | 85 | | | | | 90 | | | | | 95 | |
| Thr | Glu | Tyr | Asn | His | Asn | Gly | Ser | Leu | Leu | Ala | Gly | Ala | Tyr | Ala | Ile |
| | | | 100 | | | | | 105 | | | | | 110 | |
| Ser | Thr | Leu | Ile | Lys | Gln | Lys | Leu | Asp | Gly | Leu | Lys | Asn | Glu | Gly | Leu |
| | | 115 | | | | | 120 | | | | | 125 | | |
| Lys | Glu | Lys | Ile | Asp | Ala | Ala | Lys | Lys | Cys | Ser | Glu | Thr | Phe | Thr | Asn |
| | 130 | | | | | 135 | | | | | 140 | | | |
| Lys | Leu | Lys | Glu | Lys | His | Thr | Asp | Leu | Gly | Lys | Glu | Gly | Val | Thr | Asp |
| 145 | | | | | 150 | | | | | 155 | | | | | 160 |
| Ala | Asp | Ala | Lys | Glu | Ala | Ile | Leu | Lys | Thr | Asn | Gly | Thr | Lys | Thr | Lys |
| | | | 165 | | | | | 170 | | | | | 175 | |
| Gly | Ala | Glu | Glu | Leu | Gly | Lys | Leu | Phe | Glu | Ser | Val | Glu | Val | Leu | Ser |
| | | | 180 | | | | | 185 | | | | | 190 | |
| Lys | Ala | Ala | Lys | Glu | Met | Leu | Ala | Asn | Ser | Val | Lys | Glu | Leu | Thr | Ser |
| | | 195 | | | | | 200 | | | | | 205 | | |
| Pro | Val | Val | Ala | Glu | Ser | Pro | Lys | Lys | Pro | Ser | Met | Val | Asn | Asn | Ser |
| | 210 | | | | | 215 | | | | | 220 | | | |
| Gly | Lys | Asp | Gly | Asn | Thr | Ser | Ala | Asn | Ser | Ala | Asp | Glu | Ser | Val | Lys |
| 225 | | | | | 230 | | | | | 235 | | | | | 240 |
| Gly | Pro | Asn | Leu | Thr | Glu | Ile | Ser | Lys | Lys | Ile | Thr | Glu | Ser | Asn | Ala |
| | | | 245 | | | | | 250 | | | | | 255 | |
| Val | Val | Leu | Ala | Val | Lys | Glu | Ile | Glu | Thr | Leu | Leu | Ala | Ser | Ile | Asp |
| | | | 260 | | | | | 265 | | | | | 270 | |
| Glu | Leu | Ala | Thr | Lys | Ala | Ile | Gly | Lys | Lys | Ile | Gln | Gln | Asn | Gly | Gly |
| | | 275 | | | | | 280 | | | | | 285 | | |
| Leu | Ala | Val | Glu | Ala | Gly | His | Asn | Gly | Thr | Leu | Leu | Ala | Gly | Ala | Tyr |
| | | 290 | | | | | 295 | | | | | 300 | | |
| Thr | Ile | Ser | Lys | Leu | Ile | Thr | Gln | Lys | Leu | Asp | Gly | Leu | Lys | Asn | Ser |
| 305 | | | | | 310 | | | | | 315 | | | | | 320 |

```
Glu Lys Leu Lys Glu Lys Ile Glu Asn Ala Lys Lys Cys Ser Glu Asp
            325                 330                 335
Phe Thr Lys Lys Leu Glu Gly Glu His Ala Gln Leu Gly Ile Glu Asn
            340                 345                 350
Val Thr Asp Glu Asn Ala Lys Lys Ala Ile Leu Ile Thr Asp Ala Ala
            355                 360                 365
Lys Asp Lys Gly Ala Ala Glu Leu Glu Lys Leu Phe Lys Ala Val Glu
    370                 375                 380
Asn Leu Ala Lys Ala Ala Lys Glu Met Leu Ala Asn Ser Val Lys Glu
385                 390                 395                 400
Leu

<210> 83
<211> 1236
<212> DNA
<213> ospC Chimera

<220>
<221> CDS
<222> (1)...(1236)

<400> 83
atg aga tta tta ata gga ttt gct tta gcg tta gct tta ata gga tgt    48
Met Arg Leu Leu Ile Gly Phe Ala Leu Ala Leu Ala Leu Ile Gly Cys
 1               5                  10                  15 gca caa aaa ggt gct gag tca att gga tcc tgt agt aat tca ggg aaa    96
Ala Gln Lys Gly Ala Glu Ser Ile Gly Ser Cys Ser Asn Ser Gly Lys
                20                  25                  30 ggt ggg gat tct gca tct act aat cct gct gac gag tct gcg aaa ggg   144
Gly Gly Asp Ser Ala Ser Thr Asn Pro Ala Asp Glu Ser Ala Lys Gly
             35                  40                  45 cct aat ctt aca gaa ata agc aaa aaa att aca gat tct aat gca ttt   192
Pro Asn Leu Thr Glu Ile Ser Lys Lys Ile Thr Asp Ser Asn Ala Phe
         50                  55                  60 gta ctt gct gtt aaa gaa gtt gag act ttg gtt tta tct ata gat gaa   240
Val Leu Ala Val Lys Glu Val Glu Thr Leu Val Leu Ser Ile Asp Glu
 65                  70                  75                  80 ctt gct aag aaa gct att ggt caa aaa ata gac aat aat aat ggt tta   288
Leu Ala Lys Lys Ala Ile Gly Gln Lys Ile Asp Asn Asn Asn Gly Leu
                 85                  90                  95
```

```
gct gct tta aat aat cag aat gga tcg ttg tta gca gga gcc tat gca    336
Ala Ala Leu Asn Asn Gln Asn Gly Ser Leu Leu Ala Gly Ala Tyr Ala
            100                 105                 110 ata tca acc cta ata aca gaa aaa ttg agt aaa ttg aaa aat tta gaa    384
Ile Ser Thr Leu Ile Thr Glu Lys Leu Ser Lys Leu Lys Asn Leu Glu
        115                 120                 125 gaa tta aag aca gaa att gca aag gct aag aaa tgt tcc gaa gaa ttt    432
Glu Leu Lys Thr Glu Ile Ala Lys Ala Lys Lys Cys Ser Glu Glu Phe
    130                 135                 140 act aat aaa cta aaa agt ggt cat gca gat ctt ggc aaa cag gat gct    480
Thr Asn Lys Leu Lys Ser Gly His Ala Asp Leu Gly Lys Gln Asp Ala
145                 150                 155                 160 acc gat gat cat gca aaa gca gct att tta aaa aca cat gca act acc    528
Thr Asp Asp His Ala Lys Ala Ala Ile Leu Lys Thr His Ala Thr Thr
                165                 170                 175 gat aaa ggt gct aaa gaa ttt aaa gat tta ttt gaa tca gta gaa ggt    576
Asp Lys Gly Ala Lys Glu Phe Lys Asp Leu Phe Glu Ser Val Glu Gly
            180                 185                 190 ttg tta aaa gca gct caa gta gca cta act aat tca gtt aaa gaa ctt    624
Leu Leu Lys Ala Ala Gln Val Ala Leu Thr Asn Ser Val Lys Glu Leu
        195                 200                 205 aca agt cct gtt gta gca gaa agt cca aaa aaa cct cat atg gct aat    672
Thr Ser Pro Val Val Ala Glu Ser Pro Lys Lys Pro His Met Ala Asn
    210                 215                 220 aat tca ggt ggg gat tct gca tct act aat cct gat gag tct gca aaa    720
Asn Ser Gly Gly Asp Ser Ala Ser Thr Asn Pro Asp Glu Ser Ala Lys
225                 230                 235                 240 gga cct aat ctt acc gta ata agc aaa aaa att aca gat tct aat gca    768
Gly Pro Asn Leu Thr Val Ile Ser Lys Lys Ile Thr Asp Ser Asn Ala
                245                 250                 255 ttt tta ctg gct gtg aaa gaa gtt gag gct ttg ctt tca tct ata gat    816
Phe Leu Leu Ala Val Lys Glu Val Glu Ala Leu Leu Ser Ser Ile Asp
            260                 265                 270 gaa ctt tct aaa gct att ggt aaa aaa ata aaa aat gat ggt act tta    864
Glu Leu Ser Lys Ala Ile Gly Lys Lys Ile Lys Asn Asp Gly Thr Leu
        275                 280                 285
```

```
gat aac gaa gca aat cga aac gaa tca ttg ata gca gga gct tat gaa    912
Asp Asn Glu Ala Asn Arg Asn Glu Ser Leu Ile Ala Gly Ala Tyr Glu
    290                 295                 300 ata tca aaa cta ata aca caa aaa tta agt gta ttg aat tca gaa gaa    960
Ile Ser Lys Leu Ile Thr Gln Lys Leu Ser Val Leu Asn Ser Glu Glu
305                 310                 315                 320 tta aag aaa aaa att aaa gag gct aag gat tgt tcc caa aaa ttt act    1008
Leu Lys Lys Lys Ile Lys Glu Ala Lys Asp Cys Ser Gln Lys Phe Thr
                325                 330                 335 act aag cta aaa gat agt cat gca gag ctt ggt ata caa agc gtt cag    1056
Thr Lys Leu Lys Asp Ser His Ala Glu Leu Gly Ile Gln Ser Val Gln
            340                 345                 350 gat gat aat gca aaa aaa gct att tta aaa aca cat gga act aaa gac    1104
Asp Asp Asn Ala Lys Lys Ala Ile Leu Lys Thr His Gly Thr Lys Asp
        355                 360                 365 aag ggt gct aaa gaa ctt gaa gag tta ttt aaa tca cta gaa agc ttg    1152
Lys Gly Ala Lys Glu Leu Glu Glu Leu Phe Lys Ser Leu Glu Ser Leu
    370                 375                 380 tca aaa gca gcg caa gca gca tta act aat tca gtt aaa gag ctt aca    1200
Ser Lys Ala Ala Gln Ala Ala Leu Thr Asn Ser Val Lys Glu Leu Thr
385                 390                 395                 400 aat cct gtt gtg gca gaa agt cca aaa aaa cct taa                    1236
Asn Pro Val Val Ala Glu Ser Pro Lys Lys Pro *
                405                 410

<210> 84
<211> 411
<212> PRT
<213> ospC Chimera

<400> 84
Met Arg Leu Leu Ile Gly Phe Ala Leu Ala Leu Ala Leu Ile Gly Cys
1               5                   10                  15
Ala Gln Lys Gly Ala Glu Ser Ile Gly Ser Cys Ser Asn Ser Gly Lys
            20                  25                  30
Gly Gly

```
Pro Asn Leu Thr Glu Ile Ser Lys Lys Ile Thr Asp Ser Asn Ala Phe
    50                  55                  60
Val Leu Ala Val Lys Glu Val Glu Thr Leu Val Leu Ser Ile Asp Glu
65              70                  75                          80
Leu Ala Lys Lys Ala Ile Gly Gln Lys Ile Asp Asn Asn Asn Gly Leu
                85                  90                  95
Ala Ala Leu Asn Asn Gln Asn Gly Ser Leu Leu Ala Gly Ala Tyr Ala
            100                 105                 110
Ile Ser Thr Leu Ile Thr Glu Lys Leu Ser Lys Leu Lys Asn Leu Glu
        115                 120                 125
Glu Leu Lys Thr Glu Ile Ala Lys Ala Lys Lys Cys Ser Glu Glu Phe
    130                 135                 140
Thr Asn Lys Leu Lys Ser Gly His Ala Asp Leu Gly Lys Gln Asp Ala
145                 150                 155                 160
Thr Asp Asp His Ala Lys Ala Ala Ile Leu Lys Thr His Ala Thr Thr
                165                 170                 175
Asp Lys Gly Ala Lys Glu Phe Lys Asp Leu Phe Glu Ser Val Glu Gly
            180                 185                 190
Leu Leu Lys Ala Ala Gln Val Ala Leu Thr Asn Ser Val Lys Glu Leu
        195                 200                 205
Thr Ser Pro Val Val Ala Glu Ser Pro Lys Lys Pro His Met Ala Asn
    210                 215                 220
Asn Ser Gly Gly Asp Ser Ala Ser Thr Asn Pro Asp Glu Ser Ala Lys
225                 230                 235                 240
Gly Pro Asn Leu Thr Val Ile Ser Lys Lys Ile Thr Asp Ser Asn Ala
                245                 250                 255
Phe Leu Leu Ala Val Lys Glu Val Glu Ala Leu Leu Ser Ser Ile Asp
            260                 265                 270
Glu Leu Ser Lys Ala Ile Gly Lys Lys Ile Lys Asn Asp Gly Thr Leu
        275                 280                 285
Asp Asn Glu Ala Asn Arg Asn Glu Ser Leu Ile Ala Gly Ala Tyr Glu
    290                 295                 300
Ile Ser Lys Leu Ile Thr Gln Lys Leu Ser Val Leu Asn Ser Glu Glu
305                 310                 315                 320
Leu Lys Lys Lys Ile Lys Glu Ala Lys Asp Cys Ser Gln Lys Phe Thr
                325                 330                 335
Thr Lys Leu Lys Asp Ser His Ala Glu Leu Gly Ile Gln Ser Val Gln
            340                 345                 350
Asp Asp Asn Ala Lys Lys Ala Ile Leu Lys Thr His Gly Thr Lys Asp
        355                 360                 365
Lys Gly Ala Lys Glu Leu Glu Glu Leu Phe Lys Ser Leu Glu Ser Leu
    370                 375                 380
Ser Lys Ala Ala Gln Ala Ala Leu Thr Asn Ser Val Lys Glu Leu Thr
385                 390                 395                 400

Asn Pro Val Val Ala Glu Ser Pro Lys Lys Pro
                405                 410
```

```
<210> 85
<211> 192
<212> PRT
<213> borrelia burgdorferi

<400> 85
Cys Asn Asn Ser Gly Lys Asp Gly Asn Thr Ser Ala Asn Ser Ala Asp
1               5                   10                  15
Glu Ser Val Lys Gly Pro Asn Leu Thr Glu Ile Ser Lys Lys Ile Thr
            20                  25                  30
Glu Ser Asn Ala Val Val Leu Ala Val Lys Glu Val Glu Thr Leu Leu
        35                  40                  45
Thr Ser Ile Asp Glu Leu Ala Lys Ala Ile Gly Lys Lys Ile Lys Asn
    50                  55                  60
Asp Val Ser Leu Asp Asn Glu Ala Asp His Asn Gly Ser Leu Ile Ser
65                  70                  75                  80
Gly Ala Tyr Leu Ile Ser Thr Leu Ile Thr Lys Lys Ile Ser Ala Ile
                85                  90                  95
Lys Asp Ser Gly Glu Leu Lys Ala Glu Ile Glu Lys Ala Lys Lys Cys
            100                 105                 110
Ser Glu Glu Phe Thr Ala Lys Leu Lys Gly Glu His Thr Asp Leu Gly
        115                 120                 125
Lys Glu Gly Val Thr Asp Asp Asn Ala Lys Lys Ala Ile Leu Lys Thr
    130                 135                 140
Asn Asn Asp Lys Thr Lys Gly Ala Asp Glu Leu Glu Lys Leu Phe Glu
145                 150                 155                 160
Ser Val Lys Asn Leu Ser Lys Ala Ala Lys Glu Met Leu Thr Asn Ser
                165                 170                 175
Val Lys Glu Leu Thr Ser Pro Val Val Ala Glu Ser Pro Lys Lys Pro
            180                 185                 190

<210> 86
<211> 191
<212> PRT
<213> borrelia burgdorferi

<400> 86
Asn Ser Gly Lys Gly Gly Asn Thr Ser Ala Asn Ser Ala Asp Glu Ser
1               5                   10                  15
Val Lys Gly Pro Asn Leu Thr Glu Ile Ser Lys Lys Ile Thr Glu Ser
            20                  25                  30
Asn Ala Val Val Leu Ala Val Lys Glu Ile Glu Thr Leu Leu Ala Ser
        35                  40                  45
```

```
Ile Asp Glu Leu Ala Thr Lys Ala Ile Gly Lys Lys Ile Gln Gln Asn
     50                  55                  60
Gly Gly Leu Ala Val Glu Ala Gly His Asn Gly Thr Leu Leu Ala Gly
65                   70                  75                  80
Ala Tyr Thr Ile Ser Lys Leu Ile Thr Gln Lys Leu Asp Gly Leu Lys
                 85                  90                  95
Asn Ser Glu Lys Leu Lys Glu Lys Ile Glu Asn Ala Lys Lys Cys Ser
            100                 105                 110
Glu Asp Phe Thr Lys Lys Leu Glu Gly Glu His Ala Gln Leu Gly Ile
            115                 120                 125
Glu Asn Val Thr Asp Glu Asn Ala Lys Lys Ala Ile Leu Ile Thr Asp
            130                 135                 140
Ala Ala Lys Asp Lys Gly Ala Ala Glu Leu Glu Lys Leu Phe Lys Ala
145                 150                 155                 160
Val Glu Asn Leu Ala Lys Ala Ala Lys Glu Met Leu Ala Asn Ser Val
                165                 170                 175
Lys Glu Leu Thr Ser Pro Ile Val Ala Glu Ser Pro Lys Lys Pro
            180                 185                 190
```